(12) United States Patent
Vidal et al.

(10) Patent No.: US 6,837,908 B2
(45) Date of Patent: Jan. 4, 2005

(54) 2,5-DIAMINOPYRIDINE OXIDATION BASES FOR THE DYEING OF KERATIN FIBRES

(75) Inventors: Laurent Vidal, Paris (FR); Aziz Fadli, Chelles (FR)

(73) Assignee: L'Oreal S.A., Paris (FR)

( * ) Notice: Subject to any disclaimer, the term of this patent is extended or adjusted under 35 U.S.C. 154(b) by 225 days.

(21) Appl. No.: 10/293,328

(22) Filed: Nov. 14, 2002

(65) Prior Publication Data

US 2003/0163876 A1 Sep. 4, 2003

(30) Foreign Application Priority Data

Nov. 14, 2001 (FR) .............................................. 01 14717

(51) Int. Cl.⁷ ................................................ A61K 7/13
(52) U.S. Cl. ...................... 8/405; 8/406; 8/408; 8/409; 8/410; 8/411; 8/421; 8/568; 8/602; 546/249; 546/250
(58) Field of Search ........................... 8/405, 406, 409, 8/410, 411, 421, 568, 602; 546/249, 250

(56) References Cited

U.S. PATENT DOCUMENTS

| | | | | |
|---|---|---|---|---|
| 3,359,168 A | 12/1967 | Brechner et al. | ............. | 167/88 |
| 4,003,699 A | 1/1977 | Rose et al. | ................... | 8/10.2 |
| 4,247,556 A | 1/1981 | von Bebenburg et al. | .. | 424/255 |
| 4,823,985 A | 4/1989 | Grollier et al. | ................ | 222/1 |
| 5,061,289 A | 10/1991 | Clausen et al. | ................ | 8/405 |
| 5,145,482 A | 9/1992 | Clausen et al. | ................ | 8/409 |
| 5,380,340 A | 1/1995 | Neunhoeffer et al. | .......... | 8/409 |
| 5,766,576 A | 6/1998 | Löwe et al. | ................... | 424/62 |
| 6,099,592 A | 8/2000 | Vidal et al. | ..................... | 8/409 |
| 6,099,593 A | 8/2000 | Terranova et al. | ............. | 8/409 |

FOREIGN PATENT DOCUMENTS

| | | | |
|---|---|---|---|
| DE | 23 59 399 | 6/1975 | |
| DE | 38 43 892 | 6/1990 | |
| DE | 41 33 957 | 4/1993 | |
| DE | 195 43 988 | 5/1997 | |
| EP | 0 303 878 | 2/1989 | |
| EP | 0 770 375 | 5/1997 | |
| FR | 1 546 317 | 11/1968 | |
| FR | 2 586 913 | 3/1987 | |
| FR | 2 733 749 | 11/1996 | |
| FR | 2 750 048 | 12/1997 | |
| GB | 1 026 978 | 4/1966 | |
| GB | 1153196 | * 6/1966 | ............. D06P/8/08 |
| GB | 1 153 196 | 5/1969 | |
| JP | 2-19576 | 1/1990 | |
| JP | 5-163124 | 6/1993 | |
| WO | WO 88/07527 | 10/1988 | |
| WO | WO 94/08969 | 4/1994 | |
| WO | WO 94/08970 | 4/1994 | |
| WO | WO 96/15765 | 5/1996 | |

OTHER PUBLICATIONS

Donald L. Bussolotti et al., "A New Route to 6–Substituted 2,3–Diaminopyridines," Tetrahedron Letters, vol. 32, No. 45, 1991, pp. 6503–6506.
Chemical Abstracts Service, Columbus, Ohio, US, Database Accession No. 98:126033, XP002209523, 1983.
Chemical Abstracts Service, Columbus, Ohio, US, CAS RN 259683–18–6, XP002209524, no date.
Database WPI, Section Ch, Week 199954, Derwent Publications Ltd., London, GB; AN 1999–622717, XP002209525, 1999.
English language Derwent Abstract of EP 0 770 375, May 2, 1997.
English language Derwent Abstract of JP 2–19576, Jan. 23, 1990.
English language Derwent Abstract of JP 5–163124, Jun. 29, 1993.
Co–pending Application No. 10/291,481; Title: Use of an Extract of *Myrsine Africana* in Oxidation Dyeing for Dyeing Keratin Fibres Inventor(s): Béatrice Belcour–Castro et al. U.S. Filing Date: Nov. 14, 2002.

* cited by examiner

*Primary Examiner*—Yogendra N. Gupta
*Assistant Examiner*—Eisa Elhilo
(74) *Attorney, Agent, or Firm*—Finnegan, Henderson, Farabow, Garrett & Dunner LLP

(57) ABSTRACT

Dyeing compositions for the dyeing of keratin fibers comprising at least one oxidation base chosen from formula (I), as defined herein and addition salts thereof. The use of the compositions for the dyeing of keratin fibers. Dyeing processes employing the compositions. Novel 2,5-diaminopyridine compounds and addition salts thereof and their use as oxidation bases.

29 Claims, No Drawings

2,5-DIAMINOPYRIDINE OXIDATION BASES FOR THE DYEING OF KERATIN FIBRES

This disclosure relates to dyeing compositions for the dyeing of keratin fibres comprising at least one oxidation base of the 2,5-diaminopyridine type chosen from formula (I), as defined herein. This disclosure relates to the use of the compositions for the dyeing of keratin fibres. This disclosure further relates to dyeing processes employing the compositions. This disclosure also relates to 2,5-diaminopyridine compounds and their use as oxidation bases.

It is well-known to dye keratin fibres, such as human hair, with dyeing compositions comprising oxidation dye precursors, also known as oxidation bases, such as ortho- or para-phenylenediamine, ortho- or para-aminophenols and heterocyclic compounds. These oxidation bases may be colourless or weakly coloured compounds that, in combination with oxidizing substances, can give rise to coloured compounds by an oxidative coupling process.

It is well-known that the hues obtained with these oxidation bases can be varied by combining them with couplers or colouring modifiers. Colouring modifiers may be chosen, for example, from aromatic meta-diamines, meta-aminophenols, meta-diphenols, and certain heterocyclic compounds, such as indole compounds.

The variety of the molecules employed as oxidation bases and couplers makes it possible, for example, to obtain a rich palette of colours.

The "permanent" colouring using these oxidation dyes should satisfy a number of requirements. For example, oxidation dyes should be without a toxicological disadvantage. Oxidation dyes should, for example, make it possible to obtain hues with the desired intensity. They should behave well, for example, when exposed to external agents, such as light, bad weather, washing, permanent waving, perspiration and rubbing.

The dyes should be able to, for example, cover white hair. The oxidation dyes should be, for example, as unselective as possible, e.g., cause the fewest differences in colouring along the same keratin fiber, which may be sensitized (e.g., damaged) to varying degrees between its tip and its root.

It is already known to use 2,5-diaminopyridine as oxidation bases in hair dyeing compositions. For example, French Patent No. FR 1 546 317 discloses a process for dyeing the hair using a composition comprising pyridine derivatives substituted in the 2 position by an optionally substituted amino group or an alkoxy group, wherein other positions of the pyridine ring may be optionally substituted by one or two hydroxyl, amino or alkyl radicals, the alkyl radical optionally being substituted by a hydroxyl, an amino or a methoxy radical. One example of a pyridine derivative disclosed therein is 2,3,6-triaminopyridine. These pyridine derivatives are employed in an oxidation process, wherein oxidation is provided by aqueous hydrogen peroxide solution in the presence of an aqueous alkaline solution. According to this document, the composition comprising these pyridine derivatives reacts for ten hours before being applied to human hair. The dyes resulting from the ten-hour oxidation reaction are used. The process has at least the disadvantage, for example, of being highly impractical due to the time necessary to carry it out. Furthermore, the fastnesses of the hair colourings obtained using these diaminopyridine may be inferior, for example, to the fastness obtained conventionally with "oxidation" dyeing and the hues may exhibit very little variety. U.S. Pat. No. 3,359,168 discloses the use of 2,3,6-triaminopyridine as an oxidation base for the oxidation dyeing of hair. These compositions give green colourings which are intense but unstable to light. Dyeing compositions comprising, as oxidation base(s), 2,5-diaminopyridine unsubstituted on the pyridine ring are disclosed, for example, in Patent Nos. GO 1 026 978 and GO 1 153 196.

An embodiment provides, for example, novel dyeing compositions for the dyeing of keratin fibers that do not exhibit at least one disadvantage found in the prior art. An embodiment, for example, provides compositions that may exhibit powerful, not very selective and resistant colourings while being capable of generating intense colourings in varied hues, such as basic hues.

In another new embodiment, a dyeing composition comprises, in a medium acceptable for dyeing, at least one oxidation base chosen from formula (I), e.g., a 2,5-diaminopyridine derivative, and the addition salts thereof:

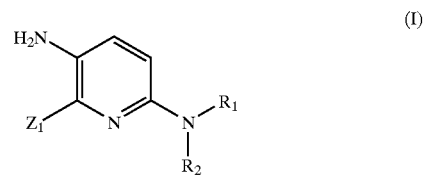

(I)

wherein
- $Z_1$ is chosen from $OR_3$ and $NR_4R_5$ radicals,
- $R_1$, $R_2$, $R_4$ and $R_5$, independently of one another, may be chosen from a hydrogen atom, $C_1$–$C_6$ alkyl, $C_2$–$C_6$ (poly)aminoalkyl, $C_2$–$C_6$ (poly)alkylamino alkyl, $C_2$–$C_6$ amino hydroxyalkyl, $C_2$–$C_6$ acylaminoalkyl, $C_2$–$C_6$ alkoxyalkyl, $C_2$–$C_6$ hydroxy alkoxyalkyl, $C_2$–$C_6$ amino alkoxyalkyl, $C_2$–$C_6$ (poly)hydroxyalkyl, $C_2$–$C_6$ carboxylalkyl and $C_2$–$C_6$ sulphoalkyl radicals;
- $R_1$ and $R_2$ and/or $R_4$ and $R_5$, independently of one another, may form, together with the nitrogen atom to which they are attached, a saturated heterocycle comprising from 5 to 8 ring members optionally substituted by at least one radical chosen from halogen atoms, amino, (di)alkylamino, hydroxyl, carboxyl, carboxamido, alkylsulphonylamino, acetamido and alkoxy radicals, and $C_1$–$C_6$ alkyl radicals optionally substituted by at least one radical chosen from hydroxyl, amino, (di)alkylamino, alkoxy, hydroxyalkoxy, aminoalkoxy, carboxyl, carboxamido, sulphonamido and sulpho radicals. The heterocycle may comprise at least one heteroatom chosen from oxygen, nitrogen (optionally substituted) and sulphur. The heterocycle may comprise an $SO_2$ group. But the heterocycle does not comprise a peroxide bond or a diazo or nitroso radical;
- $R_3$ is chosen from linear and branched $C_1$–$C_6$ alkyl radicals, which may be substituted by at least one radical chosen from hydroxyl, amino, $C_1$–$C_3$ mono- and dialkylamino radicals, whose alkyl part may be optionally substituted by at least one radical chosen from hydroxyl, amino, $C_1$–$C_2$ alkoxyalkoxy, and carboxyl radicals.

The at least one oxidation base chosen from formula (I) is not chosen from 2,3,6-triaminopyridine and the addition salts thereof.

This composition may, for example, make it possible to obtain a coloring that may exhibit greater fastness to shampooing or to light and/or a colouring that may have a better chromaticity.

In another new embodiment, a composition may be used, for example, in dyeing keratin fibers, such as human hair.

Another embodiment relates, for example, to a dyeing process employing a composition.

As used herein, the term "alkyl" means linear and branched radicals, such as methyl, ethyl, n-propyl, isopropyl, butyl, and so forth. An alkoxy radical is, for example, an alkyl-O radical, wherein the alkyl has the same definition as before. A halogen, for example, is chosen from Cl, Br and I.

The (poly)aminoalkyl radicals may be chosen from alkyl radicals substituted by at least one amino group and may be optionally substituted by at least one radical chosen from $C_1$–$C_4$ alkyls which may be, for example, substituted by at least one radical chosen, for example, from hydroxyl, amino, carboxyl and alkoxy radicals. The (poly)hydroxyalkyl radicals may be chosen from alkyl radicals substituted by at least one hydroxyl substituent.

In an embodiment, the at least one oxidation base chosen from formula (I) is chosen such that $R_3$ may be chosen, for example, from methyl, ethyl, hydroxyethyl, carboxymethyl and carboxyethyl radicals, such as the methyl radical.

In another new embodiment, the at least one oxidation base chosen from formula (I) may be chosen, for example, such that $R_1$, $R_2$, $R_4$ and $R_5$, independently of one another, may be chosen, for example, from $C_2$–$C_4$ (di)alkylamino alkyl, $C_2$–$C_4$ carboxyalkyl, $C_2$–$C_4$ sulphoalkyl, $C_2$–$C_4$ (poly)hydroxyalkyl and $C_2$–$C_4$ (poly)aminoalkyl radicals.

In another new embodiment, $R_1$ and $R_2$, and/or $R_4$ and $R_5$, independently of one another, may form, together with the nitrogen atom to which they are attached, a 5- to 8-membered heterocycle chosen from pyrrolidine, piperidine, homopiperidine, piperazine, homopiperazine and diazepane. The heterocycle may be substituted, for example, by at least one $C_1$–$C_4$ alkyl radical optionally substituted by at least one radical chosen from hydroxyl, amino, $C_1$–$C_2$ (di)alkylamino, carboxyl, carboxamido and sulphonamido radicals.

In another embodiment, $R_1$ and $R_2$ and/or $R_4$ and $R_5$, independently of one another, may form, together with the nitrogen atom to which they are attached, a heterocycle chosen from 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-(hydroxymethyl) pyrrolidine, 3,4-dihydroxy-2-(hydroxymethyl)pyrrolidine, 3-hydroxypyrrolidine, 3,4-dihydroxypyrrolidine, 3-aminopyrrolidine, 3-(methylamino)pyrrolidine, 4-amino-3-hydroxypyrrolidine, 3-hydroxy-4-[(2-hydroxyethyl)amino]pyrrolidine, 2,6-dimethylpiperidine, 2-carboxypiperidine, 2-carboxamidopiperidine, 2-hydroxymethyl piperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, diazepane, N-methyldiazepane and N-(2-hydroxyethyl)diazepane.

For example, $R_1$ and $R_2$ and/or $R_4$ and $R_5$, independently of one another, may form, together with the nitrogen atom to which they are attached, a heterocycle chosen from pyrrolidine, 3-hydroxypyrrolidine, 3-aminopyrrolidine, 3-acetamidopyrrolidine, 3-(methylsulphonylamino) pyrrolidine, pyrrolidine-2-carboxylic acid, 3-hydroxypyrrolidine-2-carboxylic acid, piperidine, hydroxypiperidine, homopiperidine, diazepane, N-methylhomopiperazine and N-(β-hydroxyethyl) homopiperazine.

The at least one oxidation base chosen from formula (I) may be chosen, for example, from:

2-methoxy-6-(pyrrolidin-1-yl)-3-aminopyridine,
1-(5-amino-6-methoxypyridin-2-yl)pyrrolidin-3-ol,
3-amino-2-methoxy-6-(morpholin-4-yl)pyridine,
3-amino-2-methoxy-6-(piperidin-1-yl)pyridine,
6-N,N-(2-hydroxyethyl)-methyl)amino)-3-amino-2-methoxypyridine,
5,6-diamino-2-(pyrrolidin-1-yl)pyridine,
N-(5,6-diaminopyridin-2-yl)-3-hydroxypyrrolidine,
2,6-did(pyrrolidin-1-yl)-5-aminopyridine,
6-(pyrrolidin-1-yl)-2,3-diaminopyridine,
6-(3-hydroxypyrrolidin-1-yl)-2,3-diaminopyridine,
6-(3-aminopyrrolidin-1-yl)-2,3-diaminopyridine,
6-(3-acetamidopyrrolidin-1-yl)-2,3-diaminopyridine,
6-(3,4-dihydroxypyrrolidin-1-yl)-2,3-diaminopyridine,
6-(2-carboxypyrrolidin-1-yl)-2,3-diaminopyridine,
6-(2-carboxy-3-hydroxypyrrolidin-1-yl)-2,3-diaminopyridine,
6-(2-carboxy-4-hydroxypyrrolidin-1-yl)-2,3-diaminopyridine,
6-(2-(hydroxymethyl)pyrrolidin-1-yl)-2,3-diaminopyridine,
6-(2-hydroxymethyl-4-hydroxypyrrolidin-1-yl)-2,3-diaminopyridine,
6-(2-hydroxymethyl-2-hydroxypyrrolidin-1-yl)-2,3-diaminopyridine,
6-(2-carboxamidopyrrolidin-1-yl)-2,3-diaminopyridine,
6-(2-dimethylcarboxamidopyrrolidin-1-yl)-2,3-diaminopyridine,
6-(2-carboxamido-3-hydroxypyrrolidin-1-yl)-2,3-diaminopyridine,
6-(2-carboxamido-4-hydroxypyrrolidin-1-yl)-2,3-diaminopyridine,
6-(pyrrolidin-1-yl)-3-amino-2-methylaminopyridine,
6-(3-hydroxypyrrolidin-1-yl)-3-amino-2-methylaminopyridine,
6-(3-aminopyrrolidin-1-yl)-3-amino-2-methylaminopyridine,
6-(3-acetamidopyrrolidin-1-yl)-3-amino-2-methylaminopyridine,
6-(3,4-dihydroxypyrrolidin-1-yl)-3-amino-2-methylaminopyridine,
6-(2-carboxypyrrolidin-1-yl)-3-amino-2-methylaminopyridine,
6-(2-carboxy-3-hydroxypyrrolidin-1-yl)-3-amino-2-methylaminopyridine, 6-(2-carboxy-4-hydroxypyrrolidin-1-yl)-3-amino-2-methylaminopyridine,
6-(2-(hydroxymethyl)pyrrolidin-1-yl)-3-amino-2-methylaminopyridine,
6-(2-hydroxymethyl-4-hydroxypyrrolidin-1-yl)-3-amino-2-methylaminopyridine,
6-(2-hydroxymethyl-2-hydroxypyrrolidin-1-yl)-3-amino-2-methylaminopyridine,
6-(2-carboxamidopyrrolidin-1-yl)-3-amino-2-methylaminopyridine,
6-(2-dimethylcarboxamidopyrrolidin-1-yl)-3-amino-2-methylaminopyridine,
6-(2-carboxamido-3-hydroxypyrrolidin-1-yl)-3-amino-2-methylaminopyridine,
6-(2-carboxamido-4-hydroxypyrrolidin-1-yl)-3-amino-2-methylaminopyridine,
6-(pyrrolidin-1-yl)-3-amino-2-ethylaminopyridine,
6-(3-hydroxypyrrolidin-1-yl)-3-amino-2-ethylaminopyridine,
6-(3-aminopyrrolidin-1-yl)-3-amino-2-ethylaminopyridine, 6-(3-acetamidopyrrolidin-1-yl)-3-amino-2-ethylaminopyridine,
6-(3,4-dihydroxypyrrolidin-1-yl)-3-amino-2-ethylaminopyridine,
6-(2-carboxypyrrolidin-1-yl)-3-amino-2-ethylaminopyridine,
6-(2-carboxy-3-hydroxypyrrolidin-1-yl)-3-amino-2-ethylaminopyridine,
6-(2-carboxy-4-hydroxypyrrolidin-1-yl)-3-amino-2-ethylaminopyridine,
6-(2-(hydroxymethyl)pyrrolidin-1-yl)-3-amino-2-ethylaminopyridine,
6-(2-hydroxymethyl-4-hydroxypyrrolidin-1-yl)-3-amino-2-ethylaminopyridine,
6-(2-hydroxymethyl-2-hydroxypyrrolidin-1-yl)-3-amino-2-ethylaminopyridine,
6-(2-carboxamidopyrrolidin-1-yl)-3-amino-2-ethylaminopyridine,
6-(2-dimethylcarboxamidopyrrolidin-1-yl)-3-amino-2-ethylaminopyridine,
6-(2-carboxamido-3-hydroxypyrrolidin-1-yl)-3-amino-2-ethylaminopyridine,
6-(2-carboxamido-4-hydroxypyrrolidin-1-yl)-3-amino-2-ethylaminopyridine,
6-(pyrrolidin-1-yl)-3-amino-2-(2-hydroxyethylamino)pyridine,
6-(3-hydroxypyrrolidin-1-yl)-3-amino-2-(2-hydroxyethylamino)pyridine,
6-(3-aminopyrrolidin-1-yl)-3-amino-2-(2-hydroxyethylamino)pyridine,
6-(3-acetamidopyrrolidin-1-yl)-3-amino-2-(2-hydroxyethylamino)pyridine,
6-(3,4-dihydroxypyrrolidin-1-yl)-3-amino-2-(2-hydroxyethylamino)pyridine,
6-(2-carboxypyrrolidin-1-yl)-3-amino-2-(2-hydroxyethylamino)pyridine,
6-(2-carboxy-3-hydroxypyrrolidin-1-yl)-3-amino-2-(2-hydroxyethylamino)pyridine,
6-(2-carboxy-4-hydroxypyrrolidin-1-yl)-3-amino-2-(2-hydroxyethylamino)pyridine,
6-(2-(hydroxymethyl)pyrrolidin-1-yl)-3-amino-2-(2-hydroxyethylamino)pyridine,
6-(2-hydroxymethyl-4-hydroxypyrrolidin-1-yl)-3-amino-2-(2-hydroxyethylamino)pyridine,
6-(2-hydroxymethyl-2-hydroxypyrrolidin-1-yl)-3-amino-2-(2-hydroxyethylamino)pyridine,
6-(2-carboxamidopyrrolidin-1-yl)-3-amino-2-(2-hydroxyethylamino)pyridine,
6-(2-dimethylcarboxamidopyrrolidin-1-yl)-3-amino-2-(2-hydroxyethylamino)pyridine,
6-(2-carboxamido-3-hydroxypyrrolidin-1-yl)-3-amino-2-(2-hydroxyethylamino)pyridine,
6-(2-carboxamido-4-hydroxypyrrolidin-1-yl)-3-aminopyridine,
6-(pyrrolidin-1-yl)-3-amino-2-(2-aminoethylamino)pyridine,
6-(3-hydroxypyrrolidin-1-yl)-3-amino-2-(2-aminoethylamino)pyridine,
6-(3-aminopyrrolidin-1-yl)-3-amino-2-(2-aminoethylamino)pyridine,
6-(3-acetamidopyrrolidin-1-yl)-3-amino-2-(2-aminoethylamino)pyridine,
6-(3,4-dihydroxypyrrolidin-1-yl)-3-amino-2-(2-aminoethylamino)pyridine,
6-(2-carboxypyrrolidin-1-yl)-3-amino-2-(2-aminoethylamino)pyridine,
6-(2-carboxy-3-hydroxypyrrolidin-1-yl)-3-amino-2-(2-aminoethylamino)pyridine,
6-(2-carboxy-4-hydroxypyrrolidin-1-yl)-3-amino-2-(2-aminoethylamino)pyridine,
6-(2-(hydroxymethyl)pyrrolidin-1-yl)-3-amino-2-(2-aminoethylamino)pyridine,
6-(2-hydroxymethyl-4-hydroxypyrrolidin-1-yl)-3-amino-2-(2-aminoethylamino)pyridine,
6-(2-hydroxymethyl-2-hydroxypyrrolidin-1-yl)-3-amino-2-(2-aminoethylamino)pyridine,
6-(2-carboxamidopyrrolidin-1-yl)-3-amino-2-(2-aminoethylamino)pyridine,
6-(2-dimethylcarboxamidopyrrolidin-1-yl)-3-amino-2-(2-aminoethylamino)pyridine,
6-(2-carboxamido-3-hydroxypyrrolidin-1-yl)-3-amino-2-(2-aminoethylamino)pyridine,
6-(2-carboxamido-4-hydroxypyrrolidin-1-yl)-3-amino-2-(2-aminoethylamino)pyridine,
6-(pyrrolidin-1-yl)-3-amino-2-(2-acetamidoethylamino)pyridine,
6-(3-hydroxypyrrolidin-1-yl)-3-amino-2-(2-acetamidoethylamino)pyridine,
6-(3-aminopyrrolidin-1-yl)-3-amino-2-(2-acetamidoethylamino)pyridine,
6-(3-acetamidopyrrolidin-1-yl)-3-amino-2-(2-acetamidoethylamino)pyridine,
6-(3,4-dihydroxypyrrolidin-1-yl)-3-amino-2-(2-acetamidoethylamino)pyridine,
6-(2-carboxypyrrolidin-1-yl)-3-amino-2-(2-acetamidoethylamino)pyridine,
6-(2-carboxy-3-hydroxypyrrolidin-1-yl)-3-amino-2-(2-acetamidoethylamino)pyridine,
6-(2-carboxy-4-hydroxypyrrolidin-1-yl)-3-amino-2-(2-acetamidoethylamino)pyridine,
6-(2-(hydroxymethyl)pyrrolidin-1-yl)-3-amino-2-(2-acetamidoethylamino)pyridine,
6-(2-hydroxymethyl-4-hydroxypyrrolidin-1-yl)-3-amino-2-(2-acetamidoethylamino)pyridine,
6-(2-hydroxymethyl-2-hydroxypyrrolidin-1-yl)-3-amino-2-(2-acetamidoethylamino)pyridine,
6-(2-carboxamidopyrrolidin-1-yl)-3-amino-2-(2-acetamidoethylamino)pyridine,
6-(2-dimethylcarboxamidopyrrolidin-1-yl)-3-amino-2-(2-acetamidoethylamino)pyridine,
6-(2-carboxamido-3-hydroxypyrrolidin-1-yl)-3-amino-2-(2-acetamidoethylamino)pyridine,
6-(2-carboxamido-4-hydroxypyrrolidin-1-yl)-3-amino-2-(2-acetamidoethylamino)pyridine,
6-(pyrrolidin-1-yl)-3-amino-2-(pyrrolidin-1-yl)pyridine,
6-(3-hydroxypyrrolidin-1-yl)-3-amino-2-(pyrrolidin-1-yl)pyridine,
6-(3-aminopyrrolidin-1-yl)-3-amino-2-(pyrrolidin-1-yl)pyridine,
6-(3-acetamidopyrrolidin-1-yl)-3-amino-2-(pyrrolidin-1-yl)pyridine,
6-(3,4-dihydroxypyrrolidin-1-yl)-3-amino-2-(pyrrolidin-1-yl)pyridine,
6-(2-carboxypyrrolidin-1-yl)-3-amino-2-(pyrrolidin-1-yl)pyridine,
6-(2-carboxy-3-hydroxypyrrolidin-1-yl)-3-amino-2-(pyrrolidin-1-yl)pyridine,
6-(2-carboxy-4-hydroxypyrrolidin-1-yl)-3-amino-2-(pyrrolidin-1-yl)pyridine,
6-(2-(hydroxymethyl)pyrrolidin-1-yl)-3-amino-2-(pyrrolidin-1-yl)pyridine,
6-(2-hydroxymethyl-4-hydroxypyrrolidin-1-yl)-3-amino-2-(pyrrolidin-1-yl)pyridine,
6-(2-hydroxymethyl-2-hydroxypyrrolidin-1-yl)-3-amino-2-(pyrrolidin-1-yl)pyridine, 6-(2-carboxamidopyrrolidin-1-yl)-3-amino-2-(pyrrolidin-1-yl)pyridine,
6-(2-dimethylcarboxamidopyrrolidin-1-yl)-3-amino-2-(pyrrolidin-1-yl)pyridine,
6-(2-carboxamido-3-hydroxypyrrolidin-1-yl)-3-amino-2-(pyrrolidin-1-yl)pyridine,
6-(2-carboxamido-4-hydroxypyrrolidin-1-yl)-3-amino-2-(pyrrolidin-1-yl)pyridine,
6-(pyrrolidin-1-yl)-3-amino-2-(3-hydroxypyrrolidin-1-yl)pyridine,
6-(3-hydroxypyrrolidin-1-yl)-3-amino-2-(3-hydroxypyrrolidin-1-yl)pyridine,
6-(3-aminopyrrolidin-1-yl)-3-amino-2-(3-hydroxypyrrolidin-1-yl)pyridine,
6-(3-acetamidopyrrolidin-1-yl)-3-amino-2-(3-hydroxypyrrolidin-1-yl)pyridine,
6-(3,4-dihydroxypyrrolidin-1-yl)-3-amino-2-(3-hydroxypyrrolidin-1-yl)pyridine,
6-(2-carboxypyrrolidin-1-yl)-3-amino-2-(3-hydroxypyrrolidin-1-yl)pyridine,
6-(2-carboxy-3-hydroxypyrrolidin-1-yl)-3-amino-2-(3-hydroxypyrrolidin-1-yl)pyridine,
6-(2-carboxy-4-hydroxypyrrolidin-1-yl)-3-amino-2-(3-hydroxypyrrolidin-1-yl)pyridine,
6-(2-(hydroxymethyl)pyrrolidin-1-yl)-3-amino-2-(3-hydroxypyrrolidin-1-yl)pyridine,
6-(2-hydroxymethyl-4-hydroxypyrrolidin-1-yl)-3-amino-2-(3-hydroxypyrrolidin-1-yl)pyridine,
6-(2-hydroxymethyl-2-hydroxypyrrolidin-1-yl)-3-amino-2-(3-hydroxypyrrolidin-1-yl)pyridine,
6-(2-carboxamidopyrrolidin-1-yl)-3-amino-2-(3-hydroxypyrrolidin-1-yl)pyridine,
6-(2-dimethylcarboxamidopyrrolidin-1-yl)-3-amino-2-(3-hydroxypyrrolidin-1-yl)pyridine,
6-(2-carboxamido-3-hydroxypyrrolidin-1-yl)-3-amino-2-(3-hydroxypyrrolidin-1-yl)pyridine,
6-(2-carboxamido-4-hydroxypyrrolidin-1-yl)-3-amino-2-(3-hydroxypyrrolidin-1-yl)pyridine,
6-(pyrrolidin-1-yl)-3-amino-2-(2-carboxypyrrolidin-1-yl)pyridine,
6-(3-hydroxypyrrolidin-1-yl)-3-amino-2-(2-carboxypyrrolidin-1-yl)pyridine,
6-(3-aminopyrrolidin-1-yl)-3-amino-2-(2-carboxypyrrolidin-1-yl)pyridine,
6-(3-acetamidopyrrolidin-1-yl)-3-amino-2-(2-carboxypyrrolidin-1-yl)pyridine,
6-(3,4-dihydroxypyrrolidin-1-yl)-3-amino-2-(2-carboxypyrrolidin-1-yl)pyridine,
6-(2-carboxypyrrolidin-1-yl)-3-amino-2-(2-carboxypyrrolidin-1-yl)pyridine,
6-(2-carboxy-3-hydroxypyrrolidin-1-yl)-3-amino-2-(2-carboxypyrrolidin-1-yl)pyridine,
6-(2-carboxy-4-hydroxypyrrolidin-1-yl)-3-amino-2-(2-carboxypyrrolidin-1-yl)pyridine,
6-(2-(hydroxymethyl)pyrrolidin-1-yl)-3-amino-2-(2-carboxypyrrolidin-1-yl)pyridine,
6-(2-hydroxymethyl-4-hydroxypyrrolidin-1-yl)-3-amino-2-(2-carboxypyrrolidin-1-yl)pyridine,
6-(2-hydroxymethyl-2-hydroxypyrrolidin-1-yl)-3-amino-2-(2-carboxypyrrolidin-1-yl)pyridine,
6-(2-carboxamidopyrrolidin-1-yl)-3-amino-2-(2-carboxypyrrolidin-1-yl)pyridine,
6-(2-dimethylcarboxamidopyrrolidin-1-yl)-3-amino-2-(2-carboxypyrrolidin-1-yl)pyridine,
6-(2-carboxamido-3-hydroxypyrrolidin-1-yl)-3-amino-2-(2-carboxypyrrolidin-1-yl)pyridine,
6-(2-carboxamido-4-hydroxypyrrolidin-1-yl)-3-amino-2-(2-carboxypyrrolidin-1-yl)pyridine,
6-(pyrrolidin-1-yl)-3-amino-2-(2-(hydroxymethyl)pyrrolidin-1-yl)pyridine,
6-(3-hydroxypyrrolidin-1-yl)-3-amino-2-(2-(hydroxymethyl)pyrrolidin-1-yl)pyridine,
6-(3-aminopyrrolidin-1-yl)-3-amino-2-(2-(hydroxymethyl)pyrrolidin-1-yl)pyridine,
6-(3-acetamidopyrrolidin-1-yl)-3-amino-2-(2-(hydroxymethyl)pyrrolidin-1-yl)pyridine,
6-(3,4-dihydroxypyrrolidin-1-yl)-3-amino-2-(2-(hydroxymethyl)pyrrolidin-1-yl)pyridine,
6-(2-carboxypyrrolidin-1-yl)-3-amino-2-(2-(hydroxymethyl)pyrrolidin-1-yl)pyridine,
6-(2-carboxy-3-hydroxypyrrolidin-1-yl)-3-amino-2-(2-(hydroxymethyl)pyrrolidin-1-yl)pyridine,
6-(2-carboxy-4-hydroxypyrrolidin-1-yl)-3-amino-2-(2-(hydroxymethyl)pyrrolidin-1-yl)pyridine,
6-(2-(hydroxymethyl)pyrrolidin-1-yl)-3-amino-2-(2-(hydroxymethyl)pyrrolidin-1-yl)pyridine,
6-(2-hydroxymethyl-4-hydroxypyrrolidin-1-yl)-3-amino-2-(2-(hydroxymethyl)pyrrolidin-1-yl)pyridine,
6-(2-hydroxymethyl-2-hydroxypyrrolidin-1-yl)-3-amino-2-(2-(hydroxymethyl)pyrrolidin-1-yl)pyridine,
6-(2-carboxamidopyrrolidin-1-yl)-3-amino-2-(2-(hydroxymethyl)pyrrolidin-1-yl)pyridine,
6-(2-dimethylcarboxamidopyrrolidin-1-yl)-3-amino-2-(2-(hydroxymethyl)pyrrolidin-1-yl)pyridine,
6-(2-carboxamido-3-hydroxypyrrolidin-1-yl)-3-amino-2-(2-(hydroxymethyl)pyrrolidin-1-yl)pyridine,
6-(2-carboxamido-4-hydroxypyrrolidin-1-yl)-3-amino-2-(2-(hydroxymethyl)pyrrolidin-1-yl)pyridine,
6-(pyrrolidin-1-yl)-3-amino-2-(2-carboxamidopyrrolidin-1-yl)pyridine,
6-(3-hydroxypyrrolidin-1-yl)-3-amino-2-(2-carboxamidopyrrolidin-1-yl)pyridine,
6-(3-aminopyrrolidin-1-yl)-3-amino-2-(2-carboxamidopyrrolidin-1-yl)pyridine,
6-(3-acetamidopyrrolidin-1-yl)-3-amino-2-(2-carboxamidopyrrolidin-1-yl)pyridine,
6-(3,4-dihydroxypyrrolidin-1-yl)-3-amino-2-(2-carboxamidopyrrolidin-1-yl)pyridine,
6-(2-carboxypyrrolidin-1-yl)-3-amino-2-(2-carboxamidopyrrolidin-1-yl)pyridine,
6-(2-carboxy-3-hydroxypyrrolidin-1-yl)-3-amino-2-(2-carboxamidopyrrolidin-1-yl)pyridine,
6-(2-carboxy-4-hydroxypyrrolidin-1-yl)-3-amino-2-(2-carboxamidopyrrolidin-1-yl)pyridine,
6-(2-(hydroxymethyl)pyrrolidin-1-yl)-3-amino-2-(2-carboxamidopyrrolidin-1-yl)pyridine,
6-(2-hydroxymethyl-4-hydroxypyrrolidin-1-yl)-3-amino-2-(2-carboxamidopyrrolidin-1-yl)pyridine,
6-(2-hydroxymethyl-2-hydroxypyrrolidin-1-yl)-3-amino-2-(2-carboxamidopyrrolidin-1-yl)pyridine,
6-(2-carboxamidopyrrolidin-1-yl)-3-amino-2-(2-carboxamidopyrrolidin-1-yl)pyridine,
6-(2-dimethylcarboxamidopyrrolidin-1-yl)-3-amino-2-(2-carboxamidopyrrolidin-1-yl)pyridine,
6-(2-carboxamido-3-hydroxypyrrolidin-1-yl)-3-amino-2-(2-carboxamidopyrrolidin-1-yl)pyridine,
6-(2-carboxamido-4-hydroxypyrrolidin-1-yl)-3-amino-2-(2-carboxamidopyrrolidin-1-yl)pyridine,
6-(pyrrolidin-1-yl)-3-amino-2-dimethylaminopyridine,
6-(3-hydroxypyrrolidin-1-yl)-3-amino-2-dimethylaminopyridine,
6-(3-aminopyrrolidin-1-yl)-3-amino-2-dimethylaminopyridine,
6-(3-acetamidopyrrolidin-1-yl)-3-amino-2-dimethylaminopyridine, 6-(3,4-dihydroxypyrrolidin-1-yl)-3-amino-2-dimethylaminopyridine,
6-(2-carboxypyrrolidin-1-yl)-3-amino-2-dimethylaminopyridine,
6-(2-carboxy-3-hydroxypyrrolidin-1-yl)-3-amino-2-dimethylaminopyridine,
6-(2-carboxy-4-hydroxypyrrolidin-1-yl)-3-amino-2-dimethylaminopyridine,
6-(2-(hydroxymethyl)pyrrolidin-1-yl)-3-amino-2-dimethylaminopyridine,
6-(2-hydroxymethyl-4-hydroxypyrrolidin-1-yl)-3-amino-2-dimethylaminopyridine,
6-(2-hydroxymethyl-2-hydroxypyrrolidin-1-yl)-3-amino-2-dimethylaminopyridine,
6-(2-carboxamidopyrrolidin-1-yl)-3-amino-2-dimethylaminopyridine,
6-(2-dimethylcarboxamidopyrrolidin-1-yl)-3-amino-2-dimethylaminopyridine,
6-(2-carboxamido-3-hydroxypyrrolidin-1-yl)-3-amino-2-dimethylaminopyridine,
6-(2-carboxamido-4-hydroxypyrrolidin-1-yl)-3-amino-2-dimethylaminopyridine,
6-(pyrrolidin-1-yl)-3-amino-2-[methyl(2-hydroxyethyl)amino]pyridine,
6-(3-hydroxypyrrolidin-1-yl)-3-amino-2-[methyl(2-hydroxyethyl)amino]pyridine,
6-(3-aminopyrrolidin-1-yl)-3-amino-2-[methyl(2-hydroxyethyl)amino]pyridine,
6-(3-acetamidopyrrolidin-1-yl)-3-amino-2-[methyl(2-hydroxyethyl)amino]pyridine,
6-(3,4-dihydroxypyrrolidin-1-yl)-3-amino-2-[methyl(2-hydroxyethyl)amino]pyridine,
6-(2-carboxypyrrolidin-1-yl)-3-amino-2-[methyl(2-hydroxyethyl)amino]pyridine,
6-(2-carboxy-3-hydroxypyrrolidin-1-yl)-3-amino-2-[methyl(2-hydroxyethyl)amino]pyridine,
6-(2-carboxy-4-hydroxypyrrolidin-1-yl)-3-amino-2-[methyl(2-hydroxyethyl)amino]pyridine,
6-(2-(hydroxymethyl)pyrrolidin-1-yl)-3-amino-2-[methyl(2-hydroxyethyl)amino]pyridine,
6-(2-hydroxymethyl-4-hydroxypyrrolidin-1-yl)-3-amino-2-[methyl(2-hydroxyethyl)amino]pyridine,
6-(2-hydroxymethyl-2-hydroxypyrrolidin-1-yl)-3-amino-2-[methyl(2-hydroxyethyl)amino]pyridine,
6-(2-carboxamidopyrrolidin-1-yl)-3-amino-2-[methyl(2-hydroxyethyl)amino]pyridine,
6-(2-dimethylcarboxamidopyrrolidin-1-yl)-3-amino-2-[methyl(2-hydroxyethyl)amino]pyridine,
6-(2-carboxamido-3-hydroxypyrrolidin-1-yl)-3-amino-2-[methyl(2-hydroxyethyl)amino]pyridine,
6-(2-carboxamido-4-hydroxypyrrolidin-1-yl)-3-amino-2-[methyl(2-hydroxyethyl)amino]pyridine,
6-(pyrrolidin-1-yl)-3-amino-2-[methyl(2-aminoethyl)amino]pyridine,
6-(3-hydroxypyrrolidin-1-yl)-3-amino-2-[methyl(2-aminoethyl)amino]pyridine,
6-(3-aminopyrrolidin-1-yl)-3-amino-2-[methyl(2-aminoethyl)amino]pyridine,
6-(3-acetamidopyrrolidin-1-yl)-3-amino-2-[methyl(2-aminoethyl)amino]pyridine,
6-(3,4-dihydroxypyrrolidin-1-yl)-3-amino-2-[methyl(2-aminoethyl)amino]pyridine,
6-(2-carboxypyrrolidin-1-yl)-3-amino-2-[methyl(2-aminoethyl)amino]pyridine,
6-(2-carboxy-3-hydroxypyrrolidin-1-yl)-3-amino-2-[methyl(2-aminoethyl)amino]pyridine,
6-(2-carboxy-4-hydroxypyrrolidin-1-yl)-3-amino-2-[methyl(2-aminoethyl)amino]pyridine,
6-(2-(hydroxymethyl)pyrrolidin-1-yl)-3-amino-2-[methyl(2-aminoethyl)amino]pyridine,
6-(2-hydroxymethyl-4-hydroxypyrrolidin-1-yl)-3-amino-2-[methyl(2-aminoethyl)amino]pyridine,
6-(2-hydroxymethyl-2-hydroxypyrrolidin-1-yl)-3-amino-2-[methyl(2-aminoethyl)amino]pyridine,
6-(2-carboxamidopyrrolidin-1-yl)-3-amino-2-[methyl(2-aminoethyl)amino]pyridine,
6-(2-dimethylcarboxamidopyrrolidin-1-yl)-3-amino-2-[methyl(2-aminoethyl)amino]pyridine,
6-(2-carboxamido-3-hydroxypyrrolidin-1-yl)-3-amino-2-[methyl(2-aminoethyl)amino]pyridine,
6-(2-carboxamido-4-hydroxypyrrolidin-1-yl)-3-amino-2-[methyl(2-aminoethyl)amino]pyridine,
6-(pyrrolidin-1-yl)-3-amino-2-[methyl(2-acetamidoethyl)amino]pyridine,
6-(3-hydroxypyrrolidin-1-yl)-3-amino-2-[methyl(2-acetamidoethyl)amino]pyridine,
6-(3-aminopyrrolidin-1-yl)-3-amino-2-[methyl(2-acetamidoethyl)amino]pyridine,
6-(3-acetamidopyrrolidin-1-yl)-3-amino-2-[methyl(2-acetamidoethyl)amino]pyridine,
6-(3,4-dihydroxypyrrolidin-1-yl)-3-amino-2-[methyl(2-acetamidoethyl)amino]pyridine,
6-(2-carboxypyrrolidin-1-yl)-3-amino-2-[methyl(2-acetamidoethyl)amino]pyridine,
6-(2-carboxy-3-hydroxypyrrolidin-1-yl)-3-amino-2-[methyl(2-acetamidoethyl)amino]pyridine,
6-(2-carboxy-4-hydroxypyrrolidin-1-yl)-3-amino-2-[methyl(2-acetamidoethyl)amino]pyridine,
6-(2-(hydroxymethyl)pyrrolidin-1-yl)-3-amino-2-[methyl(2-acetamidoethyl)amino]pyridine,
6-(2-hydroxymethyl-4-hydroxypyrrolidin-1-yl)-3-amino-2-[methyl(2-acetamidoethyl)amino]pyridine,
6-(2-hydroxymethyl-2-hydroxypyrrolidin-1-yl)-3-amino-2-[methyl(2-acetamidoethyl)amino]pyridine,
6-(2-carboxamidopyrrolidin-1-yl)-3-amino-2-[methyl(2-acetamidoethyl)amino]pyridine,
6-(2-dimethylcarboxamidopyrrolidin-1-yl)-3-amino-2-[methyl(2-acetamidoethyl)amino]pyridine,
6-(2-carboxamido-3-hydroxypyrrolidin-1-yl)-3-amino-2-[methyl(2-acetamidoethyl)amino]pyridine,
6-(2-carboxamido-4-hydroxypyrrolidin-1-yl)-3-amino-2-[methyl(2-acetamidoethyl)amino]pyridine,
6-(pyrrolidin-1-yl)-3-amino-2-methoxypyridine,
6-(3-hydroxypyrrolidin-1-yl)-3-amino-2-methoxypyridine,
6-(3-aminopyrrolidin-1-yl)-3-amino-2-methoxypyridine,
6-(3-acetamidopyrrolidin-1-yl)-3-amino-2-methoxypyridine,
6-(3,4-dihydroxypyrrolidin-1-yl)-3-amino-2-methoxypyridine,
6-(2-carboxypyrrolidin-1-yl)-3-amino-2-methoxypyridine,
6-(2-carboxy-3-hydroxypyrrolidin-1-yl)-3-amino-2-methoxypyridine,
6-(2-carboxy-4-hydroxypyrrolidin-1-yl)-3-amino-2-methoxypyridine,
6-(2-(hydroxymethyl)pyrrolidin-1-yl)-3-amino-2-methoxypyridine,
6-(2-hydroxymethyl-4-hydroxypyrrolidin-1-yl)-3-amino-2-methoxypyridine,
6-(2-hydroxymethyl-2-hydroxypyrrolidin-1-yl)-3-amino-2-methoxypyridine,
6-(2-carboxamidopyrrolidin-1-yl)-3-amino-2-methoxypyridine,
6-(2-dimethylcarboxamidopyrrolidin-1-yl)-3-amino-2-methoxypyridine,
6-(2-carboxamido-3-hydroxypyrrolidin-1-yl)-3-amino-2-methoxypyridine, 6-(2-carboxamido-4-hydroxypyrrolidin-1-yl)-3-amino-2-methoxypyridine,
6-(pyrrolidin-1-yl)-3-amino-2-(2-hydroxyethyloxy)pyridine,
6-(3-hydroxypyrrolidin-1-yl)-3-amino-2-(2-hydroxyethyloxy)pyridine,
6-(3-aminopyrrolidin-1-yl)-3-amino-2-(2-hydroxyethyloxy)pyridine,
6-(3-acetamidopyrrolidin-1-yl)-3-amino-2-(2-hydroxyethyloxy)pyridine,
6-(3,4-dihydroxypyrrolidin-1-yl)-3-amino-2-(2-hydroxyethyloxy)pyridine,
6-(2-carboxypyrrolidin-1-yl)-3-amino-2-(2-hydroxyethyloxy)pyridine,
6-(2-carboxy-3-hydroxypyrrolidin-1-yl)-3-amino-2-(2-hydroxyethyloxy)pyridine,
6-(2-carboxy-4-hydroxypyrrolidin-1-yl)-3-amino-2-(2-hydroxyethyloxy)pyridine,
6-(2-(hydroxymethyl)pyrrolidin-1-yl)-3-amino-2-(2-hydroxyethyloxy)pyridine,
6-(2-hydroxymethyl-4-hydroxypyrrolidin-1-yl)-3-amino-2-(2-hydroxyethyloxy)pyridine,
6-(2-hydroxymethyl-2-hydroxypyrrolidin-1-yl)-3-amino-2-(2-hydroxyethyloxy)pyridine,
6-(2-carboxamidopyrrolidin-1-yl)-3-amino-2-(2-hydroxyethyloxy)pyridine,
6-(2-dimethylcarboxamidopyrrolidin-1-yl)-3-amino-2-(2-hydroxyethyloxy)pyridine,
6-(2-carboxamido-3-hydroxypyrrolidin-1-yl)-3-amino-2-(2-hydroxyethyloxy)pyridine,
6-(2-carboxamido-4-hydroxypyrrolidin-1-yl)-3-amino-2-(2-hydroxyethyloxy)pyridine,
6-(pyrrolidin-1-yl)-3-amino-2-ethoxypyridine,
6-(3-hydroxypyrrolidin-1-yl)-3-amino-2-ethoxypyridine,
6-(3-aminopyrrolidin-1-yl)-3-amino-2-ethoxypyridine,
6-(3-acetamidopyrrolidin-1-yl)-3-amino-2-ethoxypyridine,
6-(3,4-dihydroxypyrrolidin-1-yl)-3-amino-2-ethoxypyridine,
6-(2-carboxypyrrolidin-1-yl)-3-amino-2-ethoxypyridine,
6-(2-carboxy-3-hydroxypyrrolidin-1-yl)-3-amino-2-ethoxypyridine,
6-(2-carboxy-4-hydroxypyrrolidin-1-yl)-3-amino-2-ethoxypyridine,
6-(2-(hydroxymethyl)pyrrolidin-1-yl)-3-amino-2-ethoxypyridine,
6-(2-hydroxymethyl-4-hydroxypyrrolidin-1-yl)-3-amino-2-ethoxypyridine,
6-(2-hydroxymethyl-2-hydroxypyrrolidin-1-yl)-3-amino-2-ethoxypyridine,
6-(2-carboxamidopyrrolidin-1-yl)-3-amino-2-ethoxypyridine,
6-(2-dimethylcarboxamidopyrrolidin-1-yl)-3-amino-2-ethoxypyridine,
6-(2-carboxamido-3-hydroxypyrrolidin-1-yl)-3-amino-2-ethoxypyridine,
6-(2-carboxamido-4-hydroxypyrrolidin-1-yl)-3-amino-2-ethoxypyridine,
and addition salts thereof.

The at least one oxidation base chosen from formula (I) may be chosen, for example, from:

2-methoxy-6-(pyrrolidin-1-yl)-3-aminopyridine,
5,6-diamino-2-(pyrrolidin-1-yl)pyridine,
N-(5,6-diaminopyridin-2-yl)-3-hydroxypyrrolidine,
2,6-did(pyrrolidin-1-yl)-5-aminopyridine,
and addition salts thereof.

In another embodiment, the composition may, for example, comprise at least one additional oxidation base used in oxidation dyeing, other than the at least one oxidation base chosen from formula (I). The at least one additional oxidation base may be chosen, for example, from para-phenylenediamine, bisphenylalkylenediamines, para-aminophenols, ortho-aminophenols, heterocyclic bases other than those described above, and addition salts thereof.

The para-phenylenediamine may be chosen, for example, from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl, β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 3-hydroxy-1-(4'-amino-phenyl)pyrrolidine, 2-thienyl-para-phenylenediamine, 2-(β-hydroxyethylamino)-5-aminotoluene, and addition salts thereof.

The para-phenylenediamine may be chosen, for example, from para-phenylenediamine, para-tolylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine, and theacid addition salts thereof. The bisphenylalkylenediamines may be chosen, for example, from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and addition salts thereof.

The para-aminophenols may be chosen, for example, from para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-(2-aminomethyl)phenol, 4-amino-2-[(β-hydroxyethyl)aminomethyl]phenol, 4-amino-2-fluorophenol, and addition salts thereof.

The ortho-aminophenols may be chosen, for example, from 2-aminophenol, 2-amino-5-methylphenol, 2-amino-6-methylphenol, 5-acetamido-2-aminophenol, and addition salts thereof.

The heterocyclic bases may be chosen, for example, from pyridine derivatives other than those chosen from formula (I), pyrimidine derivatives, and pyrazole derivatives.

The pyridine derivatives may be chosen, for example, from the compounds disclosed, for example, in Patent Nos.

GO 1 026 978 and GO 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and addition salts thereof.

The pyrimidine derivatives may be chosen, for example, from the compounds disclosed, for example, in Patent Nos. DE 2 359 399, JP 88-169 571, JP 05 163 124 and EP 0 770 375 and Patent Application No. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives, which may be chosen, for example, from those mentioned in Patent Application No. FR-A-2 750 048, such as pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethypyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]-pyrimidine-3,7-diamine, 3-amino-5-methyl-7-(imidazolylpropylamino)pyrazolo[1,5-a]pyrimidine, and addition salts thereof and tautomeric forms thereof, where a tautomeric equilibrium exists.

The pyrazole derivatives may be chosen, for example, from the compounds disclosed in Patent Nos. DE 3 843 892 and DE 4 133 957 and Patent Application Nos. WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methypyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl)amino-1-methylpyrazole, and addition salts thereof.

The at least one oxidation base chosen from formula (I) and/or the at least one additional oxidation base may be present in an amount ranging, for example, from 0.001 to 10% by weight, relative to the total weight of the dyeing composition, such as from 0.005 to 6%.

The composition may comprise, for example, at least one coupler chosen from couplers used in the dyeing of keratin fibers. The at least one coupler may be chosen, for example, from meta-phenylenediamine, meta-aminophenols, meta-diphenols, naphthalene couplers, heterocyclic couplers, and addition salts thereof.

The at least one coupler may be chosen, for example, from 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-(β-hydroxyethylamino)-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and addition salts thereof.

In another new embodiment, the at least one coupler may be present in an amount ranging, for example, from 0.001 to 10% by weight, relative to the total weight of the dyeing composition, such as from 0.005 to 6%.

The addition salts of the at least one oxidation base and of the at least one coupler may be chosen, for example, from acid addition salts, such as hydrochlorides, hydrobromides, sulphates, citrates, succinates, tartrates, lactates, tosylates, benzene-sulphonates, phosphates and acetates, and base addition salts, such as sodium hydroxide, potassium hydroxide, ammonia, amines and alkanolamines.

In another embodiment, the dyeing composition may comprise, for example, at least one direct dye chosen, for example, from nitro dyes of the benzene series, cationic direct dyes, azo direct dyes and methine direct dyes.

The medium acceptable for dyeing, e.g., the dyeing vehicle, may be chosen, for example, from water and mixtures of water and at least one organic solvent. The at least one organic solvent may, for example, dissolve the compounds that are not sufficiently soluble in water. The at least one organic solvent may be chosen, for example, from lower $C_1$–$C_4$ alkanols, such as ethanol and isopropanol; polyols and polyol ethers, such as 2-butoxyethanol, propylene glycol, propylene glycol monomethyl ether, diethylene glycol monoethyl ether and diethylene glycol monomethyl ether; and aromatic alcohols, such as benzyl alcohol or phenoxyethanol.

The at least one organic solvent may be present in an amount ranging, for example, from 1 to 40% by weight, relative to the total weight of the dyeing composition, such as from 5 to 30% by weight.

The dyeing composition may comprise, for example, at least one adjuvant chosen from, for example, adjuvants used in hair dyeing compositions, such as anionic, cationic, nonionic, amphoteric and zwitterionic surface-active agents, anionic, cationic, nonionic, amphoteric and zwitterionic polymers, inorganic and organic thickening agents, such as anionic, cationic, nonionic and amphoteric associative polymer thickeners, antioxidants, penetration agents, sequestering agents, fragrances, buffers, dispersing agents, conditioning agents, such as, for example, volatile and nonvolatile and modified and unmodified silicones, film-forming agents, ceramides, preservatives and opacifying agents.

The at least one adjuvant may be present in an amount ranging, for example, from 0.01 to 20% by weight, relative to the total weight of the composition.

A person of ordinary skill in the art may choose at least one optional additional compound so that the oxidation dyeing composition is not, or not substantially, changed by the envisaged addition.

The pH of the dyeing composition may range, for example, from 3 to 12, such as from 5 to 11. The pH may be adjusted, for example, using at least one acidifying agent and/or at least one basifying agent. The at least one acidifying agent and/or at least one basifying agent may be chosen, for example, from acidifying and basifying agents used in dyeing keratin fibres and conventional buffer systems.

The acidifying agents may be chosen, for example, from inorganic and organic acids, such as hydrochloric acid, orthophosphoric acid, sulphuric acid, carboxylic acids, such as acetic acid, tartaric acid, citric acid and lactic acid, and sulphonic acids.

The basifying agents may be chosen, for example, from ammonia, alkaline carbonates, alkanolamines, such as mono-, did- and triethanolamines, and their derivatives, sodium hydroxide, potassium hydroxide and the compounds chosen from formula (II):

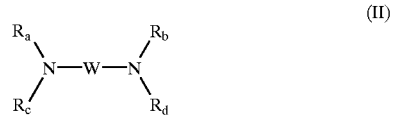

(II)

wherein W is chosen from propylene residues optionally substituted by at least one radical chosen from a hydroxyl radical and $C_1$–$C_4$ alkyl radicals, and $R_a$, $R_b$, $R_c$ and $R_d$, which may be identical or different, are chosen from a hydrogen atom and $C_1$–$C_4$ alkyl and $C_1$–$C_4$ hydroxyalkyl radicals.

The dyeing composition may be in various forms, such as in a form chosen from liquids, creams and gels and any other form acceptable for dyeing of keratin fibres, such as human hair.

In another new embodiment, the dyeing composition may be applied to keratin fibres, and the colour may be developed using at least one oxidizing agent. The colour may be developed, for example, at acidic, neutral or alkaline pH. The at least one oxidizing agent may be mixed with the dyeing composition at the time of use. An oxidizing composition comprising the at least one oxidizing agent may, for example, be applied simultaneously with, or sequentially to, the dyeing composition.

In an embodiment, the dyeing composition may be mixed, for example, at the time of use, with an oxidizing composition comprising, in a medium acceptable for dyeing, at least one oxidizing agent, wherein the at least one oxidizing agent is present in an amount sufficient to develop a colouring. The mixture obtained may be subsequently applied to the keratin fibers. After a leave-in time ranging from 3 to 50 minutes, such as from 5 to 30 minutes, the keratin fibres may be optionally rinsed, optionally washed with a shampoo, optionally rinsed again and then optionally dried.

The at least one oxidizing agent may be chosen, for example, from oxidizing agents used in oxidation dyeing of keratin fibres, such as hydrogen peroxide, urea hydrogen peroxide, alkali metal bromates, persalts, such as perborates and persulphates, peracids and oxidase enzymes, such as peroxidases, 2-electron oxidoreductases, such as uricases, and 4-electron oxygenases, such as laccases. The at least one oxidizing agent may, for example, be hydrogen peroxide.

The oxidizing composition may comprise, for example, at least one adjuvant chosen, for example, from adjuvants used in hair dyeing compositions, such as those adjuvants described above.

The pH of the oxidizing composition comprising the at least one oxidizing agent may be, for example, such that after mixing with the dyeing composition, the pH of the resulting composition applied to the keratin fibres ranges from 3 to 12, such as from 5 to 11. The pH may be adjusted, for example, using at least one acidifying agent and/or at least one basifying agent chosen, for example, from acidifying and basifying agents used in dyeing keratin fibers.

A ready-to-use composition applied to the keratin fibers may be in various forms, such as in the form of liquids, creams or gels or in any other form acceptable for dyeing keratin fibers, such as human hair.

Another new embodiment comprises a multi-compartment device or kit, wherein a first compartment comprises the dyeing composition defined above and a second compartment comprises an oxidizing composition. This device may be equipped, for example, with a means allowing the desired mixture to be delivered to the hair, such as the devices disclosed in French Patent No. FR 2 586 913.

Another new embodiment comprises at least one colored product obtained by the oxidative coupling of a dyeing composition, such as a composition comprising at least one oxidation base chosen from formula (I), optionally in the presence of at least one coupler and/or in the presence of at least one additional oxidation base, in the presence of at least one oxidizing agent.

The at least one colored product may be, for example, in the form of a pigment. The at least one colored product may be used, for example, as a direct dye for the direct dyeing of the hair or, alternatively, may be incorporated, for example, in cosmetic products such as, for example, make-up products.

An oxidation base chosen from formula (I), such as 2,3,6-triaminopyridine, may be disclosed, for example, in Patent Nos. FR 1 546 317 and U.S. Pat. No. 3,359,168. At least one other oxidation base chosen from formula (I) is novel and comprises another new embodiment. The at least one other oxidation base may be chosen, for example, from 2,5-diaminopyridine derivatives chosen from formula (I'):

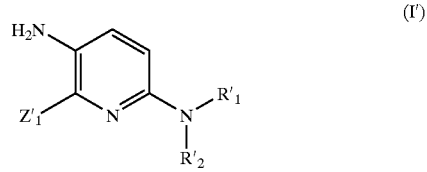

(I')

wherein
  $Z'_1$ is chosen from $OR'_3$ and $NR'_4R'_5$ radicals;
  $R'_1$, $R'_2$, $R'_4$ and $R'_5$, independently of one another, may be chosen from a hydrogen atom, $C_2$–$C_6$ (poly)aminoalkyl, $C_2$–$C_6$ (poly)alkylamino alkyl, $C_2$–$C_6$ amino hydroxyalkyl, $C_2$–$C_6$ acylaminoalkyl, $C_2$–$C_6$ alkoxyalkyl, $C_2$–$C_6$ hydroxy alkoxyalkyl, $C_2$–$C_6$ amino alkoxyalkyl, $C_2$–$C_6$ (poly)hydroxyalkyl, $C_2$–$C_6$ carboxylalkyl and $C_2$–$C_6$ sulphoalkyl radicals;
  $R'_1$ and $R'_2$, and/or $R'_4$ and $R'_5$, independently of one another, may form, together with the nitrogen atom to which they are attached, a saturated heterocycle comprising from 5 to 8 ring members optionally substituted by at least one radical chosen from halogen atoms, amino, (di)alkylamino, hydroxyl, carboxyl, carboxamido and alkoxy radicals, and $C_1$–$C_6$ alkyl radicals optionally substituted by at least one radical chosen from hydroxyl, amino, (di)alkylamino, alkoxy, hydroxyalkoxy, aminoalkoxy, carboxyl and sulpho radicals. The heterocycle may optionally comprise at least one additional heteroatom chosen from oxygen, optionally substituted nitrogen, and sulphur. The heterocycle may optionally comprise an $SO_2$ group. The heterocycle does not comprise a peroxide bond or a diazo or nitroso radical;

$R'_3$ is chosen from linear and branched $C_1$–$C_6$ alkyl radicals optionally substituted by at least one radical chosen from hydroxyl, amino, $C_1$–$C_3$ mono- and dialkylamino radicals, wherein the alkyl parts may be optionally substituted by at least one radical chosen from hydroxyl, amino, $C_1$–$C_2$ alkoxyalkoxy, and carboxyl radicals.

The at least one 2,5-diaminopyridine derivative chosen from formula (I') is not chosen from 2,3,6-triaminopyridine, 6-(4-morpholinyl)-2,3-diaminopyridine, 6-(1-piperidinyl-2, 3-diaminopyridine and 2,6-di-4-morpholinyl-3-aminopyridine, and addition salts thereof.

The at least one 2,5-diaminopyridine derivative chosen from formula (I') may be chosen, for example, from:

2-methoxy-6-(pyrrolidin-1-yl)-3-aminopyridine,
1-(5-amino-6-methoxypyridin-2-yl)pyrrolidin-3-ol,
3-amino-2-methoxy-6-(morpholin-4-yl)pyridine,
3-amino-2-methoxy-6-(piperidin-1-yl)pyridine,
6-N,N-(2-hydroxyethyl)-methyl)amino)-3-amino-2-methoxypyridine,
5,6-diamino-2-(pyrrolidin-1-yl)pyridine,
N-(5,6-diaminopyridin-2-yl)-3-hydroxypyrrolidine,
2,6-did(pyrrolidin-1-yl)-5-aminopyridine,
6-(pyrrolidin-1-yl)-2,3-diaminopyridine,
6-(3-hydroxypyrrolidin-1-yl)-2,3-diaminopyridine,
6-(3-aminopyrrolidin-1-yl)-2,3-diaminopyridine,
6-(3-acetamidopyrrolidin-1-yl)-2,3-diaminopyridine,
6-(3,4-dihydroxypyrrolidin-1-yl)-2,3-diaminopyridine,
6-(2-carboxypyrrolidin-1-yl)-2,3-diaminopyridine,
6-(2-carboxy-3-hydroxypyrrolidin-1-yl)-2,3-diaminopyridine,
6-(2-carboxy-4-hydroxypyrrolidin-1-yl)-2,3-diaminopyridine,
6-(2-(hydroxymethyl)pyrrolidin-1-yl)-2,3-diaminopyridine,
6-(2-hydroxymethyl-4-hydroxypyrrolidin-1-yl)-2,3-diaminopyridine,
6-(2-hydroxymethyl-2-hydroxypyrrolidin-1-yl)-2,3-diaminopyridine,
6-(2-carboxamidopyrrolidin-1-yl)-2,3-diaminopyridine,
6-(2-dimethylcarboxamidopyrrolidin-1-yl)-2,3-diaminopyridine,
6-(2-carboxamido-3-hydroxypyrrolidin-1-yl)-2,3-diaminopyridine,
6-(2-carboxamido-4-hydroxypyrrolidin-1-yl)-2,3-diaminopyridine,
6-(pyrrolidin-1-yl)-3-amino-2-methylaminopyridine,
6-(3-hydroxypyrrolidin-1-yl)-3-amino-2-methylaminopyridine,
6-(3-aminopyrrolidin-1-yl)-3-amino-2-methylaminopyridine,
6-(3-acetamidopyrrolidin-1-yl)-3-amino-2-methylaminopyridine,
6-(3,4-dihydroxypyrrolidin-1-yl)-3-amino-2-methylaminopyridine,
6-(2-carboxypyrrolidin-1-yl)-3-amino-2-methylaminopyridine,
6-(2-carboxy-3-hydroxypyrrolidin-1-yl)-3-amino-2-methylaminopyridine,
6-(2-carboxy-4-hydroxypyrrolidin-1-yl)-3-amino-2-methylaminopyridine,
6-(2-(hydroxymethyl)pyrrolidin-1-yl)-3-amino-2-methylaminopyridine,
6-(2-hydroxymethyl-4-hydroxypyrrolidin-1-yl)-3-amino-2-methylaminopyridine,
6-(2-hydroxymethyl-2-hydroxypyrrolidin-1-yl)-3-amino-2-methylaminopyridine,
6-(2-carboxamidopyrrolidin-1-yl)-3-amino-2-methylaminopyridine,
6-(2-dimethylcarboxamidopyrrolidin-1-yl)-3-amino-2-methylaminopyridine,
6-(2-carboxamido-3-hydroxypyrrolidin-1-yl)-3-amino-2-methylaminopyridine,
6-(2-carboxamido-4-hydroxypyrrolidin-1-yl)-3-amino-2-methylaminopyridine,
6-(pyrrolidin-1-yl)-3-amino-2-ethylaminopyridine,
6-(3-hydroxypyrrolidin-1-yl)-3-amino-2-ethylaminopyridine,
6-(3-aminopyrrolidin-1-yl)-3-amino-2-ethylaminopyridine,
6-(3-acetamidopyrrolidin-1-yl)-3-amino-2-ethylaminopyridine,
6-(3,4-dihydroxypyrrolidin-1-yl)-3-amino-2-ethylaminopyridine,
6-(2-carboxypyrrolidin-1-yl)-3-amino-2-ethylaminopyridine,
6-(2-carboxy-3-hydroxypyrrolidin-1-yl)-3-amino-2-ethylaminopyridine,
6-(2-carboxy-4-hydroxypyrrolidin-1-yl)-3-amino-2-ethylaminopyridine,
6-(2-(hydroxymethyl)pyrrolidin-1-yl)-3-amino-2-ethylaminopyridine,
6-(2-hydroxymethyl-4-hydroxypyrrolidin-1-yl)-3-amino-2-ethylaminopyridine,
6-(2-hydroxymethyl-2-hydroxypyrrolidin-1-yl)-3-amino-2-ethylaminopyridine,
6-(2-carboxamidopyrrolidin-1-yl)-3-amino-2-ethylaminopyridine,
6-(2-dimethylcarboxamidopyrrolidin-1-yl)-3-amino-2-ethylaminopyridine,
6-(2-carboxamido-3-hydroxypyrrolidin-1-yl)-3-amino-2-ethylaminopyridine,
6-(2-carboxamido-4-hydroxypyrrolidin-1-yl)-3-amino-2-ethylaminopyridine,
6-(pyrrolidin-1-yl)-3-amino-2-(2-hydroxyethylamino)pyridine,
6-(3-hydroxypyrrolidin-1-yl)-3-amino-2-(2-hydroxyethylamino)pyridine,
6-(3-aminopyrrolidin-1-yl)-3-amino-2-(2-hydroxyethylamino)pyridine,
6-(3-acetamidopyrrolidin-1-yl)-3-amino-2-(2-hydroxyethylamino)pyridine,
6-(3,4-dihydroxypyrrolidin-1-yl)-3-amino-2-(2-hydroxyethylamino)pyridine,
6-(2-carboxypyrrolidin-1-yl)-3-amino-2-(2-hydroxyethylamino)pyridine,
6-(2-carboxy-3-hydroxypyrrolidin-1-yl)-3-amino-2-(2-hydroxyethylamino)pyridine,
6-(2-carboxy-4-hydroxypyrrolidin-1-yl)-3-amino-2-(2-hydroxyethylamino)pyridine,
6-(2-(hydroxymethyl)pyrrolidin-1-yl)-3-amino-2-(2-hydroxyethylamino)pyridine,
6-(2-hydroxymethyl-4-hydroxypyrrolidin-1-yl)-3-amino-2-(2-hydroxyethylamino)pyridine,
6-(2-hydroxymethyl-2-hydroxypyrrolidin-1-yl)-3-amino-2-(2-hydroxyethylamino)pyridine,
6-(2-carboxamidopyrrolidin-1-yl)-3-amino-2-(2-hydroxyethylamino)pyridine,
6-(2-dimethylcarboxamidopyrrolidin-1-yl)-3-amino-2-(2-hydroxyethylamino)pyridine,
6-(2-carboxamido-3-hydroxypyrrolidin-1-yl)-3-amino-2-(2-hydroxyethylamino)pyridine,
6-(2-carboxamido-4-hydroxypyrrolidin-1-yl)-3-aminopyridine, 6-(pyrrolidin-1-yl)-3-amino-2-(2-aminoethylamino)pyridine,
6-(3-hydroxypyrrolidin-1-yl)-3-amino-2-(2-aminoethylamino)pyridine,
6-(3-aminopyrrolidin-1-yl)-3-amino-2-(2-aminoethylamino)pyridine,
6-(3-acetamidopyrrolidin-1-yl)-3-amino-2-(2-aminoethylamino)pyridine,
6-(3,4-dihydroxypyrrolidin-1-yl)-3-amino-2-(2-aminoethylamino)pyridine,
6-(2-carboxypyrrolidin-1-yl)-3-amino-2-(2-aminoethylamino)pyridine,
6-(2-carboxy-3-hydroxypyrrolidin-1-yl)-3-amino-2-(2-aminoethylamino)pyridine,
6-(2-carboxy-4-hydroxypyrrolidin-1-yl)-3-amino-2-(2-aminoethylamino)pyridine,
6-(2-(hydroxymethyl)pyrrolidin-1-yl)-3-amino-2-(2-aminoethylamino)pyridine,
6-(2-hydroxymethyl-4-hydroxypyrrolidin-1-yl)-3-amino-2-(2-aminoethylamino)pyridine,
6-(2-hydroxymethyl-2-hydroxypyrrolidin-1-yl)-3-amino-2-(2-aminoethylamino)pyridine,
6-(2-carboxamidopyrrolidin-1-yl)-3-amino-2-(2-aminoethylamino)pyridine,
6-(2-dimethylcarboxamidopyrrolidin-1-yl)-3-amino-2-(2-aminoethylamino)pyridine,
6-(2-carboxamido-3-hydroxypyrrolidin-1-yl)-3-amino-2-(2-aminoethylamino)pyridine,
6-(2-carboxamido-4-hydroxypyrrolidin-1-yl)-3-amino-2-(2-aminoethylamino)pyridine,
6-(pyrrolidin-1-yl)-3-amino-2-(2-acetamidoethylamino)pyridine,
6-(3-hydroxypyrrolidin-1-yl)-3-amino-2-(2-acetamidoethylamino)pyridine,
6-(3-aminopyrrolidin-1-yl)-3-amino-2-(2-acetamidoethylamino)pyridine,
6-(3-acetamidopyrrolidin-1-yl)-3-amino-2-(2-acetamidoethylamino)pyridine,
6-(3,4-dihydroxypyrrolidin-1-yl)-3-amino-2-(2-acetamidoethylamino)pyridine,
6-(2-carboxypyrrolidin-1-yl)-3-amino-2-(2-acetamidoethylamino)pyridine,
6-(2-carboxy-3-hydroxypyrrolidin-1-yl)-3-amino-2-(2-acetamidoethylamino)pyridine,
6-(2-carboxy-4-hydroxypyrrolidin-1-yl)-3-amino-2-(2-acetamidoethylamino)pyridine,
6-(2-(hydroxymethyl)pyrrolidin-1-yl)-3-amino-2-(2-acetamidoethylamino)pyridine,
6-(2-hydroxymethyl-4-hydroxypyrrolidin-1-yl)-3-amino-2-(2-acetamidoethylamino)pyridine,
6-(2-hydroxymethyl-2-hydroxypyrrolidin-1-yl)-3-amino-2-(2-acetamidoethylamino)pyridine,
6-(2-carboxamidopyrrolidin-1-yl)-3-amino-2-(2-acetamidoethylamino)pyridine,
6-(2-dimethylcarboxamidopyrrolidin-1-yl)-3-amino-2-(2-acetamidoethylamino)pyridine,
6-(2-carboxamido-3-hydroxypyrrolidin-1-yl)-3-amino-2-(2-acetamidoethylamino)pyridine,
6-(2-carboxamido-4-hydroxypyrrolidin-1-yl)-3-amino-2-(2-acetamidoethylamino)pyridine,
6-(pyrrolidin-1-yl)-3-amino-2-(pyrrolidin-1-yl)pyridine,
6-(3-hydroxypyrrolidin-1-yl)-3-amino-2-(pyrrolidin-1-yl)pyridine,
6-(3-aminopyrrolidin-1-yl)-3-amino-2-(pyrrolidin-1-yl)pyridine,
6-(3-acetamidopyrrolidin-1-yl)-3-amino-2-(pyrrolidin-1-yl)pyridine,
6-(3,4-dihydroxypyrrolidin-1-yl)-3-amino-2-(pyrrolidin-1-yl)pyridine,
6-(2-carboxypyrrolidin-1-yl)-3-amino-2-(pyrrolidin-1-yl)pyridine,
6-(2-carboxy-3-hydroxypyrrolidin-1-yl)-3-amino-2-(pyrrolidin-1-yl)pyridine,
6-(2-carboxy-4-hydroxypyrrolidin-1-yl)-3-amino-2-(pyrrolidin-1-yl)pyridine,
6-(2-(hydroxymethyl)pyrrolidin-1-yl)-3-amino-2-(pyrrolidin-1-yl)pyridine,
6-(2-hydroxymethyl-4-hydroxypyrrolidin-1-yl)-3-amino-2-(pyrrolidin-1-yl)pyridine,
6-(2-hydroxymethyl-2-hydroxypyrrolidin-1-yl)-3-amino-2-(pyrrolidin-1-yl)pyridine,
6-(2-carboxamidopyrrolidin-1-yl)-3-amino-2-(pyrrolidin-1-yl)pyridine,
6-(2-dimethylcarboxamidopyrrolidin-1-yl)-3-amino-2-(pyrrolidin-1-yl)pyridine,
6-(2-carboxamido-3-hydroxypyrrolidin-1-yl)-3-amino-2-(pyrrolidin-1-yl)pyridine,
6-(2-carboxamido-4-hydroxypyrrolidin-1-yl)-3-amino-2-(pyrrolidin-1-yl)pyridine,
6-(pyrrolidin-1-yl)-3-amino-2-(3-hydroxypyrrolidin-1-yl)pyridine,
6-(3-hydroxypyrrolidin-1-yl)-3-amino-2-(3-hydroxypyrrolidin-1-yl)pyridine,
6-(3-aminopyrrolidin-1-yl)-3-amino-2-(3-hydroxypyrrolidin-1-yl)pyridine,
6-(3-acetamidopyrrolidin-1-yl)-3-amino-2-(3-hydroxypyrrolidin-1-yl)pyridine,
6-(3,4-dihydroxypyrrolidin-1-yl)-3-amino-2-(3-hydroxypyrrolidin-1-yl)pyridine,
6-(2-carboxypyrrolidin-1-yl)-3-amino-2-(3-hydroxypyrrolidin-1-yl)pyridine,
6-(2-carboxy-3-hydroxypyrrolidin-1-yl)-3-amino-2-(3-hydroxypyrrolidin-1-yl)pyridine,
6-(2-carboxy-4-hydroxypyrrolidin-1-yl)-3-amino-2-(3-hydroxypyrrolidin-1-yl)pyridine,
6-(2-(hydroxymethyl)pyrrolidin-1-yl)-3-amino-2-(3-hydroxypyrrolidin-1-yl)pyridine,
6-(2-hydroxymethyl-4-hydroxypyrrolidin-1-yl)-3-amino-2-(3-hydroxypyrrolidin-1-yl)pyridine,
6-(2-hydroxymethyl-2-hydroxypyrrolidin-1-yl)-3-amino-2-(3-hydroxypyrrolidin-1-yl)pyridine,
6-(2-carboxamidopyrrolidin-1-yl)-3-amino-2-(3-hydroxypyrrolidin-1-yl)pyridine,
6-(2-dimethylcarboxamidopyrrolidin-1-yl)-3-amino-2-(3-hydroxypyrrolidin-1-yl)pyridine,
6-(2-carboxamido-3-hydroxypyrrolidin-1-yl)-3-amino-2-(3-hydroxypyrrolidin-1-yl)pyridine,
6-(2-carboxamido-4-hydroxypyrrolidin-1-yl)-3-amino-2-(3-hydroxypyrrolidin-1-yl)pyridine,
6-(pyrrolidin-1-yl)-3-amino-2-(2-carboxypyrrolidin-1-yl)pyridine,
6-(3-hydroxypyrrolidin-1-yl)-3-amino-2-(2-carboxypyrrolidin-1-yl)pyridine,
6-(3-aminopyrrolidin-1-yl)-3-amino-2-(2-carboxypyrrolidin-1-yl)pyridine,
6-(3-acetamidopyrrolidin-1-yl)-3-amino-2-(2-carboxypyrrolidin-1-yl)pyridine,
6-(3,4-dihydroxypyrrolidin-1-yl)-3-amino-2-(2-carboxypyrrolidin-1-yl)pyridine,
6-(2-carboxypyrrolidin-1-yl)-3-amino-2-(2-carboxypyrrolidin-1-yl)pyridine,
6-(2-carboxy-3-hydroxypyrrolidin-1-yl)-3-amino-2-(2-carboxypyrrolidin-1-yl)pyridine,
6-(2-carboxy-4-hydroxypyrrolidin-1-yl)-3-amino-2-(2-carboxypyrrolidin-1-yl)pyridine, 6-(2-(hydroxymethyl)pyrrolidin-1-yl)-3-amino-2-(2-carboxypyrrolidin-1-yl)pyridine,
6-(2-hydroxymethyl-4-hydroxypyrrolidin-1-yl)-3-amino-2-(2-carboxypyrrolidin-1-yl)pyridine,
6-(2-hydroxymethyl-2-hydroxypyrrolidin-1-yl)-3-amino-2-(2-carboxypyrrolidin-1-yl)pyridine,
6-(2-carboxamidopyrrolidin-1-yl)-3-amino-2-(2-carboxypyrrolidin-1-yl)pyridine,
6-(2-dimethylcarboxamidopyrrolidin-1-yl)-3-amino-2-(2-carboxypyrrolidin-1-yl)pyridine,
6-(2-carboxamido-3-hydroxypyrrolidin-1-yl)-3-amino-2-(2-carboxypyrrolidin-1-yl)pyridine,
6-(2-carboxamido-4-hydroxypyrrolidin-1-yl)-3-amino-2-(2-carboxypyrrolidin-1-yl)pyridine,
6-(pyrrolidin-1-yl)-3-amino-2-(2-hydroxymethyl)pyrrolidin-1-yl)pyridine,
6-(3-hydroxypyrrolidin-1-yl)-3-amino-2-(2-(hydroxymethyl)pyrrolidin-1-yl)pyridine,
6-(3-aminopyrrolidin-1-yl)-3-amino-2-(2-(hydroxymethyl)pyrrolidin-1-yl)pyridine,
6-(3-acetamidopyrrolidin-1-yl)-3-amino-2-(2-(hydroxymethyl)pyrrolidin-1-yl)pyridine,
6-(3,4-dihydroxypyrrolidin-1-yl)-3-amino-2-(2-(hydroxymethyl)pyrrolidin-1-yl)pyridine,
6-(2-carboxypyrrolidin-1-yl)-3-amino-2-(2-(hydroxymethyl)pyrrolidin-1-yl)pyridine,
6-(2-carboxy-3-hydroxypyrrolidin-1-yl)-3-amino-2-(2-(hydroxymethyl)pyrrolidin-1-yl)pyridine,
6-(2-carboxy-4-hydroxypyrrolidin-1-yl)-3-amino-2-(2-(hydroxymethyl)pyrrolidin-1-yl)pyridine,
6-(2-(hydroxymethyl)pyrrolidin-1-yl)-3-amino-2-(2-(hydroxymethyl)pyrrolidin-1-yl)pyridine,
6-(2-hydroxymethyl-4-hydroxypyrrolidin-1-yl)-3-amino-2-(2-(hydroxymethyl)pyrrolidin-1-yl)pyridine,
6-(2-hydroxymethyl-2-hydroxypyrrolidin-1-yl)-3-amino-2-(2-(hydroxymethyl)pyrrolidin-1-yl)pyridine,
6-(2-carboxamidopyrrolidin-1-yl)-3-amino-2-(2-(hydroxymethyl)pyrrolidin-1-yl)pyridine,
6-(2-dimethylcarboxamidopyrrolidin-1-yl)-3-amino-2-(2-(hydroxymethyl)pyrrolidin-1-yl)pyridine,
6-(2-carboxamido-3-hydroxypyrrolidin-1-yl)-3-amino-2-(2-(hydroxymethyl)pyrrolidin-1-yl)pyridine,
6-(2-carboxamido-4-hydroxypyrrolidin-1-yl)-3-amino-2-(2-(hydroxymethyl)pyrrolidin-1-yl)pyridine,
6-(pyrrolidin-1-yl)-3-amino-2-(2-carboxamidopyrrolidin-1-yl)pyridine,
6-(3-hydroxypyrrolidin-1-yl)-3-amino-2-(2-carboxamidopyrrolidin-1-yl)pyridine,
6-(3-aminopyrrolidin-1-yl)-3-amino-2-(2-carboxamidopyrrolidin-1-yl)pyridine,
6-(3-acetamidopyrrolidin-1-yl)-3-amino-2-(2-carboxamidopyrrolidin-1-yl)pyridine,
6-(3,4-dihydroxypyrrolidin-1-yl)-3-amino-2-(2-carboxamidopyrrolidin-1-yl)pyridine,
6-(2-carboxypyrrolidin-1-yl)-3-amino-2-(2-carboxamidopyrrolidin-1-yl)pyridine,
6-(2-carboxy-3-hydroxypyrrolidin-1-yl)-3-amino-2-(2-carboxamidopyrrolidin-1-yl)pyridine,
6-(2-carboxy-4-hydroxypyrrolidin-1-yl)-3-amino-2-(2-carboxamidopyrrolidin-1-yl)pyridine,
6-(2-(hydroxymethyl)pyrrolidin-1-yl)-3-amino-2-(2-carboxamidopyrrolidin-1-yl)pyridine,
6-(2-hydroxymethyl-4-hydroxypyrrolidin-1-yl)-3-amino-2-(2-carboxamidopyrrolidin-1-yl)pyridine,
6-(2-hydroxymethyl-2-hydroxypyrrolidin-1-yl)-3-amino-2-(2-carboxamidopyrrolidin-1-yl)pyridine,
6-(2-carboxamidopyrrolidin-1-yl)-3-amino-2-(2-carboxamidopyrrolidin-1-yl)pyridine,
6-(2-dimethylcarboxamidopyrrolidin-1-yl)-3-amino-2-(2-carboxamidopyrrolidin-1-yl)pyridine,
6-(2-carboxamido-3-hydroxypyrrolidin-1-yl)-3-amino-2-(2-carboxamidopyrrolidin-1-yl)pyridine,
6-(2-carboxamido-4-hydroxypyrrolidin-1-yl)-3-amino-2-(2-carboxamidopyrrolidin-1-yl)pyridine,
6-(pyrrolidin-1-yl)-3-amino-2-dimethylaminopyridine,
6-(3-hydroxypyrrolidin-1-yl)-3-amino-2-dimethylaminopyridine,
6-(3-aminopyrrolidin-1-yl)-3-amino-2-dimethylaminopyridine,
6-(3-acetamidopyrrolidin-1-yl)-3-amino-2-dimethylaminopyridine,
6-(3,4-dihydroxypyrrolidin-1-yl)-3-amino-2-dimethylaminopyridine,
6-(2-carboxypyrrolidin-1-yl)-3-amino-2-dimethylaminopyridine,
6-(2-carboxy-3-hydroxypyrrolidin-1-yl)-3-amino-2-dimethylaminopyridine,
6-(2-carboxy-4-hydroxypyrrolidin-1-yl)-3-amino-2-dimethylaminopyridine,
6-(2-(hydroxymethyl)pyrrolidin-1-yl)-3-amino-2-dimethylaminopyridine,
6-(2-hydroxymethyl-4-hydroxypyrrolidin-1-yl)-3-amino-2-dimethylaminopyridine,
6-(2-hydroxymethyl-2-hydroxypyrrolidin-1-yl)-3-amino-2-dimethylaminopyridine,
6-(2-carboxamidopyrrolidin-1-yl)-3-amino-2-dimethylaminopyridine,
6-(2-dimethylcarboxamidopyrrolidin-1-yl)-3-amino-2-dimethylaminopyridine,
6-(2-carboxamido-3-hydroxypyrrolidin-1-yl)-3-amino-2-dimethylaminopyridine,
6-(2-carboxamido-4-hydroxypyrrolidin-1-yl)-3-amino-2-dimethylaminopyridine,
6-(pyrrolidin-1-yl)-3-amino-2-[methyl(2-hydroxyethyl)amino]pyridine,
6-(3-hydroxypyrrolidin-1-yl)-3-amino-2-[methyl(2-hydroxyethyl)amino]pyridine,
6-(3-aminopyrrolidin-1-yl)-3-amino-2-[methyl(2-hydroxyethyl)amino]pyridine,
6-(3-acetamidopyrrolidin-1-yl)-3-amino-2-[methyl(2-hydroxyethyl)amino]pyridine,
6-(3,4-dihydroxypyrrolidin-1-yl)-3-amino-2-[methyl(2-hydroxyethyl)amino]pyridine,
6-(2-carboxypyrrolidin-1-yl)-3-amino-2-[methyl(2-hydroxyethyl)amino]pyridine,
6-(2-carboxy-3-hydroxypyrrolidin-1-yl)-3-amino-2-[methyl(2-hydroxyethyl)amino]pyridine,
6-(2-carboxy-4-hydroxypyrrolidin-1-yl)-3-amino-2-[methyl(2-hydroxyethyl)amino]pyridine,
6-(2-(hydroxymethyl)pyrrolidin-1-yl)-3-amino-2-[methyl(2-hydroxyethyl)amino]pyridine,
6-(2-hydroxymethyl-4-hydroxypyrrolidin-1-yl)-3-amino-2-[methyl(2-hydroxyethyl)amino]pyridine,
6-(2-hydroxymethyl-2-hydroxypyrrolidin-1-yl)-3-amino-2-[methyl(2-hydroxyethyl)amino]pyridine,
6-(2-carboxamidopyrrolidin-1-yl)-3-amino-2-[methyl(2-hydroxyethyl)amino]pyridine,
6-(2-dimethylcarboxamidopyrrolidin-1-yl)-3-amino-2-[methyl(2-hydroxyethyl)amino]pyridine,
6-(2-carboxamido-3-hydroxypyrrolidin-1-yl)-3-amino-2-[methyl(2-hydroxyethyl)amino]pyridine,
6-(2-carboxamido-4-hydroxypyrrolidin-1-yl)-3-amino-2-[methyl(2-hydroxyethyl)amino]pyridine,
6-(pyrrolidin-1-yl)-3-amino-2-[methyl(2-aminoethyl)amino]pyridine, 6-(3-hydroxypyrrolidin-1-yl)-3-amino-2-[methyl(2-aminoethyl)amino]pyridine,
6-(3-aminopyrrolidin-1-yl)-3-amino-2-[methyl(2-aminoethyl)amino]pyridine,
6-(3-acetamidopyrrolidin-1-yl)-3-amino-2-[methyl(2-aminoethyl)amino]pyridine,
6-(3,4-dihydroxypyrrolidin-1-yl)-3-amino-2-[methyl(2-aminoethyl)amino]pyridine,
6-(2-carboxypyrrolidin-1-yl)-3-amino-2-[methyl(2-aminoethyl)amino]pyridine,
6-(2-carboxy-3-hydroxypyrrolidin-1-yl)-3-amino-2-[methyl(2-aminoethyl)amino]pyridine,
6-(2-carboxy-4-hydroxypyrrolidin-1-yl)-3-amino-2-[methyl(2-aminoethyl)amino]pyridine,
6-(2-(hydroxymethyl)pyrrolidin-1-yl)-3-amino-2-[methyl(2-aminoethyl)amino]pyridine,
6-(2-hydroxymethyl-4-hydroxypyrrolidin-1-yl)-3-amino-2-[methyl(2-aminoethyl)amino]pyridine,
6-(2-hydroxymethyl-2-hydroxypyrrolidin-1-yl)-3-amino-2-[methyl(2-aminoethyl)amino]pyridine,
6-(2-carboxamidopyrrolidin-1-yl)-3-amino-2-[methyl(2-aminoethyl)amino]pyridine,
6-(2-dimethylcarboxamidopyrrolidin-1-yl)-3-amino-2-[methyl(2-aminoethyl)amino]pyridine,
6-(2-carboxamido-3-hydroxypyrrolidin-1-yl)-3-amino-2-[methyl(2-aminoethyl)amino]pyridine,
6-(2-carboxamido-4-hydroxypyrrolidin-1-yl)-3-amino-2-[methyl(2-aminoethyl)amino]pyridine,
6-(pyrrolidin-1-yl)-3-amino-2-[methyl(2-acetamidoethyl)amino]pyridine,
6-(3-hydroxypyrrolidin-1-yl)-3-amino-2-[methyl(2-acetamidoethyl)amino]pyridine,
6-(3-aminopyrrolidin-1-yl)-3-amino-2-[methyl(2-acetamidoethyl)amino]pyridine,
6-(3-acetamidopyrrolidin-1-yl)-3-amino-2-[methyl(2-acetamidoethyl)amino]pyridine,
6-(3,4-dihydroxypyrrolidin-1-yl)-3-amino-2-[methyl(2-acetamidoethyl)amino]pyridine,
6-(2-carboxypyrrolidin-1-yl)-3-amino-2-[methyl(2-acetamidoethyl)amino]pyridine,
6-(2-carboxy-3-hydroxypyrrolidin-1-yl)-3-amino-2-[methyl(2-acetamidoethyl)amino]pyridine,
6-(2-carboxy-4-hydroxypyrrolidin-1-yl)-3-amino-2-[methyl(2-acetamidoethyl)amino]pyridine,
6-(2-(hydroxymethyl)pyrrolidin-1-yl)-3-amino-2-[methyl(2-acetamidoethyl)amino]pyridine,
6-(2-hydroxymethyl-4-hydroxypyrrolidin-1-yl)-3-amino-2-[methyl(2-acetamidoethyl)amino]pyridine,
6-(2-hydroxymethyl-2-hydroxypyrrolidin-1-yl)-3-amino-2-[methyl(2-acetamidoethyl)amino]pyridine,
6-(2-carboxamidopyrrolidin-1-yl)-3-amino-2-[methyl(2-acetamidoethyl)amino]pyridine,
6-(2-dimethylcarboxamidopyrrolidin-1-yl)-3-amino-2-[methyl(2-acetamidoethyl)amino]pyridine,
6-(2-carboxamido-3-hydroxypyrrolidin-1-yl)-3-amino-2-[methyl(2-acetamidoethyl)amino]pyridine,
6-(2-carboxamido-4-hydroxypyrrolidin-1-yl)-3-amino-2-[methyl(2-acetamidoethyl)amino]pyridine,
6-(pyrrolidin-1-yl)-3-amino-2-methoxypyridine,
6-(3-hydroxypyrrolidin-1-yl)-3-amino-2-methoxypyridine,
6-(3-aminopyrrolidin-1-yl)-3-amino-2-methoxypyridine,
6-(3-acetamidopyrrolidin-1-yl)-3-amino-2-methoxypyridine,
6-(3,4-dihydroxypyrrolidin-1-yl)-3-amino-2-methoxypyridine,
6-(2-carboxypyrrolidin-1-yl)-3-amino-2-methoxypyridine,
6-(2-carboxy-3-hydroxypyrrolidin-1-yl)-3-amino-2-methoxypyridine,
6-(2-carboxy-4-hydroxypyrrolidin-1-yl)-3-amino-2-methoxypyridine,
6-(2-(hydroxymethyl)pyrrolidin-1-yl)-3-amino-2-methoxypyridine,
6-(2-hydroxymethyl-4-hydroxypyrrolidin-1-yl)-3-amino-2-methoxypyridine,
6-(2-hydroxymethyl-2-hydroxypyrrolidin-1-yl)-3-amino-2-methoxypyridine,
6-(2-carboxamidopyrrolidin-1-yl)-3-amino-2-methoxypyridine,
6-(2-dimethylcarboxamidopyrrolidin-1-yl)-3-amino-2-methoxypyridine,
6-(2-carboxamido-3-hydroxypyrrolidin-1-yl)-3-amino-2-methoxypyridine,
6-(2-carboxamido-4-hydroxypyrrolidin-1-yl)-3-amino-2-methoxypyridine,
6-(pyrrolidin-1-yl)-3-amino-2-(2-hydroxyethyloxy)pyridine,
6-(3-hydroxypyrrolidin-1-yl)-3-amino-2-(2-hydroxyethyloxy)pyridine,
6-(3-aminopyrrolidin-1-yl)-3-amino-2-(2-hydroxyethyloxy)pyridine,
6-(3-acetamidopyrrolidin-1-yl)-3-amino-2-(2-hydroxyethyloxy)pyridine,
6-(3,4-dihydroxypyrrolidin-1-yl)-3-amino-2-(2-hydroxyethyloxy)pyridine,
6-(2-carboxypyrrolidin-1-yl)-3-amino-2-(2-hydroxyethyloxy)pyridine,
6-(2-carboxy-3-hydroxypyrrolidin-1-yl)-3-amino-2-(2-hydroxyethyloxy)pyridine,
6-(2-carboxy-4-hydroxypyrrolidin-1-yl)-3-amino-2-(2-hydroxyethyloxy)pyridine,
6-(2-(hydroxymethyl)pyrrolidin-1-yl)-3-amino-2-(2-hydroxyethyloxy)pyridine,
6-(2-hydroxymethyl-4-hydroxypyrrolidin-1-yl)-3-amino-2-(2-hydroxyethyloxy)pyridine,
6-(2-hydroxymethyl-2-hydroxypyrrolidin-1-yl)-3-amino-2-(2-hydroxyethyloxy)pyridine,
6-(2-carboxamidopyrrolidin-1-yl)-3-amino-2-(2-hydroxyethyloxy)pyridine,
6-(2-dimethylcarboxamidopyrrolidin-1-yl)-3-amino-2-(2-hydroxyethyloxy)pyridine,
6-(2-carboxamido-3-hydroxypyrrolidin-1-yl)-3-amino-2-(2-hydroxyethyloxy)pyridine,
6-(2-carboxamido-4-hydroxypyrrolidin-1-yl)-3-amino-2-(2-hydroxyethyloxy)pyridine,
6-(pyrrolidin-1-yl)-3-amino-2-ethoxypyridine,
6-(3-hydroxypyrrolidin-1-yl)-3-amino-2-ethoxypyridine,
6-(3-aminopyrrolidin-1-yl)-3-amino-2-ethoxypyridine,
6-(3-acetamidopyrrolidin-1-yl)-3-amino-2-ethoxypyridine,
6-(3,4-dihydroxypyrrolidin-1-yl)-3-amino-2-ethoxypyridine,
6-(2-carboxypyrrolidin-1-yl)-3-amino-2-ethoxypyridine,
6-(2-carboxy-3-hydroxypyrrolidin-1-yl)-3-amino-2-ethoxypyridine,
6-(2-carboxy-4-hydroxypyrrolidin-1-yl)-3-amino-2-ethoxypyridine,
6-(2-(hydroxymethyl)pyrrolidin-1-yl)-3-amino-2-ethoxypyridine,
6-(2-hydroxymethyl-4-hydroxypyrrolidin-1-yl)-3-amino-2-ethoxypyridine,
6-(2-hydroxymethyl-2-hydroxypyrrolidin-1-yl)-3-amino-2-ethoxypyridine,
6-(2-carboxamidopyrrolidin-1-yl)-3-amino-2-ethoxypyridine,
6-(2-dimethylcarboxamidopyrrolidin-1-yl)-3-amino-2-ethoxypyridine, 6-(2-carboxamido-3-hydroxypyrrolidin-1-yl)-3-amino-2-ethoxypyridine, and
6-(2-carboxamido-4-hydroxypyrrolidin-1-yl)-3-amino-2-ethoxypyridine.

The at least one 2,5-diaminopyridine derivative chosen from formula (I') may be synthesized, for example, according to the following synthetic scheme:

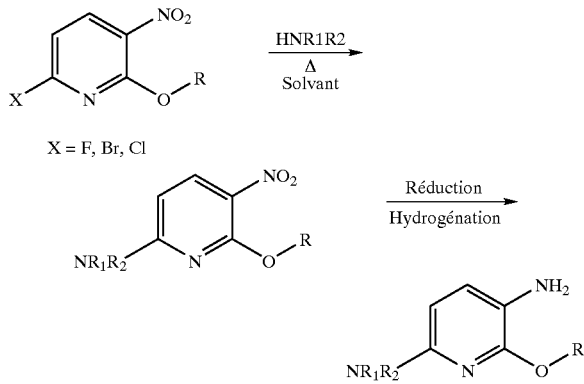

The first stage comprises reacting a 2-alkoxy-3-nitro-6-halopyridine derivative with an amine of $HNR_1R_2$ type in a polar solvent with a boiling point ranging from 70° C. to 180° C.

The reaction temperature may range, according to the pyridine derivatives and the nucleophilic amine, from 75° C. to 140° C.

The solvent may be chosen, for example, from alcohols, such as ethanol, isopropanol, butanol, pentanol, acetic acid, formic acid and dioxane and DMF.

The second stage comprises a reduction reaction carried out either by hydrogenation under heterogeneous catalysis or by hydrogen transfer or, alternatively, by metal hydrides or, alternatively, by the formic acid/acetic acid pair in the presence of palladium.

For example, use may be made of the method of hydrogenation catalysed by palladium(0), Pd(II) or Raney nickel or $PtO_2$.

The reduction by hydrogen transfer, reacting cyclohexene in the presence of palladium, may be employed.

Illustrative, non-limiting examples follow.

EXAMPLES

Example No. 1

Synthesis of 2-methoxy-6-(pyrrolidin-1-yl)-3-aminopyridine trihydrochloride

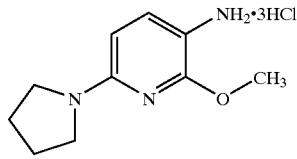

1. Synthesis of 2-methoxy-3-nitro-6-(pyrrolidin-1-yl)pyridine 4.79 g (0.021 mol) of 6-chloro-2-methoxy-3-nitropyridine, 40 ml of ethanol and 3.5 ml (0.042 mol) of pyrrolidine are charged to a fully equipped round-bottomed flask. The mixture is brought to reflux for 1 hour with stirring and then the mixture is cooled to ambient temperature. The product which crystallizes is filtered off and then washed with diisopropyl ether. After drying, 4.6 g of yellow powder are obtained, Yd: 96%.

Analysis by mass spectrometry and by magnetic resonance spectroscopy is in accordance with the structure envisaged.

2. Synthesis of 2-methoxy-6-(pyrrolidin-1-yl)-3-aminopyridine trihydrochloride 4 g (0.0179 mol) of 2-methoxy-3-nitro-6-(pyrrolidin-1-yl)pyridine, a product synthesized according to the above procedure, 200 ml of ethanol and 0.8 g of palladium-on-charcoal are charged to a 300 ml autoclave. The mixture is reduced for two hours with stirring at a pressure of 8 bar, the catalyst is subsequently removed by filtration and then the filtrate is acidified with hydrochloric acid. After diluting with diisopropyl ether, the precipitate formed is filtered off and dried under vacuum to constant weight. 2.8 g of powder are obtained, Yd=67.6%.

Analysis by mass spectrometry and by magnetic resonance spectroscopy is in accordance with the structure envisaged.

Example No. 2

1-(5-Amino-6-methoxypyridin-2-yl)pyrrolidin-3-ol dihydrochloride

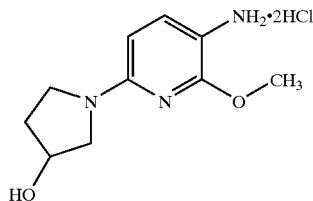

1. Synthesis of 1-(6-methoxy-5-nitropyridin-2-yl)pyrrolidin-3-ol 2 g (0.0106 mol) of 6-chloro-2-methoxy-3-nitropyridine, 25 ml of ethanol and 1.9 g of 3-pyrrolidinol are charged to a fully equipped round-bottomed flask. The mixture is brought to 50° C. for one hour with stirring and the mixture is poured onto an ice/water mixture with stirring. The precipitate formed is filtered off and dried. 2 g of yellow powder are obtained.

Analysis by mass spectrometry and by magnetic resonance spectroscopy is in accordance with the structure envisaged.

2. Synthesis of 1-(5-amino-6-methoxypyridin-2-yl)pyrrolidin-3-ol dihydrochloride 2 g (8.5 mmol) of 1-(6-methoxy-5-nitropyridin-2-yl)pyrrolidin-3-ol, 100 ml of ethanol and 0.5 g of palladium-on-charcoal are charged to a 300 ml autoclave. Reduction is carried out under a pressure of 8 bar for one hour with stirring. The catalyst is subsequently removed by filtration and then the filtrate is acidified with hydrochloric acid. After diluting with diisopropyl ether, the precipitate formed is filtered off and dried under vacuum to constant weight. 2.2 g of light beige powder are obtained, Yd=88%.

Analysis by mass spectrometry and by magnetic resonance spectroscopy is in accordance with the structure envisaged.

Example No. 3

3-Amino-2-methoxy-6-(morpholin-4-yl)pyridine dihydrochloride

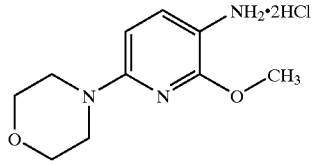

1. Synthesis of 4-(6-methoxy-5-nitropyridin-2-yl)morpholine:

4 g (0.02 mol) of 6-chloro-2-methoxy-3-nitropyridine, 60 ml of ethanol and 3.69 ml of morpholine are charged to a fully equipped round-bottomed flask. The mixture is brought to reflux for two hours with stirring and then the mixture is poured onto an ice/water mixture with stirring. The precipitate formed is filtered off and dried. 2.2 g of yellow powder are obtained, Yd=50%.

Analysis by mass spectrometry and by magnetic resonance spectroscopy is in accordance with the structure envisaged.

2. Synthesis of 3-amino-2-methoxy-6-(morpholin-4-yl)pyridine dihydrochloride 2 g (0.01 mol) of 4-(6-methoxy-5-nitropyridin-2-yl)morpholine, 100 ml of ethanol and 0.5 g of palladium-on-charcoal are charged to a 300 ml autoclave. Reduction is carried out under a pressure of 8 bar for one hour with stirring, the catalyst is removed by filtration and then the filtrate is acidified with hydrochloric acid. After diluting with diisopropyl ether, the precipitate formed is filtered off and dried. 2.2 g of light beige powder are obtained, Yd=88%.

Analysis by mass spectrometry and by magnetic resonance spectroscopy is in accordance with the structure envisaged.

Example No. 4

3-Amino-2-methoxy-6-(piperidin-1-yl)pyridine dihydrochloride

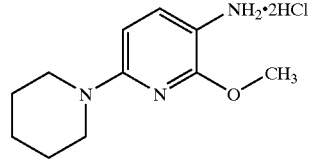

1. Synthesis of 2-methoxy-5-nitro-6-(piperidin-1-yl)pyridine 4 g (0.02 mol) of 6-chloro-2-methoxy-3-nitropyridine, 60 ml of ethanol and 4.2 ml of piperidine are charged to a fully equipped round-bottomed flask. The mixture is brought to reflux for two hours with stirring and then the mixture is poured onto an ice/water mixture with stirring. The precipitate formed is filtered off and dried. 2 g of yellow powder are obtained, Yd=42.5%.

Analysis by mass spectrometry and by magnetic resonance spectroscopy is in accordance with the structure envisaged.

2. Synthesis of 3-amino-2-methoxy-6-(piperidin-1-yl)pyridine Dihydrochloride 2 g (0.0085 mol) of 6-methoxy-5-nitro-2-(piperidin-1-yl)pyridine, 100 ml of ethanol and 0.5 g of palladium-on-charcoal are charged to a 300 ml autoclave. Reduction is carried out under a pressure of 8 bar for one hour with stirring. The catalyst is subsequently removed by filtration and then the filtrate is acidified with hydrochloric acid. After diluting with diisopropyl ether, the precipitate formed is filtered off and dried under vacuum to constant weight. 1.8 g of light beige powder are obtained, Yd=75%.

Analysis by mass spectrometry and by magnetic resonance spectroscopy is in accordance with the structure envisaged.

Example No. 5

6-N,N-(2-Hydroxyethyl)-methyl)amino)-3-amino-2-methoxypyridine dihydrochloride

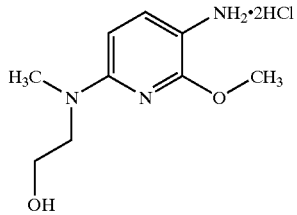

1. Synthesis of 6-N,N-(2-hydroxyethyl)-methyl)amino)-3-nitro-2-methoxypyridine:

4 g (0.02 mol) of 6-chloro-2-methoxy-3-nitropyridine, 60 ml of ethanol and 3.39 ml of 2-methylaminoethanol are charged to a fully equipped round-bottomed flask. The mixture is brought to 50° C. for one hour with stirring. The mixture is poured onto an ice/water mixture with stirring. The precipitate formed is filtered off and dried. 2.5 g of yellow powder are obtained, Yd=56%.

Analysis by mass spectrometry and by magnetic resonance spectroscopy is in accordance with the structure envisaged.

2. Synthesis of 6-N,N-(2-hydroxyethyl)-methyl)amino)-3-amino-2-methoxypyridine 2 g (0.0140 mol) of 6-(N,N-(2-hydroxyethyl)methylamino)-3-nitro-2-methoxypyridine, synthesized according to the above procedure, 100 ml of ethanol and 0.5 g of palladium-on-charcoal are charged to a 300 ml autoclave. The mixture is reduced for one hour at a pressure of 8 bar with stirring, the catalyst is subsequently removed by filtration and then the filtrate is acidified with hydrochloric acid. After diluting with diisopropyl ether, the precipitate formed is filtered off and dried. 2 g of powder are obtained, Yd=53%.

Analysis by mass spectrometry and by magnetic resonance spectroscopy is in accordance with the structure envisaged.

Example No. 6

2-(Pyrrolidin-1-yl)-5,6-diaminopyridine dihydrochloride

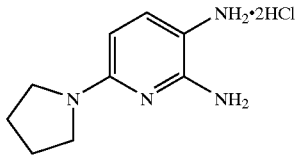

1. Synthesis of 2-amino-3-nitro-6-(pyrrolidin-1-yl)pyridine 2 g (0.012 mol) of 2-amino-6-chloro-3-nitropyridine, 30 ml of dioxane and 20 ml of water, and 1.8 g of pyrrolidine are charged to a fully equipped round-bottomed flask. The mixture is brought to 70° C. for one hour with stirring and then the mixture is poured onto an ice/water mixture with stirring. The precipitate formed is filtered off and dried. 2.2 g of yellow powder are obtained, Yd=88%.

Analysis by mass spectrometry and by magnetic resonance spectroscopy is in accordance with the structure envisaged.

2. Synthesis of 5,6-diamino-2-(pyrrolidin-1-yl)pyridine 2 g of 2-amino-3-nitro-6-(pyrrolidin-1-yl)pyridine, synthesized according to the above procedure, 100 ml of ethanol and 0.5 g of palladium-on-charcoal are charged to a 300 ml autoclave. The mixture is reduced for one hour at a pressure of 8 bar with stirring. The catalyst is subsequently removed by filtration and then the filtrate is acidified with hydrochloric acid. After diluting with diisopropyl ether, the precipitate formed is filtered off and dried. 2.1 g of powder are obtained, Yd=87.1%.

Analysis by mass spectrometry and by magnetic resonance spectroscopy is in accordance with the structure envisaged.

Example No. 7

N-(5,6-Diaminopyridin-2-yl)-3-hydroxypyrrolidine dihydrochloride

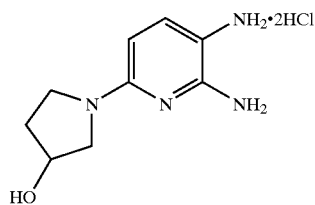

1. Synthesis of N-(6-amino-5-nitropyridin-2-yl)-3-hydroxypyrrolidine 2 g (0.012 mol) of 2-amino-6-chloro-3-nitropyridine, 30 ml of dioxane and 10 ml of water, and 1.8 g of 3-pyrrolidinol are charged to a fully equipped round-bottomed flask. The mixture is brought to 70° C. for one hour with stirring and then the mixture is poured onto an ice/water mixture with stirring. The precipitate formed is filtered off and dried. 2.36 g of yellow powder are obtained, Yd=87.4%.

Analysis by mass spectrometry and by magnetic resonance spectroscopy is in accordance with the structure envisaged.

2. Synthesis of N-(5,6-diaminopyridin-2-yl)-3-hydroxypyrrolidine dihydrochloride 2 g of N-(6-amino-5-nitropyridin-2-yl)-3-hydroxypyrrolidine, synthesized according to the above procedure, 100 ml of ethanol and 0.5 g of palladium-on-charcoal are charged to a 300 ml autoclave. The mixture is reduced for one hour at a pressure of 8 bar with stirring, the catalyst is subsequently removed by filtration and then the filtrate is acidified with hydrochloric acid. After diluting with diisopropyl ether, the precipitate formed is filtered off and dried. 2.1 g of powder are obtained, Yd=88%.

Analysis by mass spectrometry and by magnetic resonance spectroscopy is in accordance with the structure envisaged.

Example No. 8

2,6-Did(pyrrolidin-1-yl)-3-aminopyridine dihydrochloride

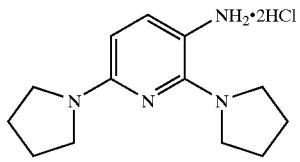

1. Synthesis of 2,6-did(pyrrolidin-1-yl)-3-nitropyridine 2 g (0.012 mol) of 2,6-dichloro-3-nitropyridine, 30 ml of dioxane and 10 ml of water, and 2.9 g of pyrrolidine are charged to a fully equipped round-bottomed flask. The mixture is brought to 70° C. for one hour with stirring and then the mixture is poured onto an ice/water mixture with stirring. The precipitate formed is filtered off and dried. 1.9 g of yellow powder are obtained, Yd=73%.

Analysis by mass spectrometry and by magnetic resonance spectroscopy is in accordance with the structure envisaged.

2. Synthesis of 2,6-did(pyrrolidin-1-yl)-3-aminopyridine dihydrochloride 1.5 g (0.0056 mol) of 2,6-did(pyrrolidin-1-yl)-3-nitropyridine, synthesized according to the above procedure, 100 ml of ethanol and 0.5 g of palladium-on-charcoal are charged to a 300 ml autoclave. The mixture is reduced for one hour at a pressure of 8 bar with stirring, the catalyst is subsequently removed by filtration and then the filtrate is acidified with hydrochloric acid. After diluting with diisopropyl ether, the precipitate formed is filtered off and dried. 0.95 g of powder is obtained, Yd=56%.

Analysis by mass spectrometry and by magnetic resonance spectroscopy is in accordance with the structure envisaged.

Examples 1 to 4 of Dyeing in an Alkaline Medium

|  | Examples | | | |
| --- | --- | --- | --- | --- |
|  | 1 | 2 | 3 | 4 |
| 2,6-Di(pyrrolidin-1-yl)-3-amino-pyridine dihydrochloride (base) | $10^{-3}$ mol | — | — | — |
| 5,6-Diamino-2-(pyrrolidin-1-yl)pyridine dihydrochloride (base) | — | $10^{-3}$ mol | — | — |
| N-(5,6-Diamino-pyridin-2-yl)-3-hydroxypyrrolidine dihydrochloride (base) | — | — | $10^{-3}$ mol | — |
| 2-Methoxy-6-(pyrrolidin-1-yl)-3-aminopyridine dihydrochloride (base) | — | — | — | $10^{-3}$ mol |
| 2,4-Diamino-phenoxyethanol dihydrochloride (coupler) | — | — | $10^{-3}$ mol | — |
| Resorcinol (coupler) | — | — | — | $10^{-3}$ mol |

-continued

|  | Examples | | | |
|---|---|---|---|---|
|  | 1 | 2 | 3 | 4 |
| 2-Methyl-5-aminophenol (coupler) | $10^{-3}$ mol | $10^{-3}$ mol | — | — |
| Dyeing vehicle (1) | (*) | (*) | (*) | (*) |
| Demineralized water, q.s. to | 100 g | 100 g | 100 g | 100 g |

(*) Dyeing vehicle (1) pH 9.5

| 96° Ethyl alcohol | 20 g |
|---|---|
| Sodium metabisulphite as a 35% aqueous solution | 0.2275 g A.M. |
| Pentasodium salt of diethylenetriaminepentaacetic acid | 0.48 g A.M. |
| $C_8$–$C_{15}$ Alkyl polyglucoside, sold as a 60% solution under the name Oramix CG 110 by Seppic | 3.6 g A.M. |
| Benzyl alcohol | 2.0 g |
| Polyethylene glycol comprising 8 mol of EO | 3.0 g |
| $NH_4Cl$ | 4.28 g |
| Aqueous ammonia comprising 20% of $NH_3$ | 6.8 g |

At the time of use, each composition is mixed with an equal weight of 20-volume aqueous hydrogen peroxide solution (6% by weight). A final pH of 7 is obtained.

Each mixture obtained is applied to locks of grey hair comprising 90% of white hairs. After leaving for 30 min, the locks are rinsed, washed with a standard shampoo, rinsed again and then dried.

The following dyeing results were obtained.

|  | Examples | | | |
|---|---|---|---|---|
|  | 1 | 2 | 3 | 4 |
| Hue observed | Turquoise green | Greenish dark grey | Dark green | Grey blue |

Examples 5 to 7 of Dyeing in an Acidic Medium

The following dyeing compositions were prepared:

|  | Examples | | |
|---|---|---|---|
|  | 5 | 6 | 7 |
| 5,6-Diamino-2-(pyrrolidin-1-yl)pyridine dihydrochloride (base) | $10^{-3}$ mol | — | — |
| 2-Methoxy-6-(pyrrolidin-1-yl)-3-aminopyridine dihydrochloride (base) | — | $10^{-3}$ mol | — |
| N-(5,6-Diaminopyridin-2-yl)-3-hydroxypyrrolidine dihydrochloride (base) | — | — | $10^{-3}$ mol |
| 2,4-Diaminophenoxyethanol dihydrochloride (coupler) | $10^{-3}$ mol | $10^{-3}$ mol | — |
| Resorcinol (coupler) | — | — | $10^{-3}$ mol |
| Dyeing vehicle (2) | (*) | (*) | (*) |
| Demineralized water, q.s. for | 100 g | 100 g | 100 g |

(*) Dyeing vehicle (2) pH 7

| 96° Ethyl alcohol | 20 g |
|---|---|
| Sodium metabisulphite as a 35% aqueous solution | 0.2275 g A.M. |
| Pentasodium salt of diethylenetriaminepentaacetic acid | 0.48 g A.M. |
| $C_8$–$C_{15}$ Alkyl polyglucoside, sold as a 60% solution under the name Oramix CG 110 by Seppic | 3.6 g A.M. |
| Benzyl alcohol | 2.0 g |
| Polyethylene glycol comprising 8 mol of EO | 3.0 g |
| $K_2HPO_4$ | 20.9 g |
| $KH_2PO_4$ | 10.88 g |

At the time of use, each composition is mixed with an equal weight of 20-volume aqueous hydrogen peroxide solution (6% by weight). A final pH of 9.5 is obtained.

Each mixture obtained is applied to locks of grey hair comprising 90% of white hairs. After leaving for 30 min, the locks are rinsed, washed with a standard shampoo, rinsed again and then dried.

The following dyeing results were obtained.

|  | Examples | | |
|---|---|---|---|
|  | 5 | 6 | 7 |
| Hue observed | Blue black | Dark blue | Medium green |

What is claimed is:

1. A dyeing composition comprising, in a medium acceptable for dyeing, at least one oxidation base chosen from compounds of formula (I) and addition salts thereof:

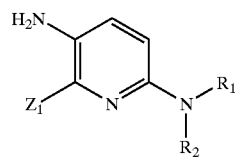

(I)

wherein $Z_1$ is chosen from $OR_3$ and $NR_4R_5$ radicals;

$R_1$, $R_2$, $R_4$ and $R_5$, independently of one another, are chosen from a hydrogen atom, $C_1$–$C_6$ alkyl radicals, $C_2$–$C_6$ (poly)aminoalkyl radicals, $C_2$–$C_6$ (poly)alkylaminoalkyl radicals, $C_2$–$C_6$ aminohydroxyalkyl radicals, $C_2$–$C_6$ acylaminoalkyl radicals, $C_2$–$C_6$ alkoxyalkyl radicals, $C_2$–$C_6$ hydroxyalkoxyalkyl radicals, $C_2$–$C_6$ aminoalkoxyalkyl radicals, $C_2$–$C_6$ (poly)hydroxyalkyl radicals, $C_2$–$C_6$ carboxylalkyl radicals and $C_2$–$C_6$ sulphoalkyl radicals;

or $R_1$ and $R_2$ may form, together with the nitrogen atom to which they are attached, a saturated heterocycle comprising from 5 to 8 ring members optionally substituted by at least one radical chosen from halogen atoms, amino, (di)alkylamino, hydroxyl, carboxyl, carboxamido, alkylsulphonylamino, acetamido and alkoxy radicals, and $C_1$–$C_6$ alkyl radicals optionally substituted by at least one radical chosen from hydroxyl, amino, (di)alkylamino, alkoxy, hydroxyalkoxy, aminoalkoxy, carboxyl, carboxamido, sulphonamido and sulpho radicals, wherein the heterocycle optionally comprises at least one group chosen from heteroatoms chosen from oxygen, optionally substituted nitrogen and sulphur and an $SO_2$ group, with the proviso that the heterocycle does not comprise a peroxide bond or a diazo or a nitroso radical;

or independently, $R_4$ and $R_5$ may form, together with the nitrogen atom to which they are attached, a saturated heterocycle comprising from 5 to 8 ring members optionally substituted by at least one radical chosen from halogen atoms, amino, (di)alkylamino, hydroxyl, carboxyl, carboxamido, alkylsulphonylamino, acetamido and alkoxy radicals, and $C_1$–$C_6$ alkyl radicals optionally substituted by at least one radical chosen from hydroxyl, amino, (di)alkylamino, alkoxy, hydroxyalkoxy, aminoalkoxy, carboxyl, carboxamido, sulphonamido and sulpho radicals, wherein the heterocycle optionally comprises at least one group chosen from heteroatoms chosen from oxygen, optionally substituted nitrogen and sulphur and an $SO_2$ group, with the proviso that the heterocycle does not comprise a peroxide bond or a diazo or a nitroso radical;

$R_3$ is chosen from linear and branched $C_1$–$C_6$ alkyl radicals optionally substituted by at least one radical chosen from hydroxyl, amino, $C_1$–$C_3$ mono- and dialkylamino radicals, wherein an alkyl part of the at least one radical is optionally substituted by at least one radical chosen from hydroxyl, amino, $C_1$–$C_2$ alkoxyalkoxy, and carboxyl radicals, with the proviso that the at least one oxidation base is not chosen from 2,3,6-triaminopyridine and addition salts thereof.

2. The composition according to claim 1, wherein $R_3$ is chosen from methyl, ethyl, hydroxyethyl, carboxymethyl and carboxyethyl radicals.

3. The composition according to claim 1, wherein $R_3$ is a methyl radical.

4. The composition according to claim 1, wherein $R_1$, $R_2$, $R_4$ and $R_5$, independently of one another, are chosen from $C_2$–$C_4$ (di)alkylaminoalkyl, $C_2$–$C_4$ carboxylalkyl, $C_2$–$C_4$ sulphoalkyl, $C_2$–$C_4$ (poly)hydroxyalkyl, and $C_2$–$C_4$ (poly)aminoalkyl radicals.

5. The composition according to claim 1, wherein $R_1$ and $R_2$ form, together with the nitrogen atom to which they are attached, a 5- to 8-membered heterocycle chosen from pyrrolidine, piperidine, homopiperidine, piperazine, homopiperazine and diazepane, wherein the heterocycle is optionally substituted by at least one radical chosen from $C_1$–$C_4$ alkyl radicals optionally substituted by at least one radical chosen from hydroxyl, amino, $C_1$–$C_2$ (di) alkylamino, carboxyl, carboxamido and sulphonamido radicals.

6. The composition according to claim 5, wherein $R_1$ and $R_2$ form, together with the nitrogen atom to which they are attached, a heterocycle chosen from 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-(hydroxymethyl)pyrrolidine, 3,4-dihydroxy-2-(hydroxymethyl)pyrrolidine, 3-hydroxypyrrolidine, 3,4-dihydroxypyrrolidine, 3-aminopyrrolidine, 3-(methylamino)pyrrolidine, 4-amino-3-hydroxypyrrolidine, 3-hydroxy-4-[(2-hydroxyethyl)amino]pyrrolidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, diazepane, N-methyldiazepane and N-(2-hydroxyethyl)diazepane.

7. The composition according to claim 6, wherein $R_1$ and $R_2$ form, together with the nitrogen atom to which they are attached, a heterocycle chosen from pyrrolidine, 3-hydroxypyrrolidine, 3-aminopyrrolidine, 3-acetamidopyrrolidine, 3-(methylsulphonylamino) pyrrolidine, pyrrolidine-2-carboxylic acid, 3-hydroxypyrrolidine-2-carboxylic acid, piperidine, hydroxypiperidine, homopiperidine, diazepane, N-methylhomopiperazine, and N-(β-hydroxyethyl)homopiperazine.

8. The composition according to claim 1, wherein $R_4$ and $R_5$ form, together with the nitrogen atom to which they are attached, a 5- to 8-membered heterocycle chosen from pyrrolidine, piperidine, homopiperidine, piperazine, homopiperazine and diazepane, wherein the heterocycle is optionally substituted by at least one radical chosen from $C_1$–$C_4$ alkyl radicals optionally substituted by at least one radical chosen from hydroxyl, amino, $C_1$–$C_2$ (di) alkylamino, carboxyl, carboxamido and sulphonamido radicals.

9. The composition according to claim 8, wherein $R_4$ and $R_5$ form, together with the nitrogen atom to which they are attached, a heterocycle chosen from 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-(hydroxymethyl)pyrrolidine, 3,4-dihydroxy-2-(hydroxymethyl)pyrrolidine, 3-hydroxypyrrolidine, 3,4-dihydroxypyrrolidine, 3-aminopyrrolidine, 3-(methylamino)pyrrolidine, 4-amino-3-hydroxypyrrolidine, 3-hydroxy-4-[(2-hydroxyethyl)amino]pyrrolidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, diazepane, N-methyldiazepane, and N-(2-hydroxyethyl)diazepane.

10. The composition according to claim 9, wherein $R_4$ and $R_5$ form, together with the nitrogen atom to which they are attached, a heterocycle chosen from pyrrolidine, 3-hydroxypyrrolidine, 3-aminopyrrolidine, 3-acetamidopyrrolidine, 3-(methylsulphonylamino) pyrrolidine, pyrrolidine-2-carboxylic acid, 3-hydroxypyrrolidine-2-carboxylic acid, piperidine, hydroxypiperidine, homopiperidine, diazepane, N-methylhomopiperazine, and N-(β-hydroxyethyl)homopiperazine.

11. The composition according to claim 1, wherein the at least one oxidation base chosen from compounds of formula (I) is chosen from:

2-methoxy-6-(pyrrolidin-1-yl)-3-aminopyridine, 1-(5-amino-6-methoxypyridin-2-yl)pyrrolidin-3-ol, 3-amino-2-methoxy-6-(morpholin-4-yl)pyridine, 3-amino-2-methoxy-6-(piperidin-1-yl)pyridine, 6-N,N-(2-hydroxyethyl)methyl)amino)-3-amino-2-methoxypyridine, 5,6-diamino-2-(pyrrolidin-1-yl)pyridine, N-(5,6-diaminopyridin-2-yl)-3-hydroxypyrrolidine,
2,6-did(pyrrolidin-1-yl)-5-aminopyridine,
6-(pyrrolidin-1-yl)-2,3-diaminopyridine,
6-(3-hydroxypyrrolidin-1-yl)-2,3-diaminopyridine,
6-(3-aminopyrrolidin-1-yl)-2,3-diaminopyridine,
6-(3-acetamidopyrrolidin-1-yl)-2,3-diaminopyridine,
6-(3,4-dihydroxypyrrolidin-1-yl)-2,3-diaminopyridine,
6-(2-carboxypyrrolidin-1-yl)-2,3-diaminopyridine,
6-(2-carboxy-3-hydroxypyrrolidin-1-yl)-2,3-diaminopyridine,
6-(2-carboxy-4-hydroxypyrrolidin-1-yl)-2,3-diaminopyridine,
6-(2-(hydroxymethyl)pyrrolidin-1-yl)-2,3-diaminopyridine,
6-(2-hydroxymethyl-4-hydroxypyrrolidin-1-yl)-2,3-diaminopyridine,
6-(2-hydroxymethyl-2-hydroxypyrrolidin-1-yl)-2,3-diaminopyridine,
6-(2-carboxamidopyrrolidin-1-yl)-2,3-diaminopyridine,
6-(2-dimethylcarboxamidopyrrolidin-1-yl)-2,3-diaminopyridine,
6-(2-carboxamido-3-hydroxypyrrolidin-1-yl)-2,3-diaminopyridine,
6-(2-carboxamido-4-hydroxypyrrolidin-1-yl)-2,3-diaminopyridine,
6-(pyrrolidin-1-yl)-3-amino-2-methylaminopyridine,
6-(3-hydroxypyrrolidin-1-yl)-3-amino-2-methylaminopyridine,
6-(3-aminopyrrolidin-1-yl)-3-amino-2-methylaminopyridine,
6-(3-acetamidopyrrolidin-1-yl)-3-amino-2-methylaminopyridine,
6-(3,4-dihydroxypyrrolidin-1-yl)-3-amino-2-methylaminopyridine,
6-(2-carboxypyrrolidin-1-yl)-3-amino-2-methylaminopyridine,
6-(2-carboxy-3-hydroxypyrrolidin-1-yl)-3-amino-2-methylaminopyridine,
6-(2-carboxy-4-hydroxypyrrolidin-1-yl)-3-amino-2-methylaminopyridine,
6-(2-(hydroxymethyl)pyrrolidin-1-yl)-3-amino-2-methylaminopyridine,
6-(2-hydroxymethyl-4-hydroxypyrrolidin-1-yl)-3-amino-2-methylaminopyridine,
6-(2-hydroxymethyl-2-hydroxypyrrolidin-1-yl)-3-amino-2-methylaminopyridine,
6-(2-carboxamidopyrrolidin-1-yl)-3-amino-2-methylaminopyridine,
6-(2-dimethylcarboxamidopyrrolidin-1-yl)-3-amino-2-methylaminopyridine,
6-(2-carboxamido-3-hydroxypyrrolidin-1-yl)-3-amino-2-methylaminopyridine,
6-(2-carboxamido-4-hydroxypyrrolidin-1-yl)-3-amino-2-methylaminopyridine,
6-(pyrrolidin-1-yl)-3-amino-2-ethylaminopyridine,
6-(3-hydroxypyrrolidin-1-yl)-3-amino-2-ethylaminopyridine,
6-(3-aminopyrrolidin-1-yl)-3-amino-2-ethylaminopyridine,
6-(3-acetamidopyrrolidin-1-yl)-3-amino-2-ethylaminopyridine,
6-(3,4-dihydroxypyrrolidin-1-yl)-3-amino-2-ethylaminopyridine,
6-(2-carboxypyrrolidin-1-yl)-3-amino-2-ethylaminopyridine,
6-(2-carboxy-3-hydroxypyrrolidin-1-yl)-3-amino-2-ethylaminopyridine,
6-(2-carboxy-4-hydroxypyrrolidin-1-yl)-3-amino-2-ethylaminopyridine,
6-(2-(hydroxymethyl)pyrrolidin-1-yl)-3-amino-2-ethylaminopyridine,
6-(2-hydroxymethyl-4-hydroxypyrrolidin-1-yl)-3-amino-2-ethylaminopyridine,
6-(2-hydroxymethyl-2-hydroxypyrrolidin-1-yl)-3-amino-2-ethylaminopyridine,
6-(2-carboxamidopyrrolidin-1-yl)-3-amino-2-ethylaminopyridine,
6-(2-dimethylcarboxamidopyrrolidin-1-yl)-3-amino-2-ethylaminopyridine,
6-(2-carboxamido-3-hydroxypyrrolidin-1-yl)-3-amino-2-ethylaminopyridine,
6-(2-carboxamido-4-hydroxypyrrolidin-1-yl)-3-amino-2-ethylaminopyridine,
6-(pyrrolidin-1-yl)-3-amino-2-(2-hydroxyethylamino)pyridine,
6-(3-hydroxypyrrolidin-1-yl)-3-amino-2-(2-hydroxyethylamino)pyridine,
6-(3-aminopyrrolidin-1-yl)-3-amino-2-(2-hydroxyethylamino)pyridine,
6-(3-acetamidopyrrolidin-1-yl)-3-amino-2-(2-hydroxyethylamino)pyridine,
6-(3,4-dihydroxypyrrolidin-1-yl)-3-amino-2-(2-hydroxyethylamino)pyridine,
6-(2-carboxypyrrolidin-1-yl)-3-amino-2-(2-hydroxyethylamino)pyridine,
6-(2-carboxy-3-hydroxypyrrolidin-1-yl)-3-amino-2-(2-hydroxyethylamino)pyridine,
6-(2-carboxy-4-hydroxypyrrolidin-1-yl)-3-amino-2-(2-hydroxyethylamino)pyridine,
6-(2-(hydroxymethyl)pyrrolidin-1-yl)-3-amino-2-(2-hydroxyethylamino)pyridine,
6-(2-hydroxymethyl-4-hydroxypyrrolidin-1-yl)-3-amino-2-(2-hydroxyethylamino)pyridine,
6-(2-hydroxymethyl-2-hydroxypyrrolidin-1-yl)-3-amino-2-(2-hydroxyethylamino)pyridine,
6-(2-carboxamidopyrrolidin-1-yl)-3-amino-2-(2-hydroxyethylamino)pyridine,
6-(2-dimethylcarboxamidopyrrolidin-1-yl)-3-amino-2-(2-hydroxyethylamino)pyridine,
6-(2-carboxamido-3-hydroxypyrrolidin-1-yl)-3-amino-2-(2-hydroxyethylamino)pyridine,
6-(2-carboxamido-4-hydroxypyrrolidin-1-yl)-3-aminopyridine,
6-(pyrrolidin-1-yl)-3-amino-2-(2-aminoethylamino)pyridine,
6-(3-hydroxypyrrolidin-1-yl)-3-amino-2-(2-aminoethylamino)pyridine,
6-(3-aminopyrrolidin-1-yl)-3-amino-2-(2-aminoethylamino)pyridine,
6-(3-acetamidopyrrolidin-1-yl)-3-amino-2-(2-aminoethylamino)pyridine,
6-(3,4-dihydroxypyrrolidin-1-yl)-3-amino-2-(2-aminoethylamino)pyridine, 6-(2-carboxypyrrolidin-1-yl)-3-amino-2-(2-aminoethylamino)pyridine,
6-(2-carboxy-3-hydroxypyrrolidin-1-yl)-3-amino-2-(2-aminoethylamino)pyridine,
6-(2-carboxy-4-hydroxypyrrolidin-1-yl)-3-amino-2-(2-aminoethylamino)pyridine,
6-(2-(hydroxymethyl)pyrrolidin-1-yl)-3-amino-2-(2-aminoethylamino)pyridine,
6-(2-hydroxymethyl-4-hydroxypyrrolidin-1-yl)-3-amino-2-(2-aminoethylamino)pyridine,
6-(2-hydroxymethyl-2-hydroxypyrrolidin-1-yl)-3-amino-2-(2-aminoethylamino)pyridine,
6-(2-carboxamidopyrrolidin-1-yl)-3-amino-2-(2-aminoethylamino)pyridine,
6-(2-dimethylcarboxamidopyrrolidin-1-yl)-3-amino-2-(2-aminoethylamino)pyridine,
6-(2-carboxamido-3-hydroxypyrrolidin-1-yl)-3-amino-2-(2-aminoethylamino)pyridine,
6-(2-carboxamido-4-hydroxypyrrolidin-1-yl)-3-amino-2-(2-aminoethylamino)pyridine,
6-(pyrrolidin-1-yl)-3-amino-2-(2-acetamidoethylamino)pyridine,
6-(3-hydroxypyrrolidin-1-yl)-3-amino-2-(2-acetamidoethylamino)pyridine,
6-(3-aminopyrrolidin-1-yl)-3-amino-2-(2-acetamidoethylamino)pyridine,
6-(3-acetamidopyrrolidin-1-yl)-3-amino-2-(2-acetamidoethylamino)pyridine,
6-(3,4-dihydroxypyrrolidin-1-yl)-3-amino-2-(2-acetamidoethylamino)pyridine,
6-(2-carboxypyrrolidin-1-yl)-3-amino-2-(2-acetamidoethylamino)pyridine,
6-(2-carboxy-3-hydroxypyrrolidin-1-yl)-3-amino-2-(2-acetamidoethylamino)pyridine,
6-(2-carboxy-4-hydroxypyrrolidin-1-yl)-3-amino-2-(2-acetamidoethylamino)pyridine,
6-(2-(hydroxymethyl)pyrrolidin-1-yl)-3-amino-2-(2-acetamidoethylamino)pyridine,
6-(2-hydroxymethyl-4-hydroxypyrrolidin-1-yl)-3-amino-2-(2-acetamidoethylamino)pyridine,
6-(2-hydroxymethyl-2-hydroxypyrrolidin-1-yl)-3-amino-2-(2-acetamidoethylamino)pyridine,
6-(2-carboxamidopyrrolidin-1-yl)-3-amino-2-(2-acetamidoethylamino)pyridine,
6-(2-dimethylcarboxamidopyrrolidin-1-yl)-3-amino-2-(2-acetamidoethylamino)pyridine,
6-(2-carboxamido-3-hydroxypyrrolidin-1-yl)-3-amino-2-(2-acetamidoethylamino)pyridine,
6-(2-carboxamido-4-hydroxypyrrolidin-1-yl)-3-amino-2-(2-acetamidoethylamino)pyridine,
6-(pyrrolidin-1-yl)-3-amino-2-(pyrrolidin-1-yl)pyridine,
6-(3-hydroxypyrrolidin-1-yl)-3-amino-2-(pyrrolidin-1-yl)pyridine,
6-(3-aminopyrrolidin-1-yl)-3-amino-2-(pyrrolidin-1-yl)pyridine,
6-(3-acetamidopyrrolidin-1-yl)-3-amino-2-(pyrrolidin-1-yl)pyridine,
6-(3,4-dihydroxypyrrolidin-1-yl)-3-amino-2-(pyrrolidin-1-yl)pyridine,
6-(2-carboxypyrrolidin-1-yl)-3-amino-2-(pyrrolidin-1-yl)pyridine,
6-(2-carboxy-3-hydroxypyrrolidin-1-yl)-3-amino-2-(pyrrolidin-1-yl)pyridine,
6-(2-carboxy-4-hydroxypyrrolidin-1-yl)-3-amino-2-(pyrrolidin-1-yl)pyridine,
6-(2-(hydroxymethyl)pyrrolidin-1-yl)-3-amino-2-(pyrrolidin-1-yl)pyridine,
6-(2-hydroxymethyl-4-hydroxypyrrolidin-1-yl)-3-amino-2-(pyrrolidin-1-yl)pyridine,
6-(2-hydroxymethyl-2-hydroxypyrrolidin-1-yl)-3-amino-2-(pyrrolidin-1-yl)pyridine,
6-(2-carboxamidopyrrolidin-1-yl)-3-amino-2-(pyrrolidin-1-yl)pyridine,
6-(2-dimethylcarboxamidopyrrolidin-1-yl)-3-amino-2-(pyrrolidin-1-yl)pyridine,
6-(2-carboxamido-3-hydroxypyrrolidin-1-yl)-3-amino-2-(pyrrolidin-1-yl)pyridine,
6-(2-carboxamido-4-hydroxypyrrolidin-1-yl)-3-amino-2-(pyrrolidin-1-yl)pyridine,
6-(pyrrolidin-1-yl)-3-amino-2-(3-hydroxypyrrolidin-1-yl)pyridine,
6-(3-hydroxypyrrolidin-1-yl)-3-amino-2-(3-hydroxypyrrolidin-1-yl)pyridine,
6-(3-aminopyrrolidin-1-yl)-3-amino-2-(3-hydroxypyrrolidin-1-yl)pyridine,
6-(3-acetamidopyrrolidin-1-yl)-3-amino-2-(3-hydroxypyrrolidin-1-yl)pyridine,
6-(3,4-dihydroxypyrrolidin-1-yl)-3-amino-2-(3-hydroxypyrrolidin-1-yl)pyridine,
6-(2-carboxypyrrolidin-1-yl)-3-amino-2-(3-hydroxypyrrolidin-1-yl)pyridine,
6-(2-carboxy-3-hydroxypyrrolidin-1-yl)-3-amino-2-(3-hydroxypyrrolidin-1-yl)pyridine,
6-(2-carboxy-4-hydroxypyrrolidin-1-yl)-3-amino-2-(3-hydroxypyrrolidin-1-yl)pyridine,
6-(2-(hydroxymethyl)pyrrolidin-1-yl)-3-amino-2-(3-hydroxypyrrolidin-1-yl)pyridine,
6-(2-hydroxymethyl-4-hydroxypyrrolidin-1-yl)-3-amino-2-(3-hydroxypyrrolidin-1-yl)pyridine,
6-(2-hydroxymethyl-2-hydroxypyrrolidin-1-yl)-3-amino-2-(3-hydroxypyrrolidin-1-yl)pyridine,
6-(2-carboxamidopyrrolidin-1-yl)-3-amino-2-(3-hydroxypyrrolidin-1-yl)pyridine,
6-(2-dimethylcarboxamidopyrrolidin-1-yl)-3-amino-2-(3-hydroxypyrrolidin-1-yl)pyridine,
6-(2-carboxamido-3-hydroxypyrrolidin-1-yl)-3-amino-2-(3-hydroxypyrrolidin-1-yl)pyridine,
6-(2-carboxamido-4-hydroxypyrrolidin-1-yl)-3-amino-2-(3-hydroxypyrrolidin-1-yl)pyridine,
6-(pyrrolidin-1-yl)-3-amino-2-(2-carboxypyrrolidin-1-yl)pyridine,
6-(3-hydroxypyrrolidin-1-yl)-3-amino-2-(2-carboxypyrrolidin-1-yl)pyridine,
6-(3-aminopyrrolidin-1-yl)-3-amino-2-(2-carboxypyrrolidin-1-yl)pyridine,
6-(3-acetamidopyrrolidin-1-yl)-3-amino-2-(2-carboxypyrrolidin-1-yl)pyridine,
6-(3,4-dihydroxypyrrolidin-1-yl)-3-amino-2-(2-carboxypyrrolidin-1-yl)pyridine,
6-(2-carboxypyrrolidin-1-yl)-3-amino-2-(2-carboxypyrrolidin-1-yl)pyridine,
6-(2-carboxy-3-hydroxypyrrolidin-1-yl)-3-amino-2-(2-carboxypyrrolidin-1-yl)pyridine, 6-(2-carboxy-4-hydroxypyrrolidin-1-yl)-3-amino-2-(2-carboxypyrrolidin-1-yl)pyridine,
6-(2-(hydroxymethyl)pyrrolidin-1-yl)-3-amino-2-(2-carboxypyrrolidin-1-yl)pyridine,
6-(2-hydroxymethyl-4-hydroxypyrrolidin-1-yl)-3-amino-2-(2-carboxypyrrolidin-1-yl)pyridine,
6-(2-hydroxymethyl-2-hydroxypyrrolidin-1-yl)-3-amino-2-(2-carboxypyrrolidin-1-yl)pyridine,
6-(2-carboxamidopyrrolidin-1-yl)-3-amino-2-(2-carboxypyrrolidin-1-yl)pyridine,
6-(2-dimethylcarboxamidopyrrolidin-1-yl)-3-amino-2-(2-carboxypyrrolidin-1-yl)pyridine,
6-(2-carboxamido-3-hydroxypyrrolidin-1-yl)-3-amino-2-(2-carboxypyrrolidin-1-yl)pyridine,
6-(2-carboxamido-4-hydroxypyrrolidin-1-yl)-3-amino-2-(2-carboxypyrrolidin-1-yl)pyridine,
6-(pyrrolidin-1-yl)-3-amino-2-(2-(hydroxymethyl)pyrrolidin-1-yl)pyridine,
6-(3-hydroxypyrrolidin-1-yl)-3-amino-2-(2-(hydroxymethyl)pyrrolidin-1-yl)pyridine,
6-(3-aminopyrrolidin-1-yl)-3-amino-2-(2-(hydroxymethyl)pyrrolidin-1-yl)pyridine,
6-(3-acetamidopyrrolidin-1-yl)-3-amino-2-(2-(hydroxymethyl)pyrrolidin-1-yl)pyridine,
6-(3,4-dihydroxypyrrolidin-1-yl)-3-amino-2-(2-(hydroxymethyl)pyrrolidin-1-yl)pyridine,
6-(2-carboxypyrrolidin-1-yl)-3-amino-2-(2-(hydroxymethyl)pyrrolidin-1-yl)pyridine,
6-(2-carboxy-3-hydroxypyrrolidin-1-yl)-3-amino-2-(2-(hydroxymethyl)pyrrolidin-1-yl)pyridine,
6-(2-carboxy-4-hydroxypyrrolidin-1-yl)-3-amino-2-(2-(hydroxymethyl)pyrrolidin-1-yl)pyridine,
6-(2-(hydroxymethyl)pyrrolidin-1-yl)-3-amino-2-(2-(hydroxymethyl)pyrrolidin-1-yl)pyridine,
6-(2-hydroxymethyl-4-hydroxypyrrolidin-1-yl)-3-amino-2-(2-(hydroxymethyl)pyrrolidin-1-yl)pyridine,
6-(2-hydroxymethyl-2-hydroxypyrrolidin-1-yl)-3-amino-2-(2-(hydroxymethyl)pyrrolidin-1-yl)pyridine,
6-(2-carboxamidopyrrolidin-1-yl)-3-amino-2-(2-(hydroxymethyl)pyrrolidin-1-yl)pyridine,
6-(2-dimethylcarboxamidopyrrolidin-1-yl)-3-amino-2-(2-(hydroxymethyl)pyrrolidin-1-yl)pyridine,
6-(2-carboxamido-3-hydroxypyrrolidin-1-yl)-3-amino-2-(2-(hydroxymethyl)pyrrolidin-1-yl)pyridine,
6-(2-carboxamido-4-hydroxypyrrolidin-1-yl)-3-amino-2-(2-(hydroxymethyl)pyrrolidin-1-yl)pyridine,
6-(pyrrolidin-1-yl)-3-amino-2-(2-carboxamidopyrrolidin-1-yl)pyridine,
6-(3-hydroxypyrrolidin-1-yl)-3-amino-2-(2-carboxamidopyrrolidin-1-yl)pyridine,
6-(3-aminopyrrolidin-1-yl)-3-amino-2-(2-carboxamidopyrrolidin-1-yl)pyridine,
6-(3-acetamidopyrrolidin-1-yl)-3-amino-2-(2-carboxamidopyrrolidin-1-yl)pyridine,
6-(3,4-dihydroxypyrrolidin-1-yl)-3-amino-2-(2-carboxamidopyrrolidin-1-yl)pyridine,
6-(2-carboxypyrrolidin-1-yl)-3-amino-2-(2-carboxamidopyrrolidin-1-yl)pyridine,
6-(2-carboxy-3-hydroxypyrrolidin-1-yl)-3-amino-2-(2-carboxamidopyrrolidin-1-yl)pyridine,
6-(2-carboxy-4-hydroxypyrrolidin-1-yl)-3-amino-2-(2-carboxamidopyrrolidin-1-yl)pyridine,
6-(2-(hydroxymethyl)pyrrolidin-1-yl)-3-amino-2-(2-carboxamidopyrrolidin-1-yl)pyridine,
6-(2-hydroxymethyl-4-hydroxypyrrolidin-1-yl)-3-amino-2-(2-carboxamidopyrrolidin-1-yl)pyridine,
6-(2-hydroxymethyl-2-hydroxypyrrolidin-1-yl)-3-amino-2-(2-carboxamidopyrrolidin-1-yl)pyridine,
6-(2-carboxamidopyrrolidin-1-yl)-3-amino-2-(2-carboxamidopyrrolidin-1-yl)pyridine,
6-(2-dimethylcarboxamidopyrrolidin-1-yl)-3-amino-2-(2-carboxamidopyrrolidin-1-yl)pyridine,
6-(2-carboxamido-3-hydroxypyrrolidin-1-yl)-3-amino-2-(2-carboxamidopyrrolidin-1-yl)pyridine,
6-(2-carboxamido-4-hydroxypyrrolidin-1-yl)-3-amino-2-(2-carboxamidopyrrolidin-1-yl)pyridine,
6-(pyrrolidin-1-yl)-3-amino-2-dimethylaminopyridine,
6-(3-hydroxypyrrolidin-1-yl)-3-amino-2-dimethylaminopyridine,
6-(3-aminopyrrolidin-1-yl)-3-amino-2-dimethylaminopyridine,
6-(3-acetamidopyrrolidin-1-yl)-3-amino-2-dimethylaminopyridine,
6-(3,4-dihydroxypyrrolidin-1-yl)-3-amino-2-dimethylaminopyridine,
6-(2-carboxypyrrolidin-1-yl)-3-amino-2-dimethylaminopyridine,
6-(2-carboxy-3-hydroxypyrrolidin-1-yl)-3-amino-2-dimethylaminopyridine,
6-(2-carboxy-4-hydroxypyrrolidin-1-yl)-3-amino-2-dimethylaminopyridine,
6-(2-(hydroxymethyl)pyrrolidin-1-yl)-3-amino-2-dimethylaminopyridine,
6-(2-hydroxymethyl-4-hydroxypyrrolidin-1-yl)-3-amino-2-did methylaminopyridine,
6-(2-hydroxymethyl-2-hydroxypyrrolidin-1-yl)-3-amino-2-dimethylaminopyridine,
6-(2-carboxamidopyrrolidin-1-yl)-3-amino-2-dimethylaminopyridine,
6-(2-dimethylcarboxamidopyrrolidin-1-yl)-3-amino-2-dimethylaminopyridine,
6-(2-carboxamido-3-hydroxypyrrolidin-1-yl)-3-amino-2-dimethylaminopyridine,
6-(2-carboxamido-4-hydroxypyrrolidin-1-yl)-3-amino-2-dimethylaminopyridine,
6-(pyrrolidin-1-yl)-3-amino-2-[methyl(2-hydroxyethyl)amino]pyridine,
6-(3-hydroxypyrrolidin-1-yl)-3-amino-2-[methyl(2-hydroxyethyl)amino]pyridine,
6-(3-aminopyrrolidin-1-yl)-3-amino-2-[methyl(2-hydroxyethyl)amino]pyridine,
6-(3-acetamidopyrrolidin-1-yl)-3-amino-2-[methyl(2-hydroxyethyl)amino]pyridine,
6-(3,4-dihydroxypyrrolidin-1-yl)-3-amino-2-[methyl(2-hydroxyethyl)amino]pyridine,
6-(2-carboxypyrrolidin-1-yl)-3-amino-2-[methyl(2-hydroxyethyl)amino]pyridine,
6-(2-carboxy-3-hydroxypyrrolidin-1-yl)-3-amino-2-[methyl(2-hydroxyethyl)amino]pyridine,
6-(2-carboxy-4-hydroxypyrrolidin-1-yl)-3-amino-2-[methyl(2-hydroxyethyl)amino]pyridine,
6-(2-(hydroxymethyl)pyrrolidin-1-yl)-3-amino-2-[methyl(2-hydroxyethyl)amino]pyridine, 6-(2-hydroxymethyl-4-hydroxypyrrolidin-1-yl)-3-amino-2-[methyl(2-hydroxyethyl)amino]pyridine,
6-(2-hydroxymethyl-2-hydroxypyrrolidin-1-yl)-3-amino-2-[methyl(2-hydroxyethyl)amino]pyridine,
6-(2-carboxamidopyrrolidin-1-yl)-3-amino-2-[methyl(2-hydroxyethyl)amino]pyridine,
6-(2-dimethylcarboxamidopyrrolidin-1-yl)-3-amino-2-[methyl(2-hydroxyethyl)amino]pyridine,
6-(2-carboxamido-3-hydroxypyrrolidin-1-yl)-3-amino-2-[methyl(2-hydroxyethyl)amino]pyridine,
6-(2-carboxamido-4-hydroxypyrrolidin-1-yl)-3-amino-2-[methyl(2-hydroxyethyl)amino]pyridine,
6-(pyrrolidin-1-yl)-3-amino-2-[methyl(2-aminoethyl)amino] pyridine,
6-(3-hydroxypyrrolidin-1-yl)-3-amino-2-[methyl(2-aminoethyl)amino]pyridine,
6-(3-aminopyrrolidin-1-yl)-3-amino-2-[methyl(2-aminoethyl)amino]pyridine,
6-(3-acetamidopyrrolidin-1-yl)-3-amino-2-[methyl(2-aminoethyl)amino]pyridine,
6-(3,4-dihydroxypyrrolidin-1-yl)-3-amino-2-[methyl(2-aminoethyl)amino]pyridine,
6-(2-carboxypyrrolidin-1-yl)-3-amino-2-[methyl(2-aminoethyl)amino]pyridine,
6-(2-carboxy-3-hydroxypyrrolidin-1-yl)-3-amino-2-[methyl(2-aminoethyl)amino]pyridine,
6-(2-carboxy-4-hydroxypyrrolidin-1-yl)-3-amino-2-[methyl(2-aminoethyl)amino]pyridine,
6-(2-(hydroxymethyl)pyrrolidin-1-yl)-3-amino-2-[methyl(2-aminoethyl)amino]pyridine,
6-(2-hydroxymethyl-4-hydroxypyrrolidin-1-yl)-3-amino-2-[methyl(2-aminoethyl)amino]pyridine,
6-(2-hydroxymethyl-2-hydroxypyrrolidin-1-yl)-3-amino-2-[methyl(2-aminoethyl)amino]pyridine,
6-(2-carboxamidopyrrolidin-1-yl)-3-amino-2-[methyl(2-aminoethyl)amino]pyridine,
6-(2-dimethylcarboxamidopyrrolidin-1-yl)-3-amino-2-[methyl(2-aminoethyl)amino]pyridine,
6-(2-carboxamido-3-hydroxypyrrolidin-1-yl)-3-amino-2-[methyl(2-aminoethyl)amino]pyridine,
6-(2-carboxamido-4-hydroxypyrrolidin-1-yl)-3-amino-2-[methyl(2-aminoethyl)amino]pyridine,
6-(pyrrolidin-1-yl)-3-amino-2-[methyl(2-acetamidoethyl)amino]pyridine,
6-(3-hydroxypyrrolidin-1-yl)-3-amino-2-[methyl(2-acetamidoethyl)amino]pyridine,
6-(3-aminopyrrolidin-1-yl)-3-amino-2-[methyl(2-acetamidoethyl)amino]pyridine,
6-(3-acetamidopyrrolidin-1-yl)-3-amino-2-[methyl(2-acetamidoethyl)amino]pyridine,
6-(3,4-dihydroxypyrrolidin-1-yl)-3-amino-2-[methyl(2-acetamidoethyl)amino]pyridine,
6-(2-carboxypyrrolidin-1-yl)-3-amino-2-[methyl(2-acetamidoethyl)amino]pyridine,
6-(2-carboxy-3-hydroxypyrrolidin-1-yl)-3-amino-2-[methyl(2-acetamidoethyl)amino]pyridine,
6-(2-carboxy-4-hydroxypyrrolidin-1-yl)-3-amino-2-[methyl(2-acetamidoethyl)amino]pyridine,
6-(2-(hydroxymethyl)pyrrolidin-1-yl)-3-amino-2-[methyl(2-acetamidoethyl)amino]pyridine,
6-(2-hydroxymethyl-4-hydroxypyrrolidin-1-yl)-3-amino-2-[methyl(2-acetamidoethyl)amino]pyridine,
6-(2-hydroxymethyl-2-hydroxypyrrolidin-1-yl)-3-amino-2-[methyl(2-acetamidoethyl)amino]pyridine,
6-(2-carboxamidopyrrolidin-1-yl)-3-amino-2-[methyl(2-acetamidoethyl)amino]pyridine,
6-(2-dimethylcarboxamidopyrrolidin-1-yl)-3-amino-2-[methyl(2-acetamidoethyl)amino]pyridine,
6-(2-carboxamido-3-hydroxypyrrolidin-1-yl)-3-amino-2-[methyl(2-acetamidoethyl)amino]pyridine,
6-(2-carboxamido-4-hydroxypyrrolidin-1-yl)-3-amino-2-[methyl(2-acetamidoethyl)amino]pyridine,
6-(pyrrolidin-1-yl)-3-amino-2-methoxypyridine,
6-(3-hydroxypyrrolidin-1-yl)-3-amino-2-methoxypyridine,
6-(3-aminopyrrolidin-1-yl)-3-amino-2-methoxypyridine,
6-(3-acetamidopyrrolidin-1-yl)-3-amino-2-methoxypyridine,
6-(3,4-dihydroxypyrrolidin-1-yl)-3-amino-2-methoxypyridine,
6-(2-carboxypyrrolidin-1-yl)-3-amino-2-methoxypyridine,
6-(2-carboxy-3-hydroxypyrrolidin-1-yl)-3-amino-2-methoxypyridine,
6-(2-carboxy-4-hydroxypyrrolidin-1-yl)-3-amino-2-methoxypyridine,
6-(2-(hydroxymethyl)pyrrolidin-1-yl)-3-amino-2-methoxypyridine,
6-(2-hydroxymethyl-4-hydroxypyrrolidin-1-yl)-3-amino-2-methoxypyridine,
6-(2-hydroxymethyl-2-hydroxypyrrolidin-1-yl)-3-amino-2-methoxypyridine,
6-(2-carboxamidopyrrolidin-1-yl)-3-amino-2-methoxypyridine,
6-(2-dimethylcarboxamidopyrrolidin-1-yl)-3-amino-2-methoxypyridine,
6-(2-carboxamido-3-hydroxypyrrolidin-1-yl)-3-amino-2-methoxypyridine,
6-(2-carboxamido-4-hydroxypyrrolidin-1-yl)-3-amino-2-methoxypyridine,
6-(pyrrolidin-1-yl)-3-amino-2-(2-hydroxyethyloxy)pyridine,
6-(3-hydroxypyrrolidin-1-yl)-3-amino-2-(2-hydroxyethyloxy)pyridine,
6-(3-aminopyrrolidin-1-yl)-3-amino-2-(2-hydroxyethyloxy)pyridine,
6-(3-acetamidopyrrolidin-1-yl)-3-amino-2-(2-hydroxyethyloxy)pyridine,
6-(3,4-dihydroxypyrrolidin-1-yl)-3-amino-2-(2-hydroxyethyloxy)pyridine,
6-(2-carboxypyrrolidin-1-yl)-3-amino-2-(2-hydroxyethyloxy)pyridine,
6-(2-carboxy-3-hydroxypyrrolidin-1-yl)-3-amino-2-(2-hydroxyethyloxy)pyridine,
6-(2-carboxy-4-hydroxypyrrolidin-1-yl)-3-amino-2-(2-hydroxyethyloxy)pyridine,
6-(2-(hydroxymethyl)pyrrolidin-1-yl)-3-amino-2-(2-hydroxyethyloxy)pyridine,
6-(2-hydroxymethyl-4-hydroxypyrrolidin-1-yl)-3-amino-2-(2-hydroxyethyloxy)pyridine,
6-(2-hydroxymethyl-2-hydroxypyrrolidin-1-yl)-3-amino-2-(2-hydroxyethyloxy)pyridine,
6-(2-carboxamidopyrrolidin-1-yl)-3-amino-2-(2-hydroxyethyloxy)pyridine, 6-(2-dimethylcarboxamidopyrrolidin-1-yl)-3-amino-2-(2-hydroxyethyloxy)pyridine,
6-(2-carboxamido-3-hydroxypyrrolidin-1-yl)-3-amino-2-(2-hydroxyethyloxy)pyridine,
6-(2-carboxamido-4-hydroxypyrrolidin-1-yl)-3-amino-2-(2-hydroxyethyloxy)pyridine,
6-(pyrrolidin-1-yl)-3-amino-2-ethoxypyridine,
6-(3-hydroxypyrrolidin-1-yl)-3-amino-2-ethoxypyridine,
6-(3-aminopyrrolidin-1-yl)-3-amino-2-ethoxypyridine,
6-(3-acetamidopyrrolidin-1-yl)-3-amino-2-ethoxypyridine,
6-(3,4-dihydroxypyrrolidin-1-yl)-3-amino-2-ethoxypyridine,
6-(2-carboxypyrrolidin-1-yl)-3-amino-2-ethoxypyridine,
6-(2-carboxy-3-hydroxypyrrolidin-1-yl)-3-amino-2-ethoxypyridine,
6-(2-carboxy-4-hydroxypyrrolidin-1-yl)-3-amino-2-ethoxypyridine,
6-(2-(hydroxymethyl)pyrrolidin-1-yl)-3-amino-2-ethoxypyridine,
6-(2-hydroxymethyl-4-hydroxypyrrolidin-1-yl)-3-amino-2-ethoxypyridine,
6-(2-hydroxymethyl-2-hydroxypyrrolidin-1-yl)-3-amino-2-ethoxypyridine,
6-(2-carboxamidopyrrolidin-1-yl)-3-amino-2-ethoxypyridine,
6-(2-dimethylcarboxamidopyrrolidin-1-yl)-3-amino-2-ethoxypyridine,
6-(2-carboxamido-3-hydroxypyrrolidin-1-yl)-3-amino-2-ethoxypyridine,
6-(2-carboxamido-4-hydroxypyrrolidin-1-yl)-3-amino-2-ethoxypyridine,
and addition salts thereof.

12. The composition according to claim 11, wherein the at least one oxidation base chosen from formula (I) is chosen from:
2-methoxy-6-(pyrrolidin-1-yl)-3-aminopyridine,
5,6-diamino-2-(pyrrolidin-1-yl)pyridine,
N-(5,6-diaminopyridin-2-yl)-3-hydroxypyrrolidine,
2,6-did(pyrrolidin-1-yl)-5-aminopyridine,
and addition salts thereof.

13. The composition according to claim 1, further comprising at least one additional oxidation base other than those of formula (I), chosen from para-phenylenediamines, bisphenylalkylenediamines, para-aminophenols, ortho-aminophenols, heterocyclic bases and addition salts thereof.

14. The composition according to claim 13, wherein the at least one additional oxidation base is present in an amount ranging from 0.001 to 10% by weight, relative to the total weight of the composition.

15. The composition according to claim 1, wherein the at least one additional oxidation base chosen from formula (I) is present in an amount ranging from 0.001 to 10% by weight, relative to the total weight of the dyeing composition.

16. The composition according claim 1, further comprising at least one coupler chosen from meta-phenylenediamines, meta-aminophenols, meta-diphenols, naphthalene couplers and heterocyclic couplers, and addition salts thereof.

17. The composition according to claim 16, wherein the at least one coupler is present in an amount ranging from 0.001 to 10% by weight, relative to the total weight of the dyeing composition.

18. The composition according to claim 1 further comprising at least one oxidizing agent.

19. The composition according to claim 18, wherein the at least one oxidizing agent is chosen from hydrogen peroxide, urea hydrogen peroxide, alkali metal bromates, persalts, peracids and oxidase enzymes.

20. A process for oxidation dyeing of keratin fibers, comprising applying to the fibers at least one dyeing composition comprising, in medium acceptable for dyeing, at least one oxidation base chosen from formula (I) and addition salts thereof:

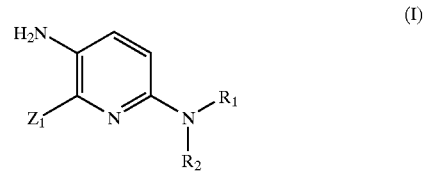

wherein
$Z_1$ is chosen from $OR_3$ and $NR_4R_5$ radicals;
$R_1$, $R_2$, $R_4$ and $R_5$, independently of one another, are chosen from a hydrogen atom, $C_1$–$C_6$ alkyl radicals, $C_2$–$C_6$ (poly)aminoalkyl radicals, $C_2$–$C_6$ (poly)alkylaminoalkyl radicals, $C_2$–$C_6$ aminohydroxyalkyl radicals, $C_2$–$C_6$ acylaminoalkyl radicals, $C_2$–$C_6$ alkoxyalkyl radicals, $C_2$–$C_6$ hydroxyalkoxyalkyl radicals, $C_2$–$C_6$ aminoalkoxyalkyl radicals, $C_2$–$C_6$ (poly)hydroxyalkyl radicals, $C_2$–$C_6$ carboxylalkyl radicals and $C_2$–$C_6$ sulphoalkyl radicals;
or $R_1$ and $R_2$ may form, together with the nitrogen atom to which they are attached, a saturated heterocycle comprising from 5 to 8 ring members optionally substituted by at least one radical chosen from halogen atoms, amino, (di)alkylamino, hydroxyl, carboxyl, carboxamido, alkylsulphonylamino, acetamido and alkoxy radicals, and $C_1$–$C_6$ alkyl radicals optionally substituted by at least one radical chosen from hydroxyl, amino, (di)alkylamino, alkoxy, hydroxyalkoxy, aminoalkoxy, carboxyl, carboxamido, sulphonamido and sulpho radicals, wherein the heterocycle optionally comprises at least one group chosen from heteroatoms chosen from oxygen, optionally substituted nitrogen and sulphur and an $SO_2$ group, with the proviso that the heterocycle does not comprise a peroxide bond or a diazo or a nitroso radical;
or independently, $R_4$ and $R_5$ may form, together with the nitrogen atom to which they are attached, a saturated heterocycle comprising from 5 to 8 ring members optionally substituted by at least one radical chosen from halogen atoms, amino, (di)alkylamino, hydroxyl, carboxyl, carboxamido, alkylsulphonylamino, acetamido and alkoxy radicals, and $C_1$–$C_6$ alkyl radicals optionally substituted by at least one radical chosen from hydroxyl, amino, (di)alkylamino, alkoxy, hydroxyalkoxy, aminoalkoxy, carboxyl, carboxamido, sulphonamido and sulpho radicals, wherein the heterocycle optionally comprises at least one group chosen from heteroatoms chosen from oxygen, optionally substituted nitrogen and sulphur and an $SO_2$ group, with the proviso that the heterocycle does not comprise a peroxide bond or a diazo or a nitroso radical;
$R_3$ is chosen from linear and branched $C_1$–$C_6$ alkyl radicals optionally substituted by at least one radical chosen from hydroxyl, amino, $C_1$–$C_3$ mono- and dialkylamino radicals, wherein an alkyl part of the at least one radical is optionally substituted by at least one radical chosen from hydroxyl, amino, $C_1$–$C_2$ alkoxyalkoxy, and carboxyl radicals, with the proviso that the at least one oxidation base is not chosen from 2,3,6-triaminopyridine and addition salts thereof;

and developing a colour using at least one oxidizing agent.

21. The process according to claim 20, wherein the at least one oxidizing agent is chosen from hydrogen peroxide, urea hydrogen peroxide, alkali metal bromates, persalts, peracids and oxidase enzymes.

22. The process according to claim 20, comprising mixing, at the time of use, the at least one oxidizing agent with the at least one dyeing composition.

23. The process according to claim 20, comprising simultaneously applying to the fibers the at least one oxidizing agent in the form of an oxidizing composition and the at least one dyeing composition.

24. The process according to claim 20, comprising sequentially applying to the fibers the at least one oxidizing agent in the form of an oxidizing composition and the at least one dyeing composition.

25. A multi-compartment device or kit comprising multiple compartments, wherein a first compartment comprises a dyeing composition comprising at least one oxidation base chosen from formula (I) and addition salts thereof:

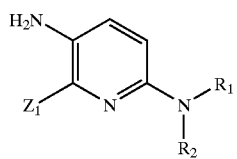

(I)

wherein $Z_1$ is chosen from $OR_3$ and $NR_4R_5$ radicals;

$R_1$, $R_2$, $R_4$ and $R_5$, independently of one another, are chosen from a hydrogen atom, $C_1$–$C_6$ alkyl radicals, $C_2$–$C_6$ (poly)aminoalkyl radicals, $C_2$–$C_6$ (poly)alkylaminoalkyl radicals, $C_2$–$C_6$ aminohydroxyalkyl radicals, $C_2$–$C_6$ acylaminoalkyl radicals, $C_2$–$C_6$ alkoxyalkyl radicals, $C_2$–$C_6$ hydroxyalkoxyalkyl radicals, $C_2$–$C_6$ aminoalkoxyalkyl radicals, $C_2$–$C_6$ (poly)hydroxyalkyl radicals, $C_2$–$C_6$ carboxylalkyl radicals and $C_2$–$C_6$ sulphoalkyl radicals;

or $R_1$ and $R_2$ may form, together with the nitrogen atom to which they are attached, a saturated heterocycle comprising from 5 to 8 ring members optionally substituted by at least one radical chosen from halogen atoms, amino, (di)alkylamino, hydroxyl, carboxyl, carboxamido, alkylsulphonylamino, acetamido and alkoxy radicals, and $C_1$–$C_6$ alkyl radicals optionally substituted by at least one radical chosen from hydroxyl, amino, (di)alkylamino, alkoxy, hydroxyalkoxy, aminoalkoxy, carboxyl, carboxamido, sulphonamido and sulpho radicals, wherein the heterocycle optionally comprises at least one group chosen from heteroatoms chosen from oxygen, optionally substituted nitrogen and sulphur and an $SO_2$ group, with the proviso that the heterocycle does not comprise a peroxide bond or a diazo or a nitroso radical;

or independently, $R_4$ and $R_5$ may form, together with the nitrogen atom to which they are attached, a saturated heterocycle comprising from 5 to 8 ring members optionally substituted by at least one radical chosen from halogen atoms, amino, (di)alkylamino, hydroxyl, carboxyl, carboxamido, alkylsulphonylamino, acetamido and alkoxy radicals, and $C_1$–$C_6$ alkyl radicals optionally substituted by at least one radical chosen from hydroxyl, amino, (di)alkylamino, alkoxy, hydroxyalkoxy, aminoalkoxy, carboxyl, carboxamido, sulphonamido and sulpho radicals, wherein the heterocycle optionally comprises at least one group chosen from heteroatoms chosen from oxygen, optionally substituted nitrogen and sulphur and an $SO_2$ group, with the proviso that the heterocycle does not comprise a peroxide bond or a diazo or a nitroso radical;

$R_3$ is chosen from linear and branched $C_1$–$C_6$ alkyl radicals optionally substituted by at least one radical chosen from hydroxyl, amino, $C_1$–$C_3$ mono- and dialkylamino radicals, wherein an alkyl part of the at least one radical is optionally substituted by at least one radical chosen from hydroxyl, amino, $C_1$–$C_2$ alkoxyalkoxy, and carboxyl radicals, with the proviso that the at least one oxidation base is not chosen from 2,3,6-triaminopyridine and addition salts thereof;

and a second compartment comprises an oxidizing composition.

26. A colored product obtained by oxidative coupling of a composition according to claim 1 in the presence of at least one oxidizing agent.

27. A process for dyeing keratin fibers, comprising applying to the fibers a dyeing composition comprising, in medium acceptable for dyeing, at least one oxidation base chosen from formula (I) and addition salts thereof:

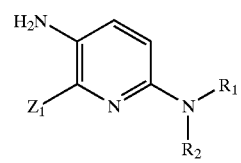

(I)

wherein $Z_1$ is chosen from $OR_3$ and $NR_4R_5$ radicals;

$R_1$, $R_2$, $R_4$ and $R_5$, independently of one another, are chosen from a hydrogen atom, $C_1$–$C_6$ alkyl radicals, $C_2$–$C_6$ (poly)aminoalkyl radicals, $C_2$–$C_6$ (poly)alkylamino alkyl radicals, $C_2$–$C_6$ aminohydroxyalkyl radicals, $C_2$–$C_6$ acylaminoalkyl radicals, $C_2$–$C_6$ alkoxyalkyl radicals, $C_2$–$C_6$ hydroxyalkoxyalkyl radicals, $C_2$–$C_6$ aminoalkoxyalkyl radicals, $C_2$–$C_6$ (poly)hydroxyalkyl radicals, $C_2$–$C_6$ carboxylalkyl radicals and $C_2$–$C_6$ sulphoalkyl radicals;

or $R_1$ and $R_2$ may form, together with the nitrogen atom to which they are attached, a saturated heterocycle comprising from 5 to 8 ring members optionally substituted by at least one radical chosen from halogen atoms, amino, (di)alkylamino, hydroxyl, carboxyl, carboxamido, alkylsulphonylamino, acetamido and alkoxy radicals, and $C_1$–$C_6$ alkyl radicals optionally substituted by at least one radical chosen from hydroxyl, amino, (di)alkylamino, alkoxy, hydroxyalkoxy, aminoalkoxy, carboxyl, carboxamido, sulphonamido and sulpho radicals, wherein the heterocycle optionally comprises at least one group chosen from heteroatoms chosen from oxygen, optionally substituted nitrogen and sulphur and an $SO_2$ group, with a proviso that the heterocycle does not comprise a peroxide bond or a diazo or a nitroso radical;

or independently, $R_4$ and $R_5$ may form, together with the nitrogen atom to which they are attached, a saturated heterocycle comprising from 5 to 8 ring members optionally substituted by at least one radical chosen from halogen atoms, amino, (di)alkylamino, hydroxyl, carboxyl, carboxamido, alkylsulphonylamino, acetamido and alkoxy radicals, and $C_1$–$C_6$ alkyl radicals optionally substituted by at least one radical chosen from hydroxyl, amino, (di)alkylamino, alkoxy, hydroxyalkoxy, aminoalkoxy, carboxyl, carboxamido, sulphonamido and sulpho radicals, wherein the heterocycle optionally comprises at least one group chosen from heteroatoms chosen from oxygen, optionally substituted nitrogen and sulphur and an $SO_2$ group, with a proviso that the heterocycle does not comprise a peroxide bond or a diazo or a nitroso radical;

$R_3$ is chosen from linear and branched $C_1$–$C_6$ alkyl radicals optionally substituted by at least one radical chosen from hydroxyl, amino, $C_1$–$C_3$ mono- and dialkylamino radicals, wherein an alkyl part of the at least one radical is optionally substituted by at least one radical chosen from hydroxyl, amino, $C_1$–$C_2$ alkoxyalkoxy, and carboxyl radicals, with the proviso that the at least one oxidation base is not chosen from 2,3,6-triaminopyridine and addition salts thereof.

28. A compound chosen from formula (I'):

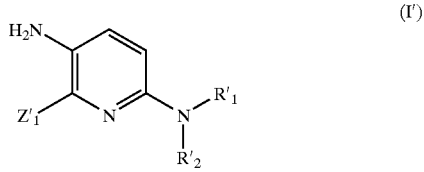

wherein:

$Z'_1$ is chosen from $OR'_3$ and $NR'_4R'_5$ radicals;

$R'_1$, $R'_2$, $R'_4$ and $R'_5$, independently of one another, are chosen from a hydrogen atom, $C_2$–$C_6$ (poly) aminoalkyl, $C_2$–$C_6$ (poly)alkylaminoalkyl, $C_2$–$C_6$ aminohydroxyalkyl, $C_2$–$C_6$ acylaminoalkyl, $C_2$–$C_6$ alkoxyalkyl, $C_2$–$C_6$ hydroxyalkoxyalkyl, $C_2$–$C_6$ aminoalkoxyalkyl, $C_2$–$C_6$ (poly)hydroxyalkyl, $C_2$–$C_6$ carboxylalkyl and $C_2$–$C_6$ sulphoalkyl radicals;

or $R'_1$ and $R'_2$ may form, together with the nitrogen atom to which they are attached, a saturated heterocycle comprising from 5 to 8 ring members optionally substituted by at least one radical chosen from halogen atoms, amino, (di)alkylamino, hydroxyl, carboxyl, carboxamido and alkoxy radicals, and $C_1$–$C_6$ alkyl radicals optionally substituted by at least one radical chosen from hydroxyl, amino, (di)alkylamino, alkoxy, hydroxyalkoxy, aminoalkoxy, carboxyl and sulpho radicals, wherein the heterocycle optionally comprises at least one group chosen from heteroatoms chosen from oxygen, optionally substituted nitrogen and sulphur and an $SO_2$ group, with the proviso that the heterocycle does not comprise a peroxide bond or a diazo or nitroso radical;

or independently, $R'_4$ and $R'_5$ may form, together with the nitrogen atom to which they are attached, a saturated heterocycle comprising from 5 to 8 ring members optionally substituted by at least one radical chosen from halogen atoms, amino, (di)alkylamino, hydroxyl, carboxyl, carboxamido and alkoxy radicals, and $C_1$–$C_6$ alkyl radicals optionally substituted by at least one radical chosen from hydroxyl, amino, (di)alkylamino, alkoxy, hydroxyalkoxy, aminoalkoxy, carboxyl and sulpho radicals, wherein the heterocycle optionally comprises at least one group chosen from heteroatoms chosen from oxygen, optionally substituted nitrogen, and sulphur and an $SO_2$ group, with the proviso that the heterocycle does not comprise a peroxide bond or a diazo or nitroso radical;

$R'_3$ is chosen from linear and branched $C_1$–$C_6$ alkyl radicals optionally substituted by at least one radical chosen from hydroxyl, amino, $C_1$–$C_3$ mono- and dialkylamino radicals, wherein an alkyl part of the at least one radical is optionally substituted by at least one radical chosen from hydroxyl, amino, $C_1$–$C_2$ alkoxyalkoxy, and carboxyl radicals;

and addition salts thereof, with the proviso that the compound of formula (I') is not chosen from 2,3,6-triaminopyridine, 6-(4-morpholinyl)-2,3-diaminopyridine, 6-(1-piperidinyl-2,3-diaminopyridine and 2,6-di-4-morpholinyl-3-aminopyridine, and addition salts thereof.

29. The compound of formula (I') according to claim 28, chosen from:

2-methoxy-6-(pyrrolidin-1-yl)-3-aminopyridine,
1-(5-amino-6-methoxypyridin-2-yl)pyrrolidin-3-ol,
3-amino-2-methoxy-6-(morpholin-4-yl)pyridine,
3-amino-2-methoxy-6-(piperidin-1-yl)pyridine,
6-N,N-(2-hydroxyethyl)-methyl)amino)-3-amino-2-methoxypyridine,
5,6-diamino-2-(pyrrolidin-1-yl)pyridine,
N-(5,6-diaminopyridin-2-yl)-3-hydroxypyrrolidine,
2,6-did(pyrrolidin-1-yl)-5-aminopyridine,
6-(pyrrolidin-1-yl)-2,3-diaminopyridine,
6-(3-hydroxypyrrolidin-1-yl)-2,3-diaminopyridine,
6-(3-aminopyrrolidin-1-yl)-2,3-diaminopyridine,
6-(3-acetamidopyrrolidin-1-yl)-2,3-diaminopyridine,
6-(3,4-dihydroxypyrrolidin-1-yl)-2,3-diaminopyridine,
6-(2-carboxypyrrolidin-1-yl)-2,3-diaminopyridine,
6-(2-carboxy-3-hydroxypyrrolidin-1-yl)-2,3-diaminopyridine,
6-(2-carboxy-4-hydroxypyrrolidin-1-yl)-2,3-diaminopyridine,
6-(2-(hydroxymethyl)pyrrolidin-1-yl)-2,3-diaminopyridine,
6-(2-hydroxymethyl-4-hydroxypyrrolidin-1-yl)-2,3-diaminopyridine,
6-(2-hydroxymethyl-2-hydroxypyrrolidin-1-yl)-2,3-diaminopyridine,
6-(2-carboxamidopyrrolidin-1-yl)-2,3-diaminopyridine,
6-(2-dimethylcarboxamidopyrrolidin-1-yl)-2,3-diaminopyridine,
6-(2-carboxamido-3-hydroxypyrrolidin-1-yl)-2,3-diaminopyridine,
6-(2-carboxamido-4-hydroxypyrrolidin-1-yl)-2,3-diaminopyridine,
6-(pyrrolidin-1-yl)-3-amino-2-methylaminopyridine,
6-(3-hydroxypyrrolidin-1-yl)-3-amino-2-methylaminopyridine, 6-(3-aminopyrrolidin-1-yl)-3-amino-2-methylaminopyridine,
6-(3-acetamidopyrrolidin-1-yl)-3-amino-2-methylaminopyridine,
6-(3,4-dihydroxypyrrolidin-1-yl)-3-amino-2-methylaminopyridine,
6-(2-carboxypyrrolidin-1-yl)-3-amino-2-methylaminopyridine,
6-(2-carboxy-3-hydroxypyrrolidin-1-yl)-3-amino-2-methylaminopyridine,
6-(2-carboxy-4-hydroxypyrrolidin-1-yl)-3-amino-2-methylaminopyridine,
6-(2-(hydroxymethyl)pyrrolidin-1-yl)-3-amino-2-methylaminopyridine,
6-(2-hydroxymethyl-4-hydroxypyrrolidin-1-yl)-3-amino-2-methylaminopyridine,
6-(2-hydroxymethyl-2-hydroxypyrrolidin-1-yl)-3-amino-2-methylaminopyridine,
6-(2-carboxamidopyrrolidin-1-yl)-3-amino-2-methylaminopyridine,
6-(2-dimethylcarboxamidopyrrolidin-1-yl)-3-amino-2-methylaminopyridine,
6-(2-carboxamido-3-hydroxypyrrolidin-1-yl)-3-amino-2-methylaminopyridine,
6-(2-carboxamido-4-hydroxypyrrolidin-1-yl)-3-amino-2-methylaminopyridine,
6-(pyrrolidin-1-yl)-3-amino-2-ethylaminopyridine,
6-(3-hydroxypyrrolidin-1-yl)-3-amino-2-ethylaminopyridine,
6-(3-aminopyrrolidin-1-yl)-3-amino-2-ethylaminopyridine,
6-(3-acetamidopyrrolidin-1-yl)-3-amino-2-ethylaminopyridine,
6-(3,4-dihydroxypyrrolidin-1-yl)-3-amino-2-ethylaminopyridine,
6-(2-carboxypyrrolidin-1-yl)-3-amino-2-ethylaminopyridine,
6-(2-carboxy-3-hydroxypyrrolidin-1-yl)-3-amino-2-ethylaminopyridine,
6-(2-carboxy-4-hydroxypyrrolidin-1-yl)-3-amino-2-ethylaminopyridine,
6-(2-(hydroxymethyl)pyrrolidin-1-yl)-3-amino-2-ethylaminopyridine,
6-(2-hydroxymethyl-4-hydroxypyrrolidin-1-yl)-3-amino-2-ethylaminopyridine,
6-(2-hydroxymethyl-2-hydroxypyrrolidin-1-yl)-3-amino-2-ethylaminopyridine,
6-(2-carboxamidopyrrolidin-1-yl)-3-amino-2-ethylaminopyridine,
6-(2-dimethylcarboxamidopyrrolidin-1-yl)-3-amino-2-ethylaminopyridine,
6-(2-carboxamido-3-hydroxypyrrolidin-1-yl)-3-amino-2-ethylaminopyridine,
6-(2-carboxamido-4-hydroxypyrrolidin-1-yl)-3-amino-2-ethylaminopyridine,
6-(pyrrolidin-1-yl)-3-amino-2-(2-hydroxyethylamino)pyridine,
6-(3-hydroxypyrrolidin-1-yl)-3-amino-2-(2-hydroxyethylamino)pyridine,
6-(3-aminopyrrolidin-1-yl)-3-amino-2-(2-hydroxyethylamino)pyridine,
6-(3-acetamidopyrrolidin-1-yl)-3-amino-2-(2-hydroxyethylamino)pyridine,
6-(3,4-dihydroxypyrrolidin-1-yl)-3-amino-2-(2-hydroxyethylamino)pyridine,
6-(2-carboxypyrrolidin-1-yl)-3-amino-2-(2-hydroxyethylamino)pyridine,
6-(2-carboxy-3-hydroxypyrrolidin-1-yl)-3-amino-2-(2-hydroxyethylamino)pyridine,
6-(2-carboxy-4-hydroxypyrrolidin-1-yl)-3-amino-2-(2-hydroxyethylamino)pyridine,
6-(2-(hydroxymethyl)pyrrolidin-1-yl)-3-amino-2-(2-hydroxyethylamino)pyridine,
6-(2-hydroxymethyl-4-hydroxypyrrolidin-1-yl)-3-amino-2-(2-hydroxyethylamino)pyridine,
6-(2-hydroxymethyl-2-hydroxypyrrolidin-1-yl)-3-amino-2-(2-hydroxyethylamino)pyridine,
6-(2-carboxamidopyrrolidin-1-yl)-3-amino-2-(2-hydroxyethylamino)pyridine,
6-(2-dimethylcarboxamidopyrrolidin-1-yl)-3-amino-2-(2-hydroxyethylamino)pyridine,
6-(2-carboxamido-3-hydroxypyrrolidin-1-yl)-3-amino-2-(2-hydroxyethylamino)pyridine,
6-(2-carboxamido-4-hydroxypyrrolidin-1-yl)-3-aminopyridine,
6-(pyrrolidin-1-yl)-3-amino-2-(2-aminoethylamino)pyridine,
6-(3-hydroxypyrrolidin-1-yl)-3-amino-2-(2-aminoethylamino)pyridine,
6-(3-aminopyrrolidin-1-yl)-3-amino-2-(2-aminoethylamino)pyridine,
6-(3-acetamidopyrrolidin-1-yl)-3-amino-2-(2-aminoethylamino)pyridine,
6-(3,4-dihydroxypyrrolidin-1-yl)-3-amino-2-(2-aminoethylamino)pyridine,
6-(2-carboxypyrrolidin-1-yl)-3-amino-2-(2-aminoethylamino)pyridine,
6-(2-carboxy-3-hydroxypyrrolidin-1-yl)-3-amino-2-(2-aminoethylamino)pyridine,
6-(2-carboxy-4-hydroxypyrrolidin-1-yl)-3-amino-2-(2-aminoethylamino)pyridine,
6-(2-(hydroxymethyl)pyrrolidin-1-yl)-3-amino-2-(2-aminoethylamino)pyridine,
6-(2-hydroxymethyl-4-hydroxypyrrolidin-1-yl)-3-amino-2-(2-aminoethylamino)pyridine,
6-(2-hydroxymethyl-2-hydroxypyrrolidin-1-yl)-3-amino-2-(2-aminoethylamino)pyridine,
6-(2-carboxamidopyrrolidin-1-yl)-3-amino-2-(2-aminoethylamino)pyridine,
6-(2-dimethylcarboxamidopyrrolidin-1-yl)-3-amino-2-(2-aminoethylamino)pyridine,
6-(2-carboxamido-3-hydroxypyrrolidin-1-yl)-3-amino-2-(2-aminoethylamino)pyridine,
6-(2-carboxamido-4-hydroxypyrrolidin-1-yl)-3-amino-2-(2-aminoethylamino)pyridine,
6-(pyrrolidin-1-yl)-3-amino-2-(2-acetamidoethylamino)pyridine,
6-(3-hydroxypyrrolidin-1-yl)-3-amino-2-(2-acetamidoethylamino)pyridine,
6-(3-aminopyrrolidin-1-yl)-3-amino-2-(2-acetamidoethylamino)pyridine,
6-(3-acetamidopyrrolidin-1-yl)-3-amino-2-(2-acetamidoethylamino)pyridine, 6-(3,4-dihydroxypyrrolidin-1-yl)-3-amino-2-(2-acetamidoethylamino)pyridine, 6-(2-carboxypyrrolidin-1-yl)-3-amino-2-(2-acetamidoethylamino)pyridine, 6-(2-carboxy-3-hydroxypyrrolidin-1-yl)-3-amino-2-(2-acetamidoethylamino)pyridine, 6-(2-carboxy-4-hydroxypyrrolidin-1-yl)-3-amino-2-(2-acetamidoethylamino)pyridine, 6-(2-(hydroxymethyl)pyrrolidin-1-yl)-3-amino-2-(2-acetamidoethylamino)pyridine, 6-(2-hydroxymethyl-4-hydroxypyrrolidin-1-yl)-3-amino-2-(2-acetamidoethylamino)pyridine, 6-(2-hydroxymethyl-2-hydroxypyrrolidin-1-yl)-3-amino-2-(2-acetamidoethylamino)pyridine, 6-(2-carboxamidopyrrolidin-1-yl)-3-amino-2-(2-acetamidoethylamino)pyridine, 6-(2-dimethylcarboxamidopyrrolidin-1-yl)-3-amino-2-(2-acetamidoethylamino)pyridine, 6-(2-carboxamido-3-hydroxypyrrolidin-1-yl)-3-amino-2-(2-acetamidoethylamino)pyridine, 6-(2-carboxamido-4-hydroxypyrrolidin-1-yl)-3-amino-2-(2-acetamidoethylamino)pyridine, 6-(pyrrolidin-1-yl)-3-amino-2-(pyrrolidin-1-yl)pyridine, 6-(3-hydroxypyrrolidin-1-yl)-3-amino-2-(pyrrolidin-1-yl)pyridine, 6-(3-aminopyrrolidin-1-yl)-3-amino-2-(pyrrolidin-1-yl)pyridine, 6-(3-acetamidopyrrolidin-1-yl)-3-amino-2-(pyrrolidin-1-yl)pyridine, 6-(3,4-dihydroxypyrrolidin-1-yl)-3-amino-2-(pyrrolidin-1-yl)pyridine, 6-(2-carboxypyrrolidin-1-yl)-3-amino-2-(pyrrolidin-1-yl)pyridine, 6-(2-carboxy-3-hydroxypyrrolidin-1-yl)-3-amino-2-(pyrrolidin-1-yl)pyridine, 6-(2-carboxy-4-hydroxypyrrolidin-1-yl)-3-amino-2-(pyrrolidin-1-yl)pyridine, 6-(2-(hydroxymethyl)pyrrolidin-1-yl)-3-amino-2-(pyrrolidin-1-yl)pyridine, 6-(2-hydroxymethyl-4-hydroxypyrrolidin-1-yl)-3-amino-2-(pyrrolidin-1-yl)pyridine, 6-(2-hydroxymethyl-2-hydroxypyrrolidin-1-yl)-3-amino-2-(pyrrolidin-1-yl)pyridine, 6-(2-carboxamidopyrrolidin-1-yl)-3-amino-2-(pyrrolidin-1-yl)pyridine, 6-(2-dimethylcarboxamidopyrrolidin-1-yl)-3-amino-2-(pyrrolidin-1-yl)pyridine, 6-(2-carboxamido-3-hydroxypyrrolidin-1-yl)-3-amino-2-(pyrrolidin-1-yl)pyridine, 6-(2-carboxamido-4-hydroxypyrrolidin-1-yl)-3-amino-2-(pyrrolidin-1-yl)pyridine, 6-(pyrrolidin-1-yl)-3-amino-2-(3-hydroxypyrrolidin-1-yl)pyridine, 6-(3-hydroxypyrrolidin-1-yl)-3-amino-2-(3-hydroxypyrrolidin-1-yl)pyridine, 6-(3-aminopyrrolidin-1-yl)-3-amino-2-(3-hydroxypyrrolidin-1-yl)pyridine, 6-(3-acetamidopyrrolidin-1-yl)-3-amino-2-(3-hydroxypyrrolidin-1-yl)pyridine, 6-(3,4-dihydroxypyrrolidin-1-yl)-3-amino-2-(3-hydroxypyrrolidin-1-yl)pyridine, 6-(2-carboxypyrrolidin-1-yl)-3-amino-2-(3-hydroxypyrrolidin-1-yl)pyridine, 6-(2-carboxy-3-hydroxypyrrolidin-1-yl)-3-amino-2-(3-hydroxypyrrolidin-1-yl)pyridine, 6-(2-carboxy-4-hydroxypyrrolidin-1-yl)-3-amino-2-(3-hydroxypyrrolidin-1-yl)pyridine, 6-(2-(hydroxymethyl)pyrrolidin-1-yl)-3-amino-2-(3-hydroxypyrrolidin-1-yl)pyridine, 6-(2-hydroxymethyl-4-hydroxypyrrolidin-1-yl)-3-amino-2-(3-hydroxypyrrolidin-1-yl)pyridine, 6-(2-hydroxymethyl-2-hydroxypyrrolidin-1-yl)-3-amino-2-(3-hydroxypyrrolidin-1-yl)pyridine, 6-(2-carboxamidopyrrolidin-1-yl)-3-amino-2-(3-hydroxypyrrolidin-1-yl)pyridine, 6-(2-dimethylcarboxamidopyrrolidin-1-yl)-3-amino-2-(3-hydroxypyrrolidin-1-yl)pyridine, 6-(2-carboxamido-3-hydroxypyrrolidin-1-yl)-3-amino-2-(3-hydroxypyrrolidin-1-yl)pyridine, 6-(2-carboxamido-4-hydroxypyrrolidin-1-yl)-3-amino-2-(3-hydroxypyrrolidin-1-yl)pyridine, 6-(pyrrolidin-1-yl)-3-amino-2-(2-carboxypyrrolidin-1-yl)pyridine, 6-(3-hydroxypyrrolidin-1-yl)-3-amino-2-(2-carboxypyrrolidin-1-yl)pyridine, 6-(3-aminopyrrolidin-1-yl)-3-amino-2-(2-carboxypyrrolidin-1-yl)pyridine, 6-(3-acetamidopyrrolidin-1-yl)-3-amino-2-(2-carboxypyrrolidin-1-yl)pyridine, 6-(3,4-dihydroxypyrrolidin-1-yl)-3-amino-2-(2-carboxypyrrolidin-1-yl)pyridine, 6-(2-carboxypyrrolidin-1-yl)-3-amino-2-(2-carboxypyrrolidin-1-yl)pyridine, 6-(2-carboxy-3-hydroxypyrrolidin-1-yl)-3-amino-2-(2-carboxypyrrolidin-1-yl)pyridine, 6-(2-carboxy-4-hydroxypyrrolidin-1-yl)-3-amino-2-(2-carboxypyrrolidin-1-yl)pyridine, 6-(2-(hydroxymethyl)pyrrolidin-1-yl)-3-amino-2-(2-carboxypyrrolidin-1-yl)pyridine, 6-(2-hydroxymethyl-4-hydroxypyrrolidin-1-yl)-3-amino-2-(2-carboxypyrrolidin-1-yl)pyridine, 6-(2-hydroxymethyl-2-hydroxypyrrolidin-1-yl)-3-amino-2-(2-carboxypyrrolidin-1-yl)pyridine, 6-(2-carboxamidopyrrolidin-1-yl)-3-amino-2-(2-carboxypyrrolidin-1-yl)pyridine, 6-(2-dimethylcarboxamidopyrrolidin-1-yl)-3-amino-2-(2-carboxypyrrolidin-1-yl)pyridine, 6-(2-carboxamido-3-hydroxypyrrolidin-1-yl)-3-amino-2-(2-carboxypyrrolidin-1-yl)pyridine, 6-(2-carboxamido-4-hydroxypyrrolidin-1-yl)-3-amino-2-(2-carboxypyrrolidin-1-yl)pyridine, 6-(pyrrolidin-1-yl)-3-amino-2-(2-(hydroxymethyl)pyrrolidin-1-yl)pyridine, 6-(3-hydroxypyrrolidin-1-yl)-3-amino-2-(2-(hydroxymethyl)pyrrolidin-1-yl)pyridine, 6-(3-aminopyrrolidin-1-yl)-3-amino-2-(2-(hydroxymethyl)pyrrolidin-1-yl)pyridine, 6-(3-acetamidopyrrolidin-1-yl)-3-amino-2-(2-(hydroxymethyl)pyrrolidin-1-yl)pyridine, 6-(3,4-dihydroxypyrrolidin-1-yl)-3-amino-2-(2-(hydroxymethyl)pyrrolidin-1-yl)pyridine, 6-(2-carboxypyrrolidin-1-yl)-3-amino-2-(2-(hydroxymethyl)pyrrolidin-1-yl)pyridine, 6-(2-carboxy-3-hydroxypyrrolidin-1-yl)-3-amino-2-(2-(hydroxymethyl)pyrrolidin-1-yl)pyridine, 6-(2-carboxy-4-hydroxypyrrolidin-1-yl)-3-amino-2-(2-(hydroxymethyl)pyrrolidin-1-yl)pyridine, 6-(2-(hydroxymethyl)pyrrolidin-1-yl)-3-amino-2-(2-(hydroxymethyl)pyrrolidin-1-yl)pyridine, 6-(2-hydroxymethyl-4-hydroxypyrrolidin-1-yl)-3-amino-2-(2-(hydroxymethyl)pyrrolidin-1-yl)pyridine, 6-(2-hydroxymethyl-2-hydroxypyrrolidin-1-yl)-3-amino-2-(2-(hydroxymethyl)pyrrolidin-1-yl)pyridine, 6-(2-carboxamidopyrrolidin-1-yl)-3-amino-2-(2-(hydroxymethyl)pyrrolidin-1-yl)pyridine, 6-(2-dimethylcarboxamidopyrrolidin-1-yl)-3-amino-2-(2-(hydroxymethyl)pyrrolidin-1-yl)pyridine, 6-(2-carboxamido-3-hydroxypyrrolidin-1-yl)-3-amino-2-(2-(hydroxymethyl)pyrrolidin-1-yl)pyridine, 6-(2-carboxamido-4-hydroxypyrrolidin-1-yl)-3-amino-2-(2-(hydroxymethyl)pyrrolidin-1-yl)pyridine, 6-(pyrrolidin-1-yl)-3-amino-2-(2-carboxamidopyrrolidin-1-yl)pyridine, 6-(3-hydroxypyrrolidin-1-yl)-3-amino-2-(2-carboxamidopyrrolidin-1-yl)pyridine, 6-(3-aminopyrrolidin-1-yl)-3-amino-2-(2-carboxamidopyrrolidin-1-yl)pyridine, 6-(3-acetamidopyrrolidin-1-yl)-3-amino-2-(2-carboxamidopyrrolidin-1-yl)pyridine, 6-(3,4-dihydroxypyrrolidin-1-yl)-3-amino-2-(2-carboxamidopyrrolidin-1-yl)pyridine, 6-(2-carboxypyrrolidin-1-yl)-3-amino-2-(2-carboxamidopyrrolidin-1-yl)pyridine, 6-(2-carboxy-3-hydroxypyrrolidin-1-yl)-3-amino-2-(2-carboxamidopyrrolidin-1-yl)pyridine, 6-(2-carboxy-4-hydroxypyrrolidin-1-yl)-3-amino-2-(2-carboxamidopyrrolidin-1-yl)pyridine, 6-(2-(hydroxymethyl)pyrrolidin-1-yl)-3-amino-2-(2-carboxamidopyrrolidin-1-yl)pyridine, 6-(2-hydroxymethyl-4-hydroxypyrrolidin-1-yl)-3-amino-2-(2-carboxamidopyrrolidin-1-yl)pyridine, 6-(2-hydroxymethyl-2-hydroxypyrrolidin-1-yl)-3-amino-2-(2-carboxamidopyrrolidin-1-yl)pyridine, 6-(2-carboxamidopyrrolidin-1-yl)-3-amino-2-(2-carboxamidopyrrolidin-1-yl)pyridine, 6-(2-dimethylcarboxamidopyrrolidin-1-yl)-3-amino-2-(2-carboxamidopyrrolidin-1-yl)pyridine, 6-(2-carboxamido-3-hydroxypyrrolidin-1-yl)-3-amino-2-(2-carboxamidopyrrolidin-1-yl)pyridine, 6-(2-carboxamido-4-hydroxypyrrolidin-1-yl)-3-amino-2-(2-carboxamidopyrrolidin-1-yl)pyridine, 6-(pyrrolidin-1-yl)-3-amino-2-dimethylaminopyridine, 6-(3-hydroxypyrrolidin-1-yl)-3-amino-2-dimethylaminopyridine, 6-(3-aminopyrrolidin-1-yl)-3-amino-2-dimethylaminopyridine, 6-(3-acetamidopyrrolidin-1-yl)-3-amino-2-dimethylaminopyridine, 6-(3,4-dihydroxypyrrolidin-1-yl)-3-amino-2-dimethylaminopyridine, 6-(2-carboxypyrrolidin-1-yl)-3-amino-2-dimethylaminopyridine, 6-(2-carboxy-3-hydroxypyrrolidin-1-yl)-3-amino-2-dimethylaminopyridine, 6-(2-carboxy-4-hydroxypyrrolidin-1-yl)-3-amino-2-dimethylaminopyridine, 6-(2-(hydroxymethyl)pyrrolidin-1-yl)-3-amino-2-dimethylaminopyridine, 6-(2-hydroxymethyl-4-hydroxypyrrolidin-1-yl)-3-amino-2-dimethylaminopyridine, 6-(2-hydroxymethyl-2-hydroxypyrrolidin-1-yl)-3-amino-2-dimethylaminopyridine, 6-(2-carboxamidopyrrolidin-1-yl)-3-amino-2-dimethylaminopyridine, 6-(2-dimethylcarboxamidopyrrolidin-1-yl)-3-amino-2-dimethylaminopyridine, 6-(2-carboxamido-3-hydroxypyrrolidin-1-yl)-3-amino-2-dimethylaminopyridine, 6-(2-carboxamido-4-hydroxypyrrolidin-1-yl)-3-amino-2-dimethylaminopyridine, 6-(pyrrolidin-1-yl)-3-amino-2-[methyl(2-hydroxyethyl)amino]pyridine, 6-(3-hydroxypyrrolidin-1-yl)-3-amino-2-[methyl(2-hydroxyethyl)amino]pyridine, 6-(3-aminopyrrolidin-1-yl)-3-amino-2-[methyl(2-hydroxyethyl)amino]pyridine, 6-(3-acetamidopyrrolidin-1-yl)-3-amino-2-[methyl(2-hydroxyethyl)amino]pyridine, 6-(3,4-dihydroxypyrrolidin-1-yl)-3-amino-2-[methyl(2-hydroxyethyl)amino]pyridine, 6-(2-carboxypyrrolidin-1-yl)-3-amino-2-[methyl(2-hydroxyethyl)amino]pyridine, 6-(2-carboxy-3-hydroxypyrrolidin-1-yl)-3-amino-2-[methyl(2-hydroxyethyl)amino]pyridine, 6-(2-carboxy-4-hydroxypyrrolidin-1-yl)-3-amino-2-[methyl(2-hydroxyethyl)amino]pyridine, 6-(2-(hydroxymethyl)pyrrolidin-1-yl)-3-amino-2-[methyl(2-hydroxyethyl)amino]pyridine, 6-(2-hydroxymethyl-4-hydroxypyrrolidin-1-yl)-3-amino-2-[methyl(2-hydroxyethyl)amino]pyridine, 6-(2-hydroxymethyl-2-hydroxypyrrolidin-1-yl)-3-amino-2-[methyl(2-hydroxyethyl)amino]pyridine, 6-(2-carboxamidopyrrolidin-1-yl)-3-amino-2-[methyl(2-hydroxyethyl)amino]pyridine, 6-(2-dimethylcarboxamidopyrrolidin-1-yl)-3-amino-2-[methyl(2-hydroxyethyl)amino]pyridine, 6-(2-carboxamido-3-hydroxypyrrolidin-1-yl)-3-amino-2-[methyl(2-hydroxyethyl)amino]pyridine, 6-(2-carboxamido-4-hydroxypyrrolidin-1-yl)-3-amino-2-[methyl(2-hydroxyethyl)amino]pyridine, 6-(pyrrolidin-1-yl)-3-amino-2-[methyl(2-aminoethyl)amino]pyridine, 6-(3-hydroxypyrrolidin-1-yl)-3-amino-2-[methyl(2-aminoethyl)amino]pyridine, 6-(3-aminopyrrolidin-1-yl)-3-amino-2-[methyl(2-aminoethyl)amino]pyridine, 6-(3-acetamidopyrrolidin-1-yl)-3-amino-2-[methyl(2-aminoethyl)amino]pyridine, 6-(3,4-dihydroxypyrrolidin-1-yl)-3-amino-2-[methyl(2-aminoethyl)amino]pyridine, 6-(2-carboxypyrrolidin-1-yl)-3-amino-2-[methyl(2-aminoethyl)amino]pyridine, 6-(2-carboxy-3-hydroxypyrrolidin-1-yl)-3-amino-2-[methyl(2-aminoethyl)amino]pyridine, 6-(2-carboxy-4-hydroxypyrrolidin-1-yl)-3-amino-2-[methyl(2-aminoethyl)amino]pyridine, 6-(2-(hydroxymethyl)pyrrolidin-1-yl)-3-amino-2-[methyl(2-aminoethyl)amino]pyridine, 6-(2-hydroxymethyl-4-hydroxypyrrolidin-1-yl)-3-amino-2-[methyl(2-aminoethyl)amino]pyridine, 6-(2-hydroxymethyl-2-hydroxypyrrolidin-1-yl)-3-amino-2-[methyl(2-aminoethyl)amino]pyridine, 6-(2-carboxamidopyrrolidin-1-yl)-3-amino-2-[methyl(2-aminoethyl)amino]pyridine,
6-(2-dimethylcarboxamidopyrrolidin-1-yl)-3-amino-2-[methyl(2-aminoethyl)amino]pyridine,
6-(2-carboxamido-3-hydroxypyrrolidin-1-yl)-3-amino-2-[methyl(2-aminoethyl)amino]pyridine,
6-(2-carboxamido-4-hydroxypyrrolidin-1-yl)-3-amino-2-[methyl(2-aminoethyl)amino]pyridine,
6-(pyrrolidin-1-yl)-3-amino-2-[methyl(2-acetamidoethyl)amino]pyridine,
6-(3-hydroxypyrrolidin-1-yl)-3-amino-2-[methyl(2-acetamidoethyl)amino]pyridine,
6-(3-aminopyrrolidin-1-yl)-3-amino-2-[methyl(2-acetamidoethyl)amino]pyridine,
6-(3-acetamidopyrrolidin-1-yl)-3-amino-2-[methyl(2-acetamidoethyl)amino]pyridine,
6-(3,4-dihydroxypyrrolidin-1-yl)-3-amino-2-[methyl(2-acetamidoethyl)amino]pyridine,
6-(2-carboxypyrrolidin-1-yl)-3-amino-2-[methyl(2-acetamidoethyl)amino]pyridine,
6-(2-carboxy-3-hydroxypyrrolidin-1-yl)-3-amino-2-[methyl(2-acetamidoethyl)amino]pyridine,
6-(2-carboxy-4-hydroxypyrrolidin-1-yl)-3-amino-2-[methyl(2-acetamidoethyl)amino]pyridine,
6-(2-(hydroxymethyl)pyrrolidin-1-yl)-3-amino-2-[methyl(2-acetamidoethyl)amino]pyridine,
6-(2-hydroxymethyl-4-hydroxypyrrolidin-1-yl)-3-amino-2-[methyl(2-acetamidoethyl)amino]pyridine,
6-(2-hydroxymethyl-2-hydroxypyrrolidin-1-yl)-3-amino-2-[methyl(2-acetamidoethyl)amino]pyridine,
6-(2-carboxamidopyrrolidin-1-yl)-3-amino-2-[methyl(2-acetamidoethyl)amino]pyridine,
6-(2-dimethylcarboxamidopyrrolidin-1-yl)-3-amino-2-[methyl(2-acetamidoethyl)amino]pyridine,
6-(2-carboxamido-3-hydroxypyrrolidin-1-yl)-3-amino-2-[methyl(2-acetamidoethyl)amino]pyridine,
6-(2-carboxamido-4-hydroxypyrrolidin-1-yl)-3-amino-2-[methyl(2-acetamidoethyl)amino]pyridine,
6-(pyrrolidin-1-yl)-3-amino-2-methoxypyridine,
6-(3-hydroxypyrrolidin-1-yl)-3-amino-2-methoxypyridine,
6-(3-aminopyrrolidin-1-yl)-3-amino-2-methoxypyridine,
6-(3-acetamidopyrrolidin-1-yl)-3-amino-2-methoxypyridine,
6-(3,4-dihydroxypyrrolidin-1-yl)-3-amino-2-methoxypyridine,
6-(2-carboxypyrrolidin-1-yl)-3-amino-2-methoxypyridine,
6-(2-carboxy-3-hydroxypyrrolidin-1-yl)-3-amino-2-methoxypyridine,
6-(2-carboxy-4-hydroxypyrrolidin-1-yl)-3-amino-2-methoxypyridine,
6-(2-(hydroxymethyl)pyrrolidin-1-yl)-3-amino-2-methoxypyridine,
6-(2-hydroxymethyl-4-hydroxypyrrolidin-1-yl)-3-amino-2-methoxypyridine,
6-(2-hydroxymethyl-2-hydroxypyrrolidin-1-yl)-3-amino-2-methoxypyridine,
6-(2-carboxamidopyrrolidin-1-yl)-3-amino-2-methoxypyridine,
6-(2-dimethylcarboxamidopyrrolidin-1-yl)-3-amino-2-methoxypyridine,
6-(2-carboxamido-3-hydroxypyrrolidin-1-yl)-3-amino-2-methoxypyridine,
6-(2-carboxamido-4-hydroxypyrrolidin-1-yl)-3-amino-2-methoxypyridine,
6-(pyrrolidin-1-yl)-3-amino-2-(2-hydroxyethyloxy)pyridine,
6-(3-hydroxypyrrolidin-1-yl)-3-amino-2-(2-hydroxyethyloxy)pyridine,
6-(3-aminopyrrolidin-1-yl)-3-amino-2-(2-hydroxyethyloxy)pyridine,
6-(3-acetamidopyrrolidin-1-yl)-3-amino-2-(2-hydroxyethyloxy)pyridine,
6-(3,4-dihydroxypyrrolidin-1-yl)-3-amino-2-(2-hydroxyethyloxy)pyridine,
6-(2-carboxypyrrolidin-1-yl)-3-amino-2-(2-hydroxyethyloxy)pyridine,
6-(2-carboxy-3-hydroxypyrrolidin-1-yl)-3-amino-2-(2-hydroxyethyloxy)pyridine,
6-(2-carboxy-4-hydroxypyrrolidin-1-yl)-3-amino-2-(2-hydroxyethyloxy)pyridine,
6-(2-(hydroxymethyl)pyrrolidin-1-yl)-3-amino-2-(2-hydroxyethyloxy)pyridine,
6-(2-hydroxymethyl-4-hydroxypyrrolidin-1-yl)-3-amino-2-(2-hydroxyethyloxy)pyridine,
6-(2-hydroxymethyl-2-hydroxypyrrolidin-1-yl)-3-amino-2-(2-hydroxyethyloxy)pyridine,
6-(2-carboxamidopyrrolidin-1-yl)-3-amino-2-(2-hydroxyethyloxy)pyridine,
6-(2-dimethylcarboxamidopyrrolidin-1-yl)-3-amino-2-(2-hydroxyethyloxy)pyridine,
6-(2-carboxamido-3-hydroxypyrrolidin-1-yl)-3-amino-2-(2-hydroxyethyloxy)pyridine,
6-(2-carboxamido-4-hydroxypyrrolidin-1-yl)-3-amino-2-(2-hydroxyethyloxy)pyridine,
6-(pyrrolidin-1-yl)-3-amino-2-ethoxypyridine,
6-(3-hydroxypyrrolidin-1-yl)-3-amino-2-ethoxypyridine,
6-(3-aminopyrrolidin-1-yl)-3-amino-2-ethoxypyridine,
6-(3-acetamidopyrrolidin-1-yl)-3-amino-2-ethoxypyridine,
6-(3,4-dihydroxypyrrolidin-1-yl)-3-amino-2-ethoxypyridine,
6-(2-carboxypyrrolidin-1-yl)-3-amino-2-ethoxypyridine,
6-(2-carboxy-3-hydroxypyrrolidin-1-yl)-3-amino-2-ethoxypyridine,
6-(2-carboxy-4-hydroxypyrrolidin-1-yl)-3-amino-2-ethoxypyridine,
6-(2-(hydroxymethyl)pyrrolidin-1-yl)-3-amino-2-ethoxypyridine,
6-(2-hydroxymethyl-4-hydroxypyrrolidin-1-yl)-3-amino-2-ethoxypyridine,
6-(2-hydroxymethyl-2-hydroxypyrrolidin-1-yl)-3-amino-2-ethoxypyridine,
6-(2-carboxamidopyrrolidin-1-yl)-3-amino-2-ethoxypyridine,
6-(2-dimethylcarboxamidopyrrolidin-1-yl)-3-amino-2-ethoxypyridine,
6-(2-carboxamido-3-hydroxypyrrolidin-1-yl)-3-amino-2-ethoxypyridine,
6-(2-carboxamido-4-hydroxypyrrolidin-1-yl)-3-amino-2-ethoxypyridine,
and addition salts thereof.

* * * * *

UNITED STATES PATENT AND TRADEMARK OFFICE
CERTIFICATE OF CORRECTION

PATENT NO. : 6,837,908 B2
APPLICATION NO. : 10/293328
DATED : January 4, 2005
INVENTOR(S) : Laurent Vidal and Aziz Fadli It is certified that error appears in the above-identified patent and that said Letters Patent is hereby corrected as shown below:

In claim 1, column 32, line 53, "carboxylalkyl" should read --carboxyalkyl--.

In claim 4, column 33, line 37, "carboxylalkyl," should read --carboxyalkyl,--.

In claim 11, column 35, line 2, "2,6-did(pyrrolidin-l-yl)-5-aminopyridine," should read --2,6-di(pyrrolidin-1-yl)-5-aminopyridine,--.

In claim 11, column 40, line 36, "2-did methylaminopyridine," should read --2-dimethylaminopyridine,--.

In claim 11, column 41, line 15, "amino] pyridine," should read --amino]pyridine,--.

In claim 12, column 43, line 43, "2,6-did(pyrrolidin-l-yl)-5-aminopyridine," should read --2,6-di(pyrrolidin-1-yl)-5-aminopyridine,--.

In claim 20, column 44, line 31, "carboxylalkyl" should read --carboxyalkyl--.

In claim 25, column 45, line 48, "carboxylalkyl" should read --carboxyalkyl--.

In claim 27, column 46, lines 48-49, "(poly) alkylamino alkyl" should read --(poly)alkylaminoalkyl--.

In claim 27, column 46, line 53, "carboxylalkyl" should read --carboxyalkyl--.

In claim 28, column 47, line 50, "carboxylalkyl" should read --carboxyalkyl--.

UNITED STATES PATENT AND TRADEMARK OFFICE
CERTIFICATE OF CORRECTION

PATENT NO. : 6,837,908 B2
APPLICATION NO. : 10/293328
DATED : January 4, 2005
INVENTOR(S) : Laurent Vidal and Aziz Fadli It is certified that error appears in the above-identified patent and that said Letters Patent is hereby corrected as shown below:

In claim 29, column 48, line 39, "2,6-did(pyrrolidin-l-yl)-5-aminopyridine," should read --2,6-di(pyrrolidin-1-yl)-5-aminopyridine,--.

Signed and Sealed this

Sixteenth Day of September, 2008

JON W. DUDAS
*Director of the United States Patent and Trademark Office*